United States Patent
Levin

(10) Patent No.: US 6,687,657 B2
(45) Date of Patent: Feb. 3, 2004

(54) SELF-REFERENTIAL METHOD AND APPARATUS FOR CREATING STIMULUS REPRESENTATIONS THAT ARE INVARIANT UNDER SYSTEMATIC TRANSFORMATIONS OF SENSOR STATES

(76) Inventor: David N. Levin, 1720 N. LaSalle Dr., Unit 25, Chicago, IL (US) 60614

( * ) Notice: Subject to any disclaimer, the term of this patent is extended or adjusted under 35 U.S.C. 154(b) by 97 days.

(21) Appl. No.: 09/962,768

(22) Filed: Sep. 25, 2001

(65) Prior Publication Data

US 2002/0065633 A1 May 30, 2002

Related U.S. Application Data

(60) Provisional application No. 60/235,695, filed on Sep. 27, 2000.

(51) Int. Cl.[7] .............................................. G06F 13/00
(52) U.S. Cl. ..................... 702/189; 702/125; 702/126; 702/178; 702/198
(58) Field of Search .............................. 702/39, 54, 57, 702/86, 93, 104, 74, 126, 178, 189, 198, 125; 600/558; 435/6; 424/9.1; 704/56, 57

(56) References Cited

U.S. PATENT DOCUMENTS

| | | | | |
|---|---|---|---|---|
| 5,317,304 | A | | 5/1994 | Choi ........................... 340/571 |
| 5,493,273 | A | | 2/1996 | Smurlo et al. ............... 340/541 |
| 5,535,135 | A | | 7/1996 | Bush et al. ................... 364/496 |
| 5,690,893 | A | | 11/1997 | Ozawa et al. ................. 422/67 |
| 5,860,936 | A | * | 1/1999 | Levin ........................... 600/558 |
| 5,924,979 | A | * | 7/1999 | Swedlow et al. ............ 600/300 |
| 6,093,153 | A | * | 7/2000 | Levin ........................... 600/558 |
| 6,147,674 | A | * | 11/2000 | Rosenberg et al. .......... 345/157 |
| 6,199,018 | B1 | * | 3/2001 | Quist et al. .................... 702/34 |

OTHER PUBLICATIONS

PCT International Search Report for International Application No. PCT/US01/29887.

Jordan, Sabina E., et al., Discrete–Event Simulation for the Design and Evaluation of Physical Protection Systems, Proceedings of the 1998 Winter Simulation Conference, 1998, pp. 899–905.

* cited by examiner

*Primary Examiner*—Marc S Hoff
*Assistant Examiner*—Felix Suarez
(74) *Attorney, Agent, or Firm*—Welsh & Katz, Ltd.

(57) ABSTRACT

The inventive method and apparatus include sensory devices that invariantly represent stimuli in the presence of processes that cause systematic sensor state transformations. Such processes include: 1) alterations of the device's detector, 2) changes in the observational environment external to the sensory device and the stimuli, and 3) certain modifications of the presentation of the stimuli themselves. A specific embodiment of the present invention is an intelligent sensory device having a "front end" comprised of such a representation "engine". The detectors of such a sensory device need not be recalibrated, and its pattern analysis module need not be retrained, in order to account for the presence of the above-mentioned transformative processes. Another embodiment of the present invention is a communications system that encodes messages as representations of signals. The message is not corrupted by signal transformations due to a wide variety of processes affecting the transmitters, receivers, and the channels between them.

60 Claims, 20 Drawing Sheets

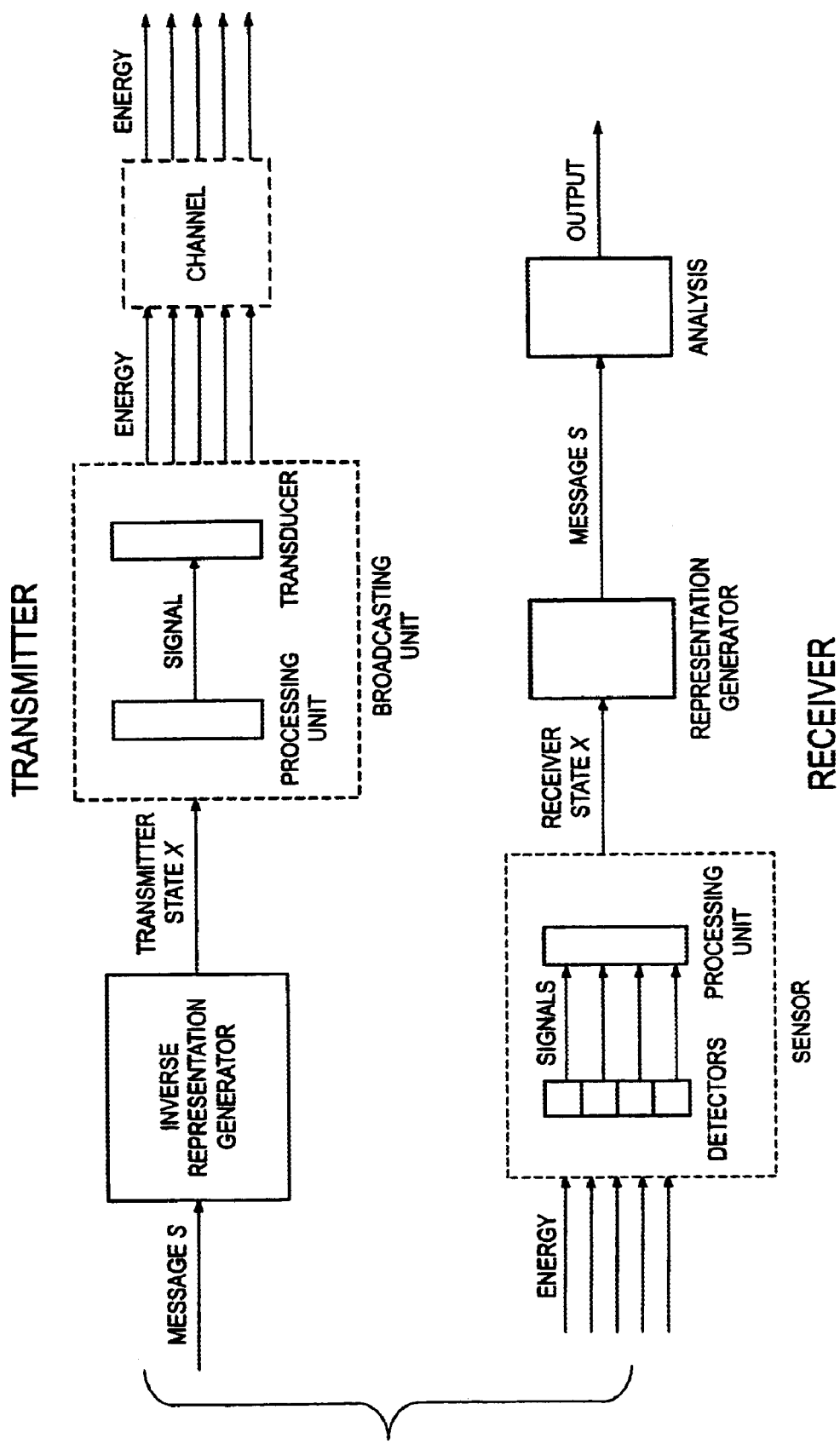

__US 6,687,657 B2__

SELF-REFERENTIAL METHOD AND APPARATUS FOR CREATING STIMULUS REPRESENTATIONS THAT ARE INVARIANT UNDER SYSTEMATIC TRANSFORMATIONS OF SENSOR STATES

This application claims the benefit of priority from copending provisional application Ser. No. 60/235,695 filed on Sep. 27, 2000, entitled Self-Referential Method and Apparatus For Creating Stimulus Representations That Are Invariant Under Systematic Transformations Of Sensor States, which is hereby incorporated by reference in its entirety.

A portion of this disclosure of this patent document contains material which is subject to copyright protection. The copyright owner has no objection to the facsimile reproduction by anyone of the patent document or the patent disclosure, as it appears in the Patent and Trademark Office Patent files or records, but otherwise reserves all copyright rights whatsoever.

FIELD OF THE INVENTION

The present invention relates generally to a method and apparatus that senses stimuli, creates internal representations of them, and uses its sensor data and their representations to understand aspects of the nature of the stimuli (e.g., recognize them). More specifically, the present invention is a method and apparatus that represents sensed stimuli in a manner that is invariant under systematic transformations of the device's sensor states. This device need not recalibrate its detector and/or retrain its pattern analysis module in order to account for sensor state transformations caused by extraneous processes (e.g., processes affecting the condition of the device's detectors, the channel between the stimuli and the device, and the manner of presentation of the stimuli themselves).

BACKGROUND OF THE INVENTION

Most intelligent sensory devices contain pattern recognition software for analyzing the state of the sensors that detect stimuli in the device's environment. This software is usually "trained" to classify a set of sensor states that are representative of the "unknown" sensor states to be subsequently encountered. For instance, an optical character recognition (OCR) device might be trained on letters and numbers in images of printed pages. Or, a speech recognition device may be trained to recognize the spoken words of a particular speaker. After these devices have been trained, their performance may be degraded if the correspondence between the stimuli and sensor states is altered by factors extrinsic to the stimuli of interest. For example, the OCR device may be "confused" by distortions of pixel patterns due to a derangement of the camera's optical/electronic path, or it may be unfamiliar with pixel intensity changes due to altered intensity of illumination of the printed page. Similarly, the speech recognition device may be compromised if the microphone's output signal is altered by changes in the microphone's internal response characteristics, or it may fail to recognize words if the frequency spectrum of sound is altered by changes in the transfer function of the "channel" between the speaker's lips and the microphone. These processes systematically deform the sensor states elicited by stimuli and thereby define a mapping of sensor states onto one another. If such transformations map one of the sensor states in the training set onto another one (e.g., the pixel intensity pattern of one letter is mapped onto that of another letter), the pattern recognition software will misclassify the corresponding stimuli. Likewise, the device will not recognize a stimulus in the training set if it's original sensor state has been transformed into one outside of the training set.

These problems can be addressed by periodically recalibrating the device's detector to account for sensor state transformations caused by changed conditions. For example, the device can be exposed to a stimulus consisting of a test pattern that produces a known sensor state under "normal" conditions. The observed differences between the actual sensor state and ideal sensor state for this test stimulus can be used to correct subsequently encountered sensor states. Alternatively, the device's pattern analysis (e.g. pattern recognition) module can be retrained to recognize the transformed sensor states. These procedures must be implemented after each change in observational conditions in order to account for time-dependent distortions. Because the device may not be able to detect the presence of such a change, it may be necessary to recalibrate or retrain it at short fixed intervals. However, this will decrease the device's duty cycle by frequently taking it "off-line". Furthermore, the recalibration or retraining process may be logistically impractical in some applications (e.g., computer vision and speech recognition devices at remote locations).

A similar problem occurs when the fidelity of electronic communication is degraded due to distortion of the signal as it propagates through the transmitter, receiver, and the channel between them. Most communications systems attempt to correct for these effects by periodically transmitting calibration data (e.g., test patterns) so that the receiver can characterize the distortion and then compensate for it by "unwarping" subsequently received signals. As mentioned above, these techniques may be costly because they periodically take the system "off-line" or otherwise reduce its efficiency.

SUMMARY OF THE INVENTION

The present invention substantially overcomes the disadvantages of prior sensory devices by providing a novel self-referential method and apparatus for creating stimulus representations that are invariant under systematic transformations of sensor states. Because of the invariance of the stimulus representations, the device effectively "filters out" the effects of sensor state transformations caused by extraneous processes (e.g., processes affecting the condition of the sensory device, the channel between the stimulus and the sensory device, and the manner of presentation of the stimulus itself). This means that the device can use these invariant representations to understand the nature of the stimuli (e.g., to recognize them), without explicitly accounting for the transformative processes (e.g., without recalibrating the device's detector and without retraining its pattern recognition module).

The behavior of this device mimics some aspects of human perception, which is remarkably invariant when raw signals are distorted by a variety of changes in observational conditions. This has been strikingly illustrated by experiments in which subjects wore goggles creating severe geometric distortions of the observed scene. For example, the visual input of some subjects was warped non-linearly, inverted, and/or reflected from right to left. Although the subjects initially perceived the distortion, their perceptions of the world returned to the pre-experimental baseline after several weeks of constant exposure to familiar stimuli seen through the goggles. For example, lines reported to be straight before the experiment were initially perceived to be warped, but these lines were once again reported to be straight after several weeks of viewing familiar scenes through the distorting lenses. Similar results were observed when the goggles were removed at the end of the experiment. Namely, the world initially appeared to be distorted in a manner opposite to the distortion due to the lenses, but eventually no distortion was perceived. These experiments suggest that humans utilize recent sensory experiences to adaptively "recalibrate" their perception of subsequent sensory data. There are many other examples of how our percepts are often invariant under changed observational conditions. For example, human observers are not usually confused by a different intensity of illumination of a scene. Although the raw sensory state of the observer is altered by this change, this is usually not attributed to changed intrinsic properties of the stimulus of interest (e.g., the scene). Similarly, humans perceive the information content of ordinary speech to be remarkably invariant, even though the signal may be transformed by significant alterations of the speaker's voice, the listener's auditory apparatus, and the channel between them. Yet there is no evidence that the speaker and listener exchange calibration data in order to characterize and compensate for these distortions. Rather, these observations suggest that the speech signal is redundant in the sense that listeners extract the same content from multiple acoustic signals that are transformed versions of one another. Finally, it is worth noting the tendency of different persons to share the same perceptions of the world, despite obvious differences in their sensory organs and processing pathways. This "universality" of perception may also be due to the apparent ability of each individual to "filter out" the effects of systematic sensor state transformations, including the transformations relating his/her sensor states to those of other individuals.

The present invention is a sensory method and apparatus that creates stimulus representations that are invariant in the presence of processes that remap its sensor states. These representations may share the following properties of human percepts: immediately after the onset of such a process, they may be affected, but they eventually adapt to the presence of sensor state transformations and return to the form that would have been produced in the absence of the transformative process. In order to see how to design such a device, consider any process that systematically alters the correspondence between the stimuli and the sensor states. For example, consider: 1) changes in the performance of the device's detectors (e.g., drifting gain of a detector circuit or distortion of an electronic image in a camera), 2) alterations of observational conditions that are external to the detectors and the stimuli (e.g., different intensity of a scene's illumination or different positioning of the detectors with respect to the stimuli), 3) systematic modifications of the presentation of the stimuli themselves (e.g., systematic warping of printed pages or systematic morphing of a voice). Because of such changes, a stimulus that formerly resulted in sensor state x will now induce another sensor state x'. Let the array of numbers x corresponding to a sensor state be the coordinates of that state on the manifold of possible sensor states. In this language, the above-mentioned processes systematically transform the absolute coordinates of the sensor state associated with each stimulus. However, certain relationships between the coordinates of a collection of sensor states may remain invariant in the presence of such a process. This is analogous to the fact that the physical rotation or translation of a collection of particles in a plane does not affect the relationships among the members of the collection, even though the absolute coordinates of each particle are transformed. For example, Euclidean coordinate geometry can be used to describe the relative positions of such particles in terms of a "natural" internal coordinate system (or scale) that is rooted in the collection's intrinsic structure; i.e., the coordinate system that originates at the collection's center of "mass" and is oriented along its principal moments of "inertia". Such a self-referential description is invariant under global rotations and translations that change the absolute coordinates of each particle. This suggests the following strategy: if we describe stimuli in terms of the relationships among their sensor states, we may be able to represent them in a way that is not affected by the above-described transformative processes. Specifically, we show that a sufficiently dense collection of sensor states in a time series has a locally defined structure that can be used to describe the relationship between each sensor state and the whole time series. Because this description is referred to the local structure of the collection of sensor states in the time series, it is invariant under any linear or non-linear transformations of all of the states in the collection. Now consider a specific embodiment of the invention that uses this method and apparatus to describe stimuli in terms of recently encountered stimuli. If a sufficient time has elapsed since the onset of a transformative process, each stimulus will be represented by the relationship between its transformed sensor state and a collection of recently encountered transformed sensor states. The resulting representation will identical to the one that would have been derived in the absence of the transformative process: namely, the representation describing the relationship between the corresponding untransformed sensor state and the collection of recently encountered untransformed sensor states. Furthermore, the stimulus will be represented in the same way as it was before the onset of the transformative process, as long as both representations were referred to collections of sensor states (transformed and untransformed) that were produced by the same sets of stimuli. In essence, the temporal stability of this type of stimulus representation is due to the stability of the device's recent "experience" (i.e., the stability of the set of recently encountered stimuli to which descriptions are referred). Immediately after the onset of a transformative process, the representation of a stimulus may drift during the transitional period when the device is referring its description to a mixed collection of untransformed and transformed sensor states. However, as in the human case, the representation of each stimulus will eventually revert to its baseline form when the collection of recently encountered states is entirely comprised of transformed sensor states In sensory devices of this type, the sensor signal is represented by a non-linear function of its instantaneous level at each time, with the form of this scale function being determined by the collection of signal levels encountered during a certain time period (e.g., during a recent period of time) [Levin, D. N., "Time-dependent signal representations that are independent of sensor calibration", Journal of the Acoustical Society of America, Vol. 108, p. 2575, 2000; Levin, D. N., "Stimulus representations that are invariant under invertible transformations of sensor data", Proceedings of the Society of Photoelectronic Instrumentation Engineers, Vol. 4322, pp. 1677–1688, 2001; Levin, D. N., "Universal communication among systems with heterogeneous 'voices' and 'ears'", Proceedings of the International Conference on Advances in Infrastructure for Electronic Business, Science, and Education on the Internet, Scuola Superiore G. Reiss Romoli S.p.A., L'Aquila, Italy, Aug. 6–12, 2001]. This rescaled signal is invariant if the signal levels at all relevant times are invertibly transformed by the same distortion. This is because the relationship between each untransformed signal level and the scale derived from the collection of untransformed signal levels is the same as the relationship between the corresponding transformed signal level and the scale derived from the collection of transformed signal levels. This can be understood in the context of the above-described analogy, involving the positions of particles in a plane. Each particle's position with respect to the collection's intrinsic coordinate system or scale is invariant under rigid rotations and translations that change all particle coordinates in an extrinsic coordinate system. This is because each particle and the collection's intrinsic coordinate system are rotated and translated in the same manner. According to the present invention, the signal levels detected by the sensory device in a suitable time period have an intrinsic structure that defines a non-linear coordinate system (or scale) on the manifold of possible signal levels. The "location" of the currently detected signal level with respect to this intrinsic coordinate system is invariant under any invertible transformation (linear or non-linear) of the entire signal time series. This is because the signal level at any time and the scale function at the same time point are transformed in a manner that leaves the rescaled signal level unchanged.

As suggested above, the task of representing stimuli in an invariant fashion can be reduced to the mathematical task of describing sensor state relationships that are not affected by systematic transformations on the sensor state manifold. Now, assume that the change in observational conditions defines a one-to-one transformation of the sensor states. This requirement simply excludes processes (e.g., a change in the spectral content of scene illumination) that make it possible to distinguish previously indistinguishable stimuli or that obscure the difference between previously distinguishable stimuli. Such a process has exactly the same effect on sensor state coordinates as a change of the coordinate system on the manifold ($x \rightarrow x'$) in the absence the process. This is analogous to the fact that the physical rotation of an array of particles in a plane has the same effect on their coordinates as the inverse rotation of the axes of the coordinate system. Therefore, the task of finding sensor state relationships that are independent of transformative processes is mathematically equivalent to the task of describing sensor state relationships in a coordinate-independent manner. In other words, the relationships among the sensor states must be described in a manner that is independent of the coordinate system used to label them. In specific embodiments of the invention, differential tensor calculus and differential geometry are used to provide the mathematical machinery for deriving such coordinate-independent descriptions of a time series of points on a manifold.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

FIG. 5a is a pictorial illustration of the non-linear signal transformation;

FIG. 5b is a pictorial illustration of the signal obtained by applying the transformation in FIG. 4c to the first half (167 ms) of the signal excerpted in FIG. 4a and by applying the transformation in FIG. 5a to the second half of that signal;

FIG. 5c is a pictorial illustration of the signal obtained by rescaling the signal in FIG. 5b, using the parameter $\Delta T=10$ ms;

FIG. 6a is a pictorial illustration of the signal derived from the signal in FIG. 4d by adding white noise with amplitudes randomly chosen from a uniform distribution between −200 and +200;

FIG. 6b is a pictorial illustration of the signal obtained by rescaling the signal in FIG. 6a with $\Delta T=10$ ms;

FIG. 7a is a pictorial illustration of the time course of the parameter g, which describes the state of speaker #1's vocal apparatus, during a particular utterance. Time is in seconds;

FIG. 7b is a pictorial illustration of the spectrogram of the sound produced by speaker #1 during the utterance described by g(t) in FIG. 7a. Time is in ms;

FIG. 7c is a pictorial illustration of the curve swept out by the third, fourth, and fifth cepstral coefficients of the spectra produced by speaker #1's vocal tract when it passed through all of its possible configurations (i.e., when the parameter g passed through all of its possible values);

FIG. 7d is a pictorial illustration of the sensor signal (left figure) induced in listener #1 when speaker #1 uttered the sound produced by the sequence of vocal apparatus configurations in FIG. 7a. Here, x denotes the instantaneous position of the sound spectrum's cepstral coefficients with respect to a convenient coordinate system along the curve in FIG. 7c. Time is in seconds. The right figure is the rescaled representation of the raw sensory signal on the left;

FIG. 8a is a pictorial illustration of the curve swept out by the second, third, and sixth DCT coefficients of the spectra produced by speaker #1's vocal tract, when it passed through all of its possible configurations;

FIG. 8b is a pictorial illustration of the sensor state (left figure) induced in listener #2 when speaker #1 uttered the sound produced by the sequence of vocal apparatus configurations in FIG. 7a. Here, x' denotes the instantaneous position of the sound spectrum's DCT coefficients with respect to a convenient coordinate system along the curve in FIG. 8a. Time is in seconds. The right figure is the rescaled representation of the sensor signal on the left;

FIG. 9a is a pictorial illustration of the spectrogram produced when speaker #2 uttered the sound described by the "gesture" function g(t) in FIG. 7a. Time is in ms;

FIG. 9b is a pictorial illustration of the curve swept out by the second, third, and sixth DCT coefficients of the spectra produced by speaker #2's vocal tract when it passed through all of its possible configurations (i.e., when the parameter g passed through all of its possible values);

FIG. 9c is a pictorial illustration of the sensor signal (left figure) produced in listener #2 when speaker #2 uttered the sound produced by the sequence of vocal apparatus configurations in FIG. 7a. Here, x' denotes the instantaneous position of the spectrum's DCT coefficients with respect to a convenient coordinate system along the curve in FIG. 9b. Time is in seconds. The right figure is the rescaled representation of the sensor signal on the left;

FIG. 18 is a pictorial illustration of the system for communicating information in the form of representations that are self-referentially encoded and decoded by the transmitter and receiver, respectively. The inverse representation generator finds the transmitter state x that corresponds to the representation s to be communicated. The state x controls the energy waveform that is transmitted by the broadcasting unit of the transmitter. After the energy traverses a channel, it is detected and processed by the receiver to create the receiver state x'. The representation generator in the receiver decodes x' as the representation s.

DETAILED DESCRIPTION OF THE INVENTION

In this written description, the use of the disjunctive is intended to include the conjunctive. The use of definite or indefinite articles in not intended to indicate cardinality. In particular, a reference to "the" object or thing or "an" object or "a" thing is intended to also describe a plurality of such objects or things.

It is to be further understood that the title of this section of the specification, namely, "Detailed Description of the Invention" relates to Rules of the U.S. Patent and Trademark Office, and is not intended to, does not imply, nor should be inferred to limit the subject matter disclosed herein or the scope of the invention.

I. Coordinate-independent Descriptions of Sensor States

Figure 1:
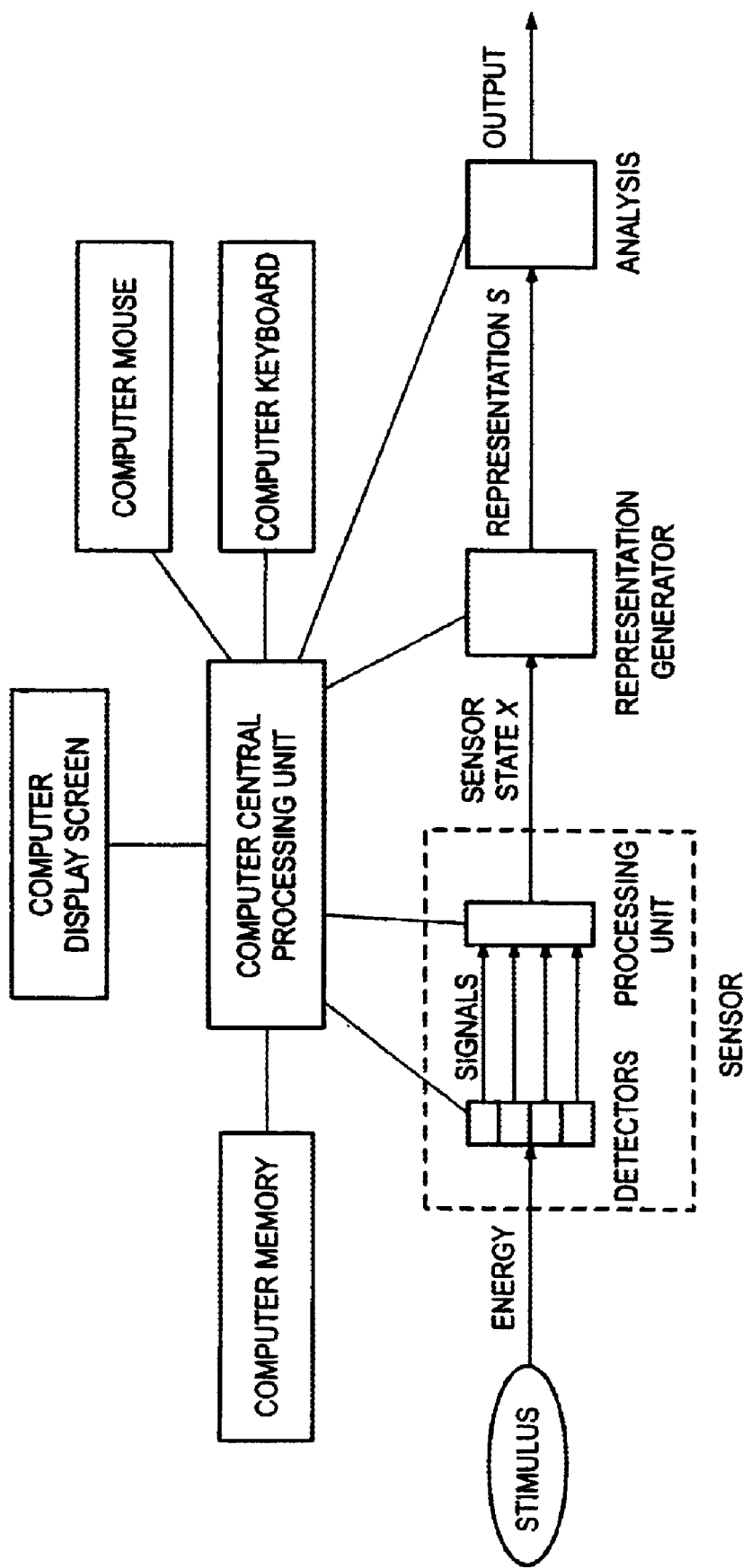
FIG. 1 is a pictorial diagram of a specific embodiment of a sensory device, according to the present invention, in which energy from a stimulus is detected and processed by a sensor to produce a sensor state characterized by an array of numbers x. The method and apparatus described in the present invention are used to generate a stimulus representation s from the sensor state x and sensor states encountered at chosen time points, and that representation is then subjected to higher level analysis (e.g., pattern recognition). The detectors, processing unit, representation generator, and analysis module are connected to a computer that is comprised of components selected from the group consisting of a central processing unit, memory unit, display unit, mouse, and keyboard.

One specific embodiment of the present invention is a sensory method and apparatus having a number of detectors that are sensitive to various features of stimuli (FIG. 1). For example, these detectors could respond to electromagnetic energy at various wavelengths, or they could respond to mechanical energy in the form of vibrations of the adjacent medium (e.g., air or water). These detectors may send their output to a processing unit that combines them in a possibly non-linear fashion. For example, in an imaging system, the processing units may determine the coordinates of a particular image feature. In a speech recognition system, the processing units could compute parameters characterizing aspects of the short-term Fourier spectrum of a microphone's signal. Let the device's sensor state x denote the entire array of numbers $x_k$ (k=1, ..., N, N≧1) that form the output of the processing unit.

Figure 2:
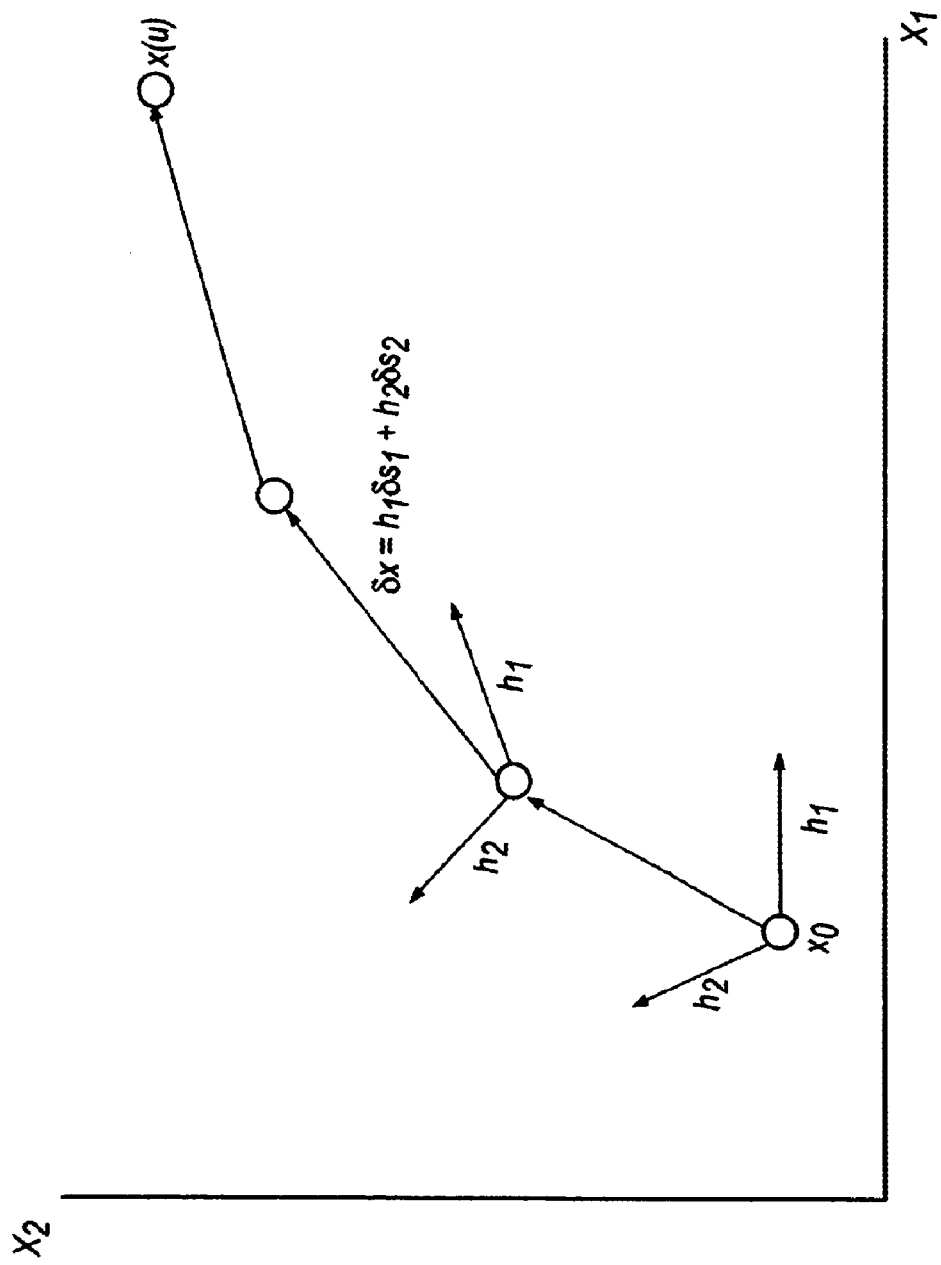
FIG. 2 is a pictorial illustration of a specific embodiment of a path $x(u)$ ($0 \leq u \leq 1$) between a reference sensor state $x_0$ and a sensor state of interest. If vectors $h_a$ can be defined at each point along the path, each line segment $\delta x$ can be decomposed into its components $\delta s_a$ along the vectors at that point.

Our goal is to create a description of the sensor states that is independent of the x coordinate system, which we happen to be using to label them. In other words, the same description must result if we used another (x') coordinate system to label the sensor states. Such a coordinate-independent description can be created with the help of coordinate-independent ways of identifying: 1) a reference sensor state ($x_0$), 2) a path x(u) (0≦u≦1) through the manifold of sensor states that connects the reference sensor state to the sensor state of interest (x(0)=$x_0$, x(1)=x), 3) N linearly-independent contravariant vectors $h_a$ (a=1 ..., N) at each point along the path (Levin, D. N., Method and apparatus for measurement, analysis, characterization, emulation, and translation of perception, U.S. Pat. No. 5,860,936, Jan. 19, 1999; Levin, D. N., Method and apparatus for measurement, analysis, characterization, emulation, and translation of perception, U.S. Pat. No. 6,093,153, Jul. 25, 2000; Levin, D. N., A differential geometric description of the relationships among perceptions, Journal of Mathematical Psychology, Vol. 44, pp. 241–284, 2000). Here, a vector h is said to be contravariant if it transforms as $$h \to h' = \frac{\partial x'}{\partial x} h$$

under the change of coordinate systems x→x'. If the foregoing conditions are met, each infinitesimal segment δx along the path can be decomposed into its components δs along the vectors $h_a$ (FIG. 2):

$$\delta x = \sum_{a=1,...,N} h_a \delta s_a \qquad \text{(Eq. 1)}$$

Note that δs is a coordinate-independent (scalar) quantity because δx and $h_a$ are contravariant vectors. Therefore, if the components δs are integrated over the specified path connecting $x_0$ and x, the result is a coordinate-independent description of the sensor state x:

$$s = \int_{x_0}^{x} \delta s \qquad \text{(Eq. 2)}$$

The next two sections show how the information required for this type of description (a reference state, paths connecting it to other sensor states, and the vectors $h_a$) can be derived from the local structure of a database of sensor states encountered at chosen time points.

II. Sensor State Manifolds Having Local Directionality

In this Section, we discuss the specific embodiment of the invention in which the vectors $h_a$ are directly derived from nearby sensor states encountered in a chosen time interval. For the sake of simplicity, this is first illustrated for one-dimensional (N=1) manifolds of sensor states. Then, we show how a similar procedure can be used to handle manifolds of any dimension.

II.A. One-dimensional Sensor State Manifolds Having Local Directionality

Consider the specific embodiment of the invention in which x is the number that characterizes the state of the device's sensor when it is exposed to a stimulus. For example, x could represent the intensity of a pixel at a certain spatial location in a digital image of a scene, or it could represent the amplitude of the output signal of a microphone. Suppose that the device has been exposed to a time-dependent series of stimuli, which produce sensor states x(t), where t denotes time, and let X be the sensor signal at time T. In this paragraph, we show how to rescale the signal level at this particular time point. The exact same procedure can be used to rescale the signal level at other times, thereby deriving a representation of the entire signal time series. Suppose that x(t) passes through all of the signal levels in [0, X] at one or more times during a chosen time interval of length ΔT (e.g. T−ΔT≦t<T). Here, ΔT is a parameter that can be chosen freely, although it influences the adaptivity and noise sensitivity of the method (see below). At each y∈[0, X], define the value of the function h(y) to be $$h(y) = \left\langle \frac{dx}{dt} \right\rangle_y \qquad \text{(Eq. 3)}$$

where the right side denotes the derivative averaged over those times in T−ΔT≦t<T when x(t) passes through the value y. If h(y) is non-vanishing for all y∈[0,X], it can be used to compute the scale function s(x) on this interval $$s(x) = \int_0^x \frac{dy}{h(y)} \qquad \text{(Eq. 4)}$$

The quantity S=s(X) can be considered to represent the level of the untransformed signal X at time T, after it has been non-linearly rescaled by means of the function s(x). Now, now consider the signal related to the untransformed signal by the time-independent transformation x→x'=x'(x). The transformation x'(x) could be the result of a time-independent distortion (linear or non-linear) that affects the signal as it propagates through the detector and other circuits of the sensory device, as well as through the channel between the stimulus and the sensory device. Furthermore, suppose that x→x' is invertible (i.e., x'(x) is monotonic), and suppose that it preserves the null signal (i.e., x'(0)=0). As mentioned earlier, the requirement of invertibility is relatively weak. It simply means that the distortion does not compromise the sensory device's ability to distinguish between signal levels. The transformed signal x'(t)=x'[x(t)] has the value X'=x'(X) at t=T. During T−ΔT≦t<T, x'(t) passes through each of the values in [0,X'], because of our assumption that x(t) attains all of the values in [0,X] during that time interval. Therefore, for each y'∈[0,X'], the process in Eq.(3) can be applied to the transformed signal in order to define the function h'(y') at time T $$h'(y') = \left\langle \frac{dx'}{dt} \right\rangle_{y'} \qquad \text{(Eq. 5)}$$

where the right side denotes the derivative averaged over those times in T−ΔT≦t<T when x'(t) passes through the value y'. By substituting x'(t)=x'[x(t)] in Eq.(5), using the chain rule of differentiation, and noting that x(t) passes through the value y when x'(t) passes through the value y'=x'(y), we find $$h'(y') = \frac{dx'}{dx}\bigg|_y h(y).$$

The function h'(y') is non-vanishing for y'∈[0, X'] because the monotonicity of x'(x) implies dx'/dx≠0. This means that the process in Eq.(4) can be used to compute a scale function s'(x') on this interval $$s'(x') = \int_0^{x'} \frac{dy'}{h'(y')} \qquad \text{(Eq. 6)}$$

The quantity S'=s'(X') represents the level of the transformed signal X' at time T, after it has been rescaled by means of a function s'(x'), which was derived from x'(t) just as s(x) was derived from x(t). Because of our assumption that x=0 transforms into x'=0, a change of variables (y→y') in Eq.(4) implies s'(x')=s(x) and, therefore, S'=S. This means that the rescaled value of a signal is invariant under the signal transformation x→x'. In other words, the rescaled value S of the undistorted signal level at time T, computed from recently encountered undistorted signal levels, will be the same as the rescaled value S' of the distorted signal level at time T, computed from recently encountered distorted signal levels. Now, the above procedure can be followed in order to rescale the signal levels at times other than T. The resulting time series of rescaled signal levels S(t), which the sensory device derives from the untransformed signal x(t) in this way, will be identical to the time series of rescaled signal levels S'(t), which the sensory device derives from the transformed signal x'(t). Note that the scale function defined by Eq.(4) is the same as that defined by Eqs.(1, 2) in the special case of a one-dimensional sensor state manifold. From this more general perspective, h(y) is the contravariant vector identified at each point on the one-dimensional sensor state manifold, and the null signal is the reference sensor state in each relevant coordinate system Notice that the forms of the scale functions s(x) and s'(x') (and of h(y) and h'(y')) will usually be time-dependent because they are computed from the time course of previously encountered signals. At some times, the sensory device may be unable to compute a rescaled signal level. This will happen if the scale function in Eq.(4) does not exist because the quantity h(y) vanishes for some y∈[0, X] or if the function h(y) cannot even be computed at some values of y because these signal levels were not encountered recently. Because of the monotonicity of x'(x), a signal invariant at such times cannot be computed from either the untransformed or transformed signals. The inability to compute signal invariants at some time points means that the number of independent signal invariants (i.e., the number of time points at which S(t) can be computed) may be less than the number of degrees of freedom in the raw signal from which the invariants were computed (i.e., the number of time points at which the signal x(t) is measured). The above-mentioned particle analogy suggests that this is not surprising. Note that there are a number of linear relationships among the coordinates of the particles when they are expressed in the collection's "center-of-mass" coordinate system. For example, their sum vanishes. Therefore, the number of independent invariants (i.e., the number of independent particle positions in the intrinsic coordinate system) is less than the number of degrees of freedom of the particle collection (i.e., the number of particle locations in an extrinsic coordinate system). This is because some of the collection's degrees of freedom were used to define the intrinsic coordinate system itself.

Figure 3A:
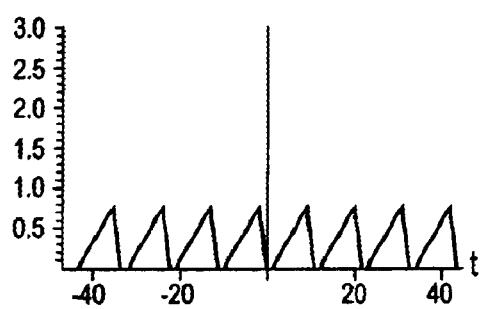
FIG. 3a is a pictorial illustration of an untransformed signal $x(t)$ describing a long succession of identical pulses that are uniformly spaced in time.
Figure 3B:
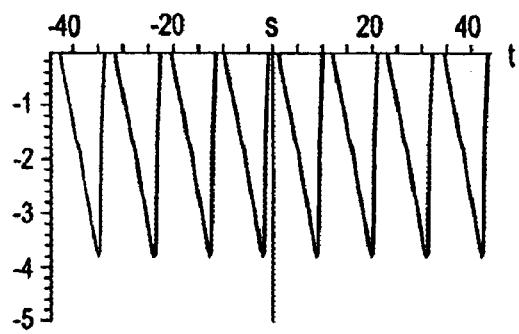
FIG. 3b is a pictorial illustration of the signal representation $S(t)$ that results from applying the rescaling method in Section II.A either to the signal in FIG. 3a or to the transformed version of that signal in FIG. 3c.
Figure 3C:
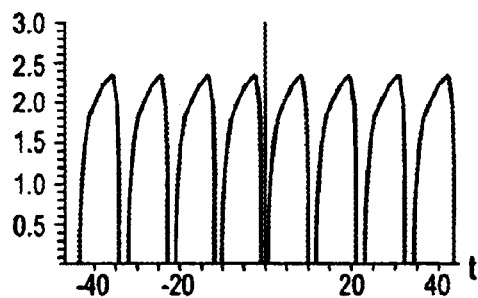
FIG. 3c is a pictorial illustration of the signal obtained by subjecting the signal in FIG. 3a to the distortion: $x'(x)=g_1 \ln(1+g_2 x)$ where $g_1=0.5$ and $g_2=150$.

It is useful to illustrate these results with a simple example. Suppose the untransformed signal x(t) is a long periodic sequence of triangular shapes, like those in FIG. 3a. For example, if the sensor state represents the intensity of a pixel in a digital image of a scene, FIG. 3a might be its response to a series of identical objects passing through the scene at a constant rate. Alternatively, if the sensor state represents the amplitude of a microphone's output, FIG. 3a might be its response to a series of uniformly spaced identical pulses. Let a and b be the slopes of the lines on the left and right sides, respectively, of each shape; FIG. 3a shows the special case: a=0.1 and b=−0.5 (measured in inverse time units). If we choose ΔT to be an integral number of periods of x(t), it is easy to see from Eqs.(3, 4) that the untransformed signal implies $h(y)=(a+b)/2$ and $S(t)=s[x(t)]=2x(t)/(a+b)$ at each point in time. FIG. 3b shows S(t), which is the untransformed signal after it has been rescaled at each time point as dictated by its earlier time course. Now, consider the transformed signal that is related to the untransformed signal by any of the following non-linear functions: $x'(x)=g_1 \ln(1+g_2 x)$ where $g_2>0$. For example, if $g_1=0.5$ and $g_2=150$, the transformed signal x'(t) looks like FIG. 3c. For instance, in the above-mentioned examples, this could represent the effect of a non-linear change in the gain of the detector (pixel intensity detector or microphone). When Eq.(5) is used to compute h'(y') from the transformed signal, the result is:

$$h'(y') = \frac{1}{2}(a+b)g_1 g_2 e^{-y'/g_1} \quad \text{(Eq. 7)}$$

at each point in time. Then, Eq.(6) shows that the rescaled version of the transformed signal is $$S(t) = s'[x'(t)] = \frac{2e^{x'(t)/g_1} - 1}{g_2(a+b)}, \quad \text{(Eq. 8)}$$

Substituting $x'(t)=x'[x(t)]$ into Eq.(8) shows that $S'(t)=S(t)$. In other words, the rescaled signal S'(t), which is derived from the transformed signal x'(t), is the same as the rescaled signal S(t), which is derived from the untransformed signal x(t). This is because the effect of the invertible signal transformation on the signal level at any given time ($x(t) \rightarrow x'(t)$) is compensated by its effect on the form of the scale function at that time ($s(x) \rightarrow s'(x')$). Notice that s(x) and s'(x') (as well as h(y) and h'(y')) happen to be time-independent in this particular example, and this implies that x(t) and x'(t) are rescaled in a time-independent fashion. This is because, in order to simplify the calculation, x(t) was chosen to be periodic and ΔT was chosen to be an integral number of these periods. In the general case, the scale functions depend on time in a manner dictated by the earlier time course of the signal. However, identical self-scaled signals (i.e., S(t)=S'(t)) will still be derived from the untransformed and transformed signals, as demonstrated by the proof at the beginning of this Section.

In the above discussion, the null signal was taken to be the reference sensor state $x_0$, and the signal transformation was assumed to preserve the null signal. In general, any sensor state can be taken to be the reference sensor state, as long as the reference sensor state $x_0'$ used to rescale a transformed signal time series is the transformed version of the reference state $x_0$ used to rescale the untransformed signal time series: i.e., as long as $x_0'=x'(x_0)$. In mathematical terms, this means that the reference state must be chosen in a coordinate-independent manner. For example, the reference sensor state could be chosen to be the sensor state that is the local maximum of a function defined to be the number of times each sensor state is encountered in a chosen time interval. Alternatively, prior knowledge may be used to choose the reference state. For instance, as described above, we may know that the null sensor state always corresponds to the same stimulus, and, therefore, it can be chosen to be the reference state. For example, this might be the case if the transformations of interest are due to changes in the intensity of a scene's illumination or alterations of the gain of a microphone circuit. Finally, the reference sensor state may be chosen to be the sensor state produced by a user-determined stimulus that is "shown" to the sensory device. Recall that the reference sensor state serves as the origin of the scale function used to rescale other sensor states. Therefore, this last procedure is analogous to having a choir leader play a note on a pitch pipe in order to "show" each singer the origin of the desired musical scale. Notice that stimulus representations that are referred to different reference sensor states will reflect different "points of view". For example, suppose that a device is observing a glass of beverage. It will "perceive" the glass to be half full or half empty if it uses reference sensor states corresponding to an empty glass or a full glass, respectively.

As mentioned previously, Eq.(1) can be used to find δs only if h(y) is well defined and non-vanishing at each y. In other words, this method requires that the sensor states encountered in a chosen time interval determine a non-vanishing one-dimensional vector at each point of the sensor state manifold; i.e., the sensor states encountered in the chosen time interval must impose some directionality and scale at each point. In Sections III and IV, we show how this requirement can be relaxed if the history of sensor states is used to define a coordinate-independent way of moving vectors on the manifold (i.e., a way of "parallel transporting" them). In that case, the manifold need only have well-defined directionality and scale at one point. The vector defined at that point can then be moved to all other points on the manifold in order to define vectors h(y) there.

Finally, in the above discussion, it was assumed that the sensory device encountered either a time series of untransformed signal levels or the corresponding time series of transformed signals and that these were related by a time-independent transformation. Now, suppose that there is the sudden onset of a process that causes transformation of subsequently encountered sensor states, and suppose that the rescaling of the signal is determined by signal levels encountered in the most recent period of length ΔT. During a transitional period of length ΔT after the transformation's onset, the sensory device will record a mixture of untransformed and transformed signal levels (e.g., a mixture of the shapes in FIGS. 3a and 3c). During this transition, the device's scale function will evolve from the form derived from untransformed signals to the form derived from transformed signals (e.g., from s(x) to s'(x)), and during this transitional period the transformed sensor states may be represented differently than the signals at corresponding times in the untransformed time series. However, once ΔT time units have elapsed since the transformation's onset, the device's scale function will be wholly derived from a time series of transformed sensor states. Thereafter, transformed signal levels will again be represented in the same way as the signals at corresponding times in the untransformed time series. Like a human, the system adapts to the presence of the transformation after a period of adjustment.

II.B. Multidimensional Sensor State Manifolds Having Local Directionality

In this section, we describe the specific embodiment of the invention in which the above approach is generalized to sensory devices with multiple detectors. Let the device's sensor state be represented by an array of numbers $x(x_k, k=1, \ldots, N$ where $N \geq 1)$, and let x(t) be the time series of sensor states encountered in a chosen time interval (e.g., the most recently time interval of length ΔT). This function describes a trajectory that crosses the sensor state manifold. We now show how these data can be used to define local vectors $h_a(x)$ in a manner that is independent of the coordinate system. Consider a point x that has multiple trajectory segments passing through it in at least N different directions, where N is the manifold's dimension. The time derivatives of the segments passing through x form a collection of contravariant vectors $\hat{h}_1$ at x:

$$\left(\hat{h}_i = \frac{dx}{dt}\bigg|\right)_{t_i} \tag{Eq. 9}$$

where $t_i$ denotes the $i^{th}$ time at which the trajectory passed through x. These quantities can be used to define N vectors at x if they tend to fall into clusters oriented along different directions in the manifold. To see this, pick an integer $C \geq N$ and partition the indices i into C non-empty sets labeled $S_c$ where $c=1, \ldots, C$. Next, compute the N×N covariance matrix $M_c$ of the vectors corresponding to each set of indices:

$$M_c = \frac{1}{N_c} \sum_{i \in S_c} \hat{h}_i \hat{h}_i \tag{Eq. 10}$$

where $N_c$ is the number of indices in $S_c$. Each of these matrices transforms as a tensor with two contravariant indices, and the determinant of each matrix $|MC_c|$ transforms as a scalar density of weight equal to minus two; namely, if coordinates on the manifold are transformed as $x \to x'$, then $$|M_c| \to |M_c'| = \left|\frac{\partial x'}{\partial x}\right|^2 |M_c| \tag{Eq. 11}$$

Next, compute E, which is defined to be the sum of powers of these determinants:

$$E = \sum_c |M_c|^p \tag{Eq. 12}$$

where p is some real positive number. Equation 11 implies that E transforms as a scalar density of weight $-2p$. In other embodiments of the present invention, E is defined differently; e.g., as another quantity that transforms as a scalar density of some weight. Now tabulate the values of E for all possible ways of partitioning the set of vectors $\hat{h}_1$ into C non-empty sets, and find the partition that results in the smallest value of E. This partition will tend to group the vectors into subsets with minimal matrix determinants. Therefore, the vectors in each group will tend to be linearly dependent or nearly linearly dependent, and they will tend to form a cluster that is oriented in one direction. Next, compute the vectors $h_c$ at x by finding the average vector in each part of the optimal partition:

$$h_c = \frac{1}{N_c} \sum_{i \in S_c} \hat{h}_i \tag{Eq. 13}$$

Because the $\hat{h}_1$ are contravariant vectors, the $h_c$ will also transform as contravariant vectors as long as they are partitioned in the same manner in any coordinate system. However, because E transforms by a positive multiplicative factor, the same partition minimizes it in any coordinate system. Therefore, the optimal partition is independent of the coordinate system, and the $h_c$ are indeed contravariant vectors. Finally, the indices of the $h_c$ can be relabeled so that the corresponding determinants $|M_c|$ are in order of ascending magnitude. This ordering is also coordinate-independent because these determinants transform by a positive multiplicative factor (Eq.(11)). As a result, if the foregoing computations are done in any coordinate system, the same vectors $h_c$ will be created, and these vectors provide a coordinate-independent characterization of the directionality of the trajectories passing through x.

The first N vectors that are linearly independent can be defined to be the $h_a$ in Eq.(1). These can be used to compute $\delta s$, the coordinate-independent representation of any line element passing through x. Once we have specified a path connecting a reference state $x_0$ to any sensor state x, Eq.(2) can be integrated to create a coordinate-independent representation s of that state. The path must be completely specified because the integral in Eq.(2) may be path-dependent. To see this, note that Eq.(1) can be inverted to form:

$$\delta s_a = \tilde{h}_a \cdot \delta x \tag{Eq. 14}$$

where the covariant vectors $\tilde{h}_a$ are found by solving $$\sum_{a=1,\ldots,N} \tilde{h}_{ak} h_a^l = \delta_k^l$$

and $\delta^1{}_k$ is the Kronecker delta function. It follows from Eq.(2) that each component of s is a line integral of $\tilde{h}_a$ for $a=1, \ldots, N$. Stoke's theorem shows that these line integrals will be path-dependent unless the "curl" of $\tilde{h}_a$ vanishes:

$$\frac{\partial \tilde{h}_{ak}}{\partial x_l} - \frac{\partial \tilde{h}_{al}}{\partial x_k} = 0 \tag{Eq. 15}$$

Because this may not be true for some sensor state manifolds, we must create a coordinate-independent way of specifying a path from $x_0$ to any point x on the manifold. In one specific embodiment of this invention, the path is determined in the following manner: first, generate a "type 1" trajectory through $x_0$ by moving along the local $h_1$ direction at $x_0$ and then moving along the $h_1$ direction at each subsequently encountered point. Next, generate a "type 2" trajectory through each point on the type 1 trajectory by moving along the local $h_2$ direction at that point and at each subsequently-encountered point. Continue in this fashion until a type N trajectory has been generated through each point on every trajectory of type N-1. Because of the linear independence of the $h_a$ at each point, the collection of points on type n trajectories ($1 \leq n \leq N$) comprises an n-dimensional subspace of the manifold. Therefore, each point on the manifold lies on a type N trajectory and can be reached from $x_0$ by traversing the following type of path: a segment of the type 1 trajectory, followed by a segment of a type 2 trajectory, followed by a segment of a type N trajectory. This path specification is coordinate-independent because the quantities $h_a$ transform as contravariant vectors. Therefore, if Eq.(2) is integrated along this "canonical" path, the resulting value of s provides a coordinate-independent description of the sensor state x in terms of the recently-encountered sensor states; i.e., a description that is invariant in the presence of processes that remap sensor states.

In order to illustrate this process, consider a manifold on which the sensor states move in several characteristic directions at every point. For example, imagine a large plane on which the sensor states have been observed to move at a fixed speed along the two directions of an invisible Cartesian grid. Or, consider a large sphere on which the sensor states move along invisible longitudes and latitudes at constant polar and azimuthal angular speeds, respectively. Equation (13) can used to derive local vectors (called "north" and "east") from the observed evolution of sensor states in the vicinity of each point. We can then create an east-west trajectory through a convenient reference point $x_0$ by moving away from it in locally specified east and west directions. Next, we can create north-south trajectories through each point on the east-west trajectory by moving away from it in the locally specified north and south directions. Each point on the manifold can then be represented by $s_n$, which is related to the distances traversed along the two types of trajectories in order to reach x from $x_0$. In the above-mentioned planar manifold example, this process may represent each point in a Cartesian coordinate system. On the other hand, in the spherical manifold example, each point may be represented by its longitude and its latitude (up to constant scale factors and a shift of the origin). In each case, the resulting representation does not depend on which coordinate system was originally used to record the evolution of sensor states and to derive local vectors from this data.

Strictly speaking, the vectors $h_a$ must be computed in the above-described manner at every point x on each path in Eq.(2). This means that the trajectory x(t) of previously encountered sensor states must cover the manifold very densely so that it passes through every point x at least N times. However, this requirement can be relaxed for most applications. Specifically, suppose that the $h_a$ are only computed at a finite collection of sample points on the manifold, and suppose that these vectors are computed from derivatives of trajectories passing through a very small neighborhood of each sample point (not necessarily passing through the sample point itself). Furthermore, suppose that values of $h_a$ between the sample points are estimated by parametric or non-parametric interpolation (e.g., splines or neural nets, respectively). This method of computation will be accurate as long as the spacing between the sample points is small relative to the distance over which the directionality of the manifold varies. This must be true in all relevant coordinate systems; i.e., in coordinate systems corresponding to the transformative effects of all interesting processes that remap the device's sensor states. Some circumstances may prevent the derivation of the $h_a$ at a sufficiently dense set of sample points on the manifold. For example, suppose that there is no unique way of partitioning the $h_1$ at each point in order to minimize E, or suppose that the $h_c$ (Eq.(13)) associated with a minimal value of E do not contain N linearly independent members. These results would indicate that the temporal course of sensor states x(t) does not endow the manifold with sufficient directionality. However, in this situation, it may still be possible to create coordinate-independent representations of stimuli by means of the methods in Sections III and IV, which only require that the manifold have intrinsic directionality at a single point. The vectors at that point can then be moved (parallel-transported) to other points on the manifold.

Note that certain exceptional points on the manifold may be connected to $x_0$ by more than one of the above-described "canonical" paths. For example, on the above-mentioned spherical manifold, the "north" pole may be connected to a reference point on the "equator" by multiple "canonical" paths. Specifically, the north pole can be reached by moving any distance along the equator (a possible east-west trajectory), followed by a movement of one-quarter of a great circle along the corresponding longitude (a possible "north-south" trajectory). Such exceptional points have multiple coordinate-independent representations (i.e., multiple s "coordinates").

III. Sensor State Manifolds that Support Parallel Transport

In this section, we describe a specific embodiment of the invention in which the temporal course of sensor states x(t) has sufficient internal structure to define a method of moving vectors ("parallel transporting" them) across the manifold. It may be possible to define parallel transport rules on a manifold, even in the absence of local directionality at every point, the property that was required to implement the method in Section II. As long as a manifold supports parallel transport and has directionality at a single point, vectors $h_a$ can be moved across the manifold from that point in order to define vectors $h_a$ at all other points in a coordinate-independent manner. Then, Eqs.(1–2) can be used to create coordinate-independent descriptions of sensor states. Roughly speaking, the vectors $h_a$ can be considered to intrinsically "mark" the manifold at one point. The parallel transport process makes it possible to "carry" this information across the manifold and make analogous "marks" at other points.

As in Section II.B, consider a device that has one or more detectors. Let the sensor state be represented by an array of numbers x ($x_k$, k=1, . . . , N where N≧1), and let x(t) be the time series of sensor states encountered in a chosen time interval. As before, this function describes a trajectory that crosses the sensor state manifold. According to the methods of affine-connected differential geometry, any vector can be moved across this manifold in a coordinate-independent manner if one can define a local affine connection $\Gamma_{lm}^{k}(x)$ which is a quantity transforming as:

$$\Gamma_{lm}^{\prime k} = \sum_{r,s,t=1,\ldots,N} \frac{\partial x_k'}{\partial x_r} \frac{\partial x_s}{\partial x_l'} \frac{\partial x_t}{\partial x_m'} \Gamma_{st}^{r} + \sum_{n=1,\ldots,N} \frac{\partial x_k'}{\partial x_n} \frac{\partial^2 x_n}{\partial x_l' \partial x_m'} \quad \text{(Eq. 16)}$$

Specifically, given any contravariant vector V at x, consider the array of numbers V+δV where:

$$\delta V^k = -\sum_{l,m=1,\ldots,N} \Gamma_{lm}^{k} V^l \delta x_m \quad \text{(Eq. 17)}$$

It can be shown that V+δV transforms as a contravariant vector at the point x+δx, as long as the affine connection transforms as shown in Eq.(16). The vector V+δV at x+δx is said to be the result of parallel transporting V along δx. Our task is to use the time series of sensor states x(t) to derive an affine connection on the sensor state manifold. Then, given a set of vectors $h_a$ at just one point on the manifold (e.g., at the reference sensor state $x_0$), we will be able to use the affine connection to populate the entire manifold with parallel-transported versions of those vectors. These can be used in Eqs.(1–2) to derive a coordinate-independent representation of any sensor state.

Consider a point x that is on at least N(N+1)/2 trajectory segments. Each of these segments can be divided into infinitesimal line elements dx that correspond to equal infinitesimal time intervals. These line elements transform as contravariant vectors. Therefore, we can look for affine connections that parallel transport a given line element along itself into the next line element on the same trajectory segment. In other words, we can look for affine connections for which a given trajectory segment is locally geodesic. Equation 17 shows that such an affine connection $\hat{\Gamma}_{lm}^{k}$ must satisfy the following N constraints:

$$\delta dx^k = -\sum_{l,m=1,\ldots,N} \hat{\Gamma}_{lm}^{k} dx_l dx_m \quad \text{(Eq. 18)}$$

where dx+δdx represents the trajectory's line element at x+dx. Now consider any collection of N(N+1)/2 of the trajectory segments at x. An affine connection that makes all of these trajectory segments locally geodesic must satisfy $N^2(N+1)/2$ linear constraints like those in Eq.(18). Because a symmetric affine connection ($\Gamma_{lm}{}^k = \Gamma_{ml}{}^k$) has $N^2(N+1)/2$ components, one and only symmetric connection satisfies these equations unless they happen to be inconsistent (no solutions) or redundant (multiple solutions). Notice that if $\hat{\Gamma}_{lm}{}^k$ is a solution of these equations in one coordinate system, then $\hat{\Gamma}'_{lm}{}^k$ is a solution of the corresponding equations in any other coordinate system, where $\hat{\Gamma}_{lm}{}^k$ and $\hat{\Gamma}'_{lm}{}^k$ are related by Eq.(16). Therefore, if these equations have a unique solution in one coordinate system, there is a unique solution of the corresponding equations in any other coordinate system, and these solutions are related by Eq.(16). Now, consider all collections of $N(N+1)/2$ trajectory segments that have a unique solution to these equations; i.e. all collections that are locally geodesic with respect to one and only one symmetric affine connection at x. Let $\Gamma_{lm}{}^k$ be the average of the affine connections computed from these subsets of trajectory segments:

$$\Gamma_{lm}^k = \frac{1}{N_T} \sum_{i=1,\ldots,N_T} \hat{\Gamma}_{lm}^k(i). \qquad \text{(Eq. 19)}$$

where $\hat{\Gamma}_{lm}{}^k(i)$ is the symmetric affine connection that makes the $i^{th}$ collection of trajectory segments locally geodesic and $N_T$ is the number of such collections. The quantity $\Gamma_{lm}{}^k$ transforms as shown by Eq.(16) because each contribution to the right side of Eq.(19) transforms in that way. Therefore, $\Gamma_{lm}{}^k$ can be defined to be the affine connection at point x on the sensor state manifold. Notice that it may be possible to derive an affine connection from the sensor state time series even if the local trajectory segments are not oriented along any particular "principal" directions. In other words, this method is more generally applicable than the method in Section II, which required that the trajectory segments be clustered along preferred directions at each point.

Now, suppose that a reference sensor state $x_0$ and N linearly independent reference vectors $h_a$ at $x_0$ can be defined on the manifold in a coordinate-independent manner. Several ways of defining $x_0$ were outlined in Section II.A. Section II.B described coordinate-independent techniques that could be used to derive reference vectors from sensor states encountered in the vicinity of $x_0$ in a chosen time period. Alternatively, the device may have prior knowledge of certain vectors at $x_0$ that are known to be numerically invariant under all relevant coordinate transformations, and these could be identified as the reference vectors. Or, the device's operator could choose the reference vectors and "show" them to the device by exposing it to the corresponding stimulus changes. Once the reference sensor state and reference vectors have been determined, the affine connection can be used to parallel transport these vectors to any other point x on the manifold. The resulting vectors at x will depend on the path that was used to create them if the manifold has non-zero curvature; i.e., if the curvature tensor $B_{lmn}{}^k$ is non-zero at some points, where:

$$B_{lmn}^k = -\frac{\partial \Gamma_{lm}^k}{\partial x_n} + \frac{\partial \Gamma_{ln}^k}{\partial x_m} + \sum_{i=1,\ldots,N} (\Gamma_{im}^k \Gamma_{ln}^i - \Gamma_{in}^k \Gamma_{lm}^i) \qquad \text{(Eq. 20)}$$

Because this tensor will not vanish in many cases, the path connecting $x_0$ and x must be completely specified in a coordinate-independent manner. In one specific embodiment of the present invention, such a path can be prescribed in the following fashion. Generate a trajectory through $x_0$ by repeatedly parallel transferring the vector $h_1$ along itself, and call this trajectory a type 1 geodesic. Next, parallel-transfer all of the vectors $h_a$ along this trajectory. Now, generate a type 2 geodesic through each point of this geodesic by repeatedly parallel transferring the vector $h_2$ along itself. Then, parallel-transfer all of the vectors $h_a$ along each of these geodesics, and generate a type 3 geodesic through each point on each type 2 geodesic by repeatedly parallel transferring the vector $h_3$ along itself. Continue in this manner until type N geodesics have been generated through each point on each type N-1 geodesic. Because of the linear independence of the vectors $h_a$ at $x_0$, the parallel transported $h_a$ will also be linearly independent. It follows that the collection of points on all trajectories of type n comprises an n-dimensional subspace of the manifold, and the type N trajectories will reach every point on the manifold. This means that any point x can be reached from $x_0$ by following a "canonical" path consisting of a segment of the type 1 geodesic, followed by a segment of a type 2 geodesic, . . . , followed by a segment of a type N geodesic. This path specification is coordinate-independent because it is defined in terms of a coordinate-independent operation: namely, the parallel transport of vectors. After the $h_a$ have been "spread" to the rest of the manifold along these paths, a coordinate-independent representation s of any point x can be generated by integrating Eq.(2) along the "canonical" path between $x_0$ and x.

In order to visualize the entire procedure described above, consider a manifold containing a single point $x_0$ at which vectors $h_a$ are locally specified; e.g., a plane or a small patch of a sphere that is intrinsically "marked" at $x_0$ with two "pointers" oriented in preferred directions on the sensor state manifold (called the "north" and "east" directions). Equation (19) can used to derive the affine connection at each point from the observed evolution of sensor states through it. For instance, if the sensor states move at constant speed along straight lines in the plane or along great circles on the sphere, Eq.(19) leads to the usual parallel transport rules of Riemannian geometry on a plane or sphere. The resulting affine connection can be used to parallel transport the east pointer along itself in order to create a "east-west" geodesic through $x_0$. We can then parallel transport the north pointer to create a new north pointer at each point along this east-west geodesic. Finally, we can parallel transport each north pointer along itself in order to create a north-south geodesic through it. Each point on the manifold can then be represented by $s_a$, which represents the number of parallel transport operations (east or west, followed by north or south) that are required to reach it from $x_0$. If the manifold is a plane with the above-described straight sensor trajectories and if the "north"/"east" pointers at $x_0$ are orthogonal, $s_a$ will represent each point in a Cartesian coordinate system. On the other hand, if the manifold is a sphere with the above-described great circular trajectories of sensor states, $s_a$ will represent each point by its longitude and latitude. In each case, the resulting representation does not depend on which coordinate system was originally used to record sensor states and to derive the affine connection.

Strictly speaking, the affine connection $\Gamma_{lm}{}^k$ must be computed from sensor state data at every point on the path used in Eq.(2). This means that the trajectory x(t) of sensor states encountered in a chosen time interval must cover the manifold densely so that it passes through each of these points at least $N(N+1)/2$ times. However, this requirement can be relaxed for most applications. Specifically, suppose that $\Gamma_{lm}{}^k$ is only computed at a finite collection of sample points on the manifold, and suppose that it is computed from trajectory segments passing through a very small neighborhood of each sample point (not necessarily through the point itself). Furthermore, suppose that values of $\Gamma_{lm}{}^k$ at intervening points are estimated by parametric or non-parametric interpolation (e.g., splines or neural nets, respectively). This method of computation will be accurate as long as the distance between sample points is small relative to the distance over which the locally geodesic affine connection changes. This must be true in all relevant coordinate systems; i.e., in coordinate systems that describe sensor states recorded in the presence of all expected transformative processes. If those transformations remap the sensor states in a relatively smooth fashion, the sampling and interpolation of the affine connection are likely to be accurate in all relevant coordinate systems, as long as they are accurate in one of them.

As mentioned previously, the above-described method is more generally applicable than the one in Section II.B. From a mathematical standpoint, this is because manifolds with well-defined directionality at each point (i.e., those in Section II.B) are a subset of manifolds that support parallel transport (i.e., those considered in this Section). To illustrate this statement, consider a vector V at point x on a manifold with directionality at each point. V has certain components when expressed as a linear combination of the vectors $h_a$ at x. At any other point on the manifold, we can define the parallel-transported version of V to be the same linear combination of the vectors $h_a$ at that point. It can be shown that this is equivalent to choosing the affine connection to be:

$$\Gamma^k_{lm} = -\sum_{a=1,\ldots,N} \tilde{h}_{al} \frac{\partial h_a^k}{\partial x_m} \qquad \text{(Eq. 21)}$$

The part of this expression that is symmetric in the lower two indices also constitutes an affine connection on the manifold. Thus, manifolds with local directionality have more than enough "structure" to support parallel transport.

IV. Sensor State Manifolds that Support Metrics

In this section, we describe a specific embodiment of the invention in which the time series of sensor states x(t) imposes a Riemannian metric on the manifold, even in the absence of local directionality at every point, the property that was required to implement the method in Section II.B. This metric can then be used to define parallel transport rules. As long as the manifold has sufficient directionality to define vectors $h_a$ at a single point, those vectors can be parallel transported in order to define vectors $h_a$ at all other points. Then, Eqs.(1–2) can be used to create coordinate-independent descriptions of sensor states.

As in Section II.B and Section III, consider a device that has one or more detectors. Let the sensor state be represented by an array of numbers x ($x_k$, k=1, . . . , N where N≧1), and let x(t) be the sensor state time series. Consider a point x that is on at least N(N+1)/2 trajectory segments. Each of these segments defines an infinitesimal line element dx=x(t+dt)−x(t), where t is the time at which the trajectory segment passed through x and dt is an infinitesimal time interval. Now consider one of these line elements, and look for metrics that assign unit length to it. Such a metric $\hat{g}_{kl}$ must satisfy the following constraint:

$$\sum_{k,l=1,\ldots,N} \hat{g}_{kl} dx_k dx_l = 1 \qquad \text{(Eq. 22)}$$

Next, consider any collection containing N(N+1)/2 of the line elements at x. A metric that assigns unit length to all of these line elements must satisfy N(N+1)/2 linear constraints like the one in Eq.(22). Because a metric has N(N+1)/2 components, one and only one metric satisfies these equations unless they happen to be inconsistent (no solutions) or redundant (multiple solutions). If these equations have a unique solution in one coordinate system, there is a unique solution of the corresponding equations in any other coordinate system, and these solutions define the same covariant tensor in the different coordinate systems. This is a consequence of the fact that each line element dx transforms as a contravariant vector. Now, consider all collections of N(N+1)/2 line elements that have a unique solution to these equations. Let $g_{kl}$ be the average of the metrics computed from these subsets of line elements:

$$g_{kl} = \frac{1}{N_L} \sum_{i=1,\ldots,N_L} \hat{g}_{kl}(i). \qquad \text{(Eq. 23)}$$

where $\hat{g}_{kl}(i)$ is the metric that assigns unit length to the $i^{th}$ collection of line elements and $N_L$ is the number of such collections. Note that sets of line elements for which Eq.(22) has no solution or multiple solutions do not contribute to Eq.(23). The quantity $g_{kl}$ transforms as a covariant tensor because each contribution to the right side of Eq.(23) transforms in that way. Therefore, $g_{kl}$ can be defined to be the metric at point x on the sensor state manifold. Notice that it may be possible to derive such a metric from the sensor state time series in a chosen interval even if the local trajectory segments are not oriented along any particular "principal" directions. In other words, this method is more generally applicable than the method in Section II.B, which required that the trajectory segments be clustered along preferred directions at each point.

The above-derived metric can now be used to define parallel transport on the sensor state manifold. For example, in one specific embodiment of the invention, the affine connection is determined to be the following quantity that preserves the metrically computed lengths of vectors during parallel transport:

$$\Gamma^k_{lm} = \frac{1}{2} \sum_{n=1,\ldots,N} g^{kn} \left( \frac{\partial g_{mn}}{\partial x_l} + \frac{\partial g_{nl}}{\partial x_m} - \frac{\partial g_{lm}}{\partial x_n} \right) \qquad \text{(Eq. 24)}$$

where $g^{kl}$ is the contravariant tensor that is the inverse of $g_{kl}$. Other definitions of the affine connection are also possible and are used in other embodiments of the invention. Now, suppose that a reference state $x_0$, together with N linearly independent vectors $h_a$ at $x_0$, can be defined on the sensor state manifold. Specific embodiments of the method and apparatus for doing this were described in Sections II.A and III. The above-described affine connection can be used to parallel transport these vectors to any other point x on the manifold. The resulting vectors at x will depend on the path that was used to create them if the manifold has non-zero curvature. Therefore, in general, the path connecting $x_0$ and x must be completely specified in a coordinate-independent manner. In one specific embodiment of the present invention, such a path is prescribed as it was in Section III. Namely, we can define a "canonical" path to x that follows a specific sequence of geodesics, which were created by parallel transport of the vectors $h_a$ at $x_0$. Then, a coordinate-independent representation s of any sensor state x can be generated by integrating Eq.(2) along the canonical path between $x_0$ and x.

As in Section III, the metric and the affine connection must be computed from sensor state data at every point on the paths used in Eq.(2). This means that the previously-encountered sensor state trajectory x(t) must cover the manifold densely so that it passes through each of these points at least $N(N+1)/2$ times. However, this requirement can usually be relaxed by computing the metric at a finite collection of sample points from trajectory segments passing through a very small neighborhood of each sample point (not necessarily through the point itself). Then, the values of $g_{kl}$ at intervening points can be estimated by parametric or non-parametric interpolation (e.g., splines or neural nets, respectively). As before, this method of computation will be accurate as long as the distance between sample points is small relative to the distance over which the metric changes.

In the specific embodiments of the present invention in this Section and in Sections II and III, the quantities $h_c$, $\Gamma_{lm}^{k}$, and $g_{kl}$ are computed by averaging over the $\hat{h}_i$, $\hat{\Gamma}_{lm}^{k}(i)$, and $\hat{g}_{kl}(i)$, respectively, and these quantities are computed from trajectory data in a chosen time interval; e.g., the time interval between $t-\Delta T$ and $t$. In other words, data from that epoch is weighted by unity, and data from prior times (before $t-\Delta T$) and subsequent times (after t) is weighted by zero. In other specific embodiments of the present invention, Eqs. 13, 19, and 23 are applied to data from each of multiple epochs (e.g., epochs demarcated by $t-N\Delta T$ and $t-(N-1)\Delta T$ where N is any integer) in order to compute $h_c(N)$, $\Gamma_{lm}^{k}(N)$, and $g_{kl}(N)$ for each epoch. Then, $h_c$, $\Gamma_{lm}^{k}$, and $g_{kl}$ can be computed by taking a weighted sum of $h_c(N)$, $\Gamma_{lm}^{k}(N)$, and $g_{kl}(N)$. For example, the weighting factor w(N) could become smaller as the magnitude of N increases.

Figure 4A:
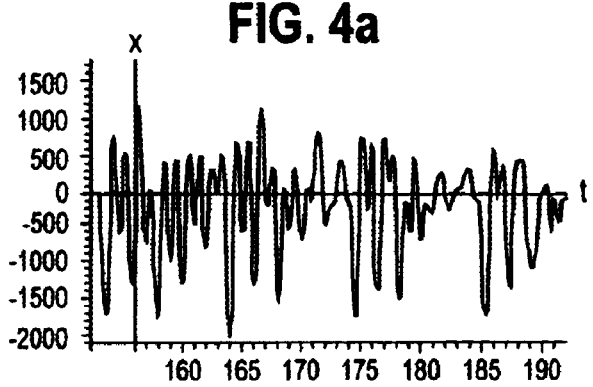
FIG. 4a is a pictorial illustration of the signal obtained by digitizing the acoustic signal of the word "door", uttered by an adult male speaker of American English. A 40 ms segment in the middle of the 334 ms signal is shown, with time given in ms. The horizontal lines show signal amplitudes that have rescaled values equal to $s=\pm 50n$ for $n=1, 2, \ldots$.
Figure 4B:
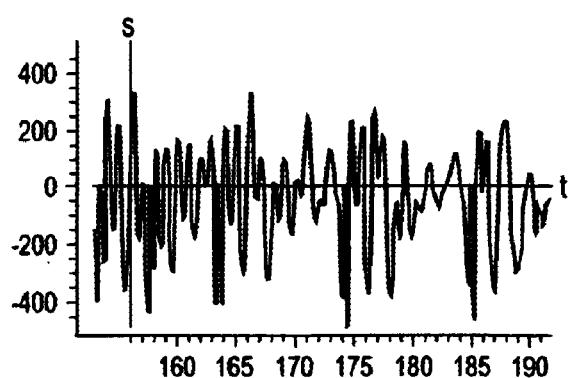
FIG. 4b is a pictorial illustration of the signal $S(t)$ (in units of $\mu s$) obtained by rescaling the signal in FIG. 4a, with the parameter $\Delta T=10$ ms.
Figure 4C:
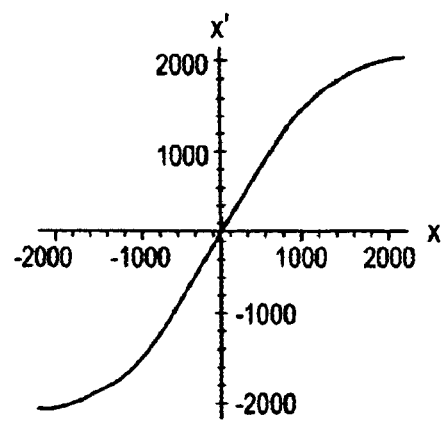
FIG. 4c is a pictorial illustration of the non-linear function $x'(x)$ that was used to transform the signal in FIG. 4a into the one in FIG. 4d.
Figure 4D:
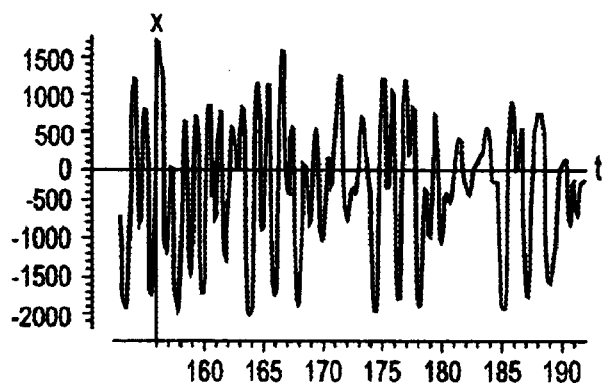
FIG. 4d is a pictorial illustration of the transformed version of the signal in FIG. 4a, obtained by applying the non-linear transformation in FIG. 4c.
Figure 4E:
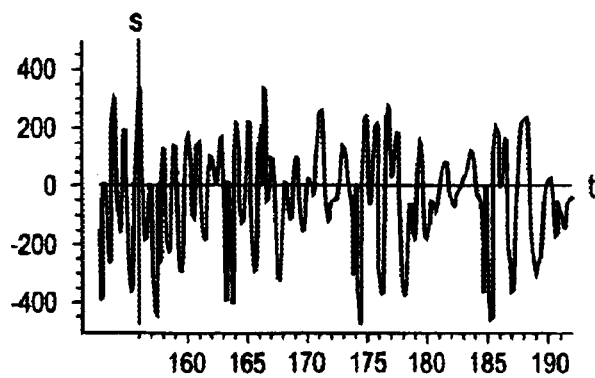
FIG. 4e is a pictorial illustration of the signal obtained by rescaling the signal in FIG. 4d with the parameter $\Delta T=10$ ms.

V. Tests with Simulated Data
V.A. One Dimensional Sensor State Manifolds
V.A.1. Acoustic Waveforms of Human Speech In this Section, the mathematical properties of the present invention are further illustrated by applying a specific embodiment of it to acoustic waveforms of human speech. An adult male American uttered English words with speed and loudness that were characteristic of normal conversation. These sounds were digitized with 16 bits of depth at a sample rate of 11.025 kHz. FIG. 4a shows a 40 ms segment of digitized signal (x(t)), located at the midpoint of the 334 ms signal corresponding to the word "door". FIG. 4b shows the "s representation" (i.e., the rescaled signal S(t)) that was derived from FIG. 4a by the method of Section II.A. The value of S was determined at each time point by a scale function s(x), which was derived from the previous 10 ms of signal (i.e., $\Delta T=10$ ms). These scale functions are shown by the horizontal lines in FIG. 4a, which denote values of x corresponding to $s=\pm 50n$ for $n=1, 2, \ldots$ FIG. 4d shows the signal that was derived from FIG. 4a by means of the non-linear transformation (x'(x)) shown in FIG. 4c. FIG. 4e is the rescaled signal that was derived from FIG. 4d with the parameter $\Delta T$ chosen to be 10 ms. Although there are significant differences between the "raw" signals in FIGS. 4a and 4d, their s representations (FIGS. 4b and 4e) are almost identical, except for a few small discrepancies that can be attributed to the discrete methods used to compute derivatives. Thus, the s representation was invariant under a non-linear signal transformation, as expected from the derivation in Section II.A. It is interesting to note that this result is apparent when one listens to the sounds represented in FIG. 4. Although all four signals in FIG. 4 sound like the word "door", there is a clear difference between the sounds of the two "raw" signals, and there is no perceptible difference between the sounds of their rescaled representations. In general, the rescaled signals sound like the word "door", uttered by a voice degraded by slight "static".

The above example suggests how dynamic rescaling might be used to enable universal communication among systems with a variety of transmitters and receivers. To see this, imagine that FIGS. 4a and 4d are the signals in the detector circuits of two receivers, which are "listening" to the same transmission. The non-linear transformation that relates these raw signals (FIG. 4c) could be due to differences in the receivers' detector circuits (e.g., their gain curves), or it could be due to differences in the channels between the receivers and the transmitter, or it could be due to a combination of these mechanisms. As long as both receivers use resealing to "decode" the detected signals, they will derive the same information content (i.e., the same function S(t)) from them. If one of the receivers is part of the system that originated the transmission (i.e., if this system is "listening" to its own transmission), then the information in the signal's s representation will be faithfully communicated to the other receiver, despite the fact that it has different "ears" than the transmitting system. Alternatively, imagine that FIGS. 4a and 4d are the signals in a single receiver, when it detects the broadcasts from two different transmitters. In this case, the non-linear transformation that relates these signals could be due to differences in the "voices" (i.e., the transmission characteristics) of the two transmitters. As long as the receiver "decodes" the detected signals by resealing, it will derive the same information content (i.e., the same S(t)) from them. In other words, it will "perceive" the two transmitters to be broadcasting the same message in two different "voices". As mentioned above, the transmitters will derive the same information content as the receivers if they "listen" to their own transmissions and then rescale them. In this way, systems with heterogeneous transmitters and receivers can communicate accurately without using calibration procedures to measure their transmission and reception characteristics.

Some comments should be made about technical aspects of the example in FIG. 4. The dynamically rescaled signals in FIGS. 4b and 4e were computed by a minor variant of the method in Section II.A. Specifically, we assumed that all signal transformations were monotonically positive, and we restricted the contributions to Eq.(3) and Eq.(5) to those time points at which the signal had a positive time derivative as it passed through the values y and y', respectively. The rescaled signal is still invariant because monotonically positive transformations do not change the sign of the signal's time derivative, and, therefore, the functions h(y) and h'(y') were still constructed from time derivatives at identical collections of time points. At each time point, we attempted to compute the rescaled signal from the signal time derivatives encountered during the most recent 10 ms ($\Delta T=10$ ms). At some times, the signal could not be rescaled because the signal level at that time was not attained during the previous 10 ms, and, therefore, there were no contributions to the right side of Eq.(3) for some values of y. For example, this happened at t~163, 174, and 185 ms in FIG. 4. As mentioned in Section II.A, this occurs at identical time points when resealing is applied to the untransformed signal (e.g., FIG. 4a) and to any transformed version of it (e.g., FIG. 4d). This means that the s representations of all of these signals are non-existent at identical time points and that at all other times they exist and have the same values. Therefore, this phenomenon does not corrupt the invariance of the signal's s representation, although it does reduce its information content. In this experiment, the s representation could be computed at 92% of all time points.

Figure 5A:
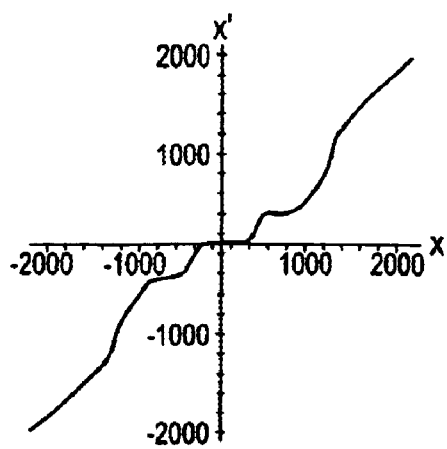
FIGS. 5a–c is a pictorial illustration of the effects of an abrupt change in the transformation of the signal.
Figure 5B:
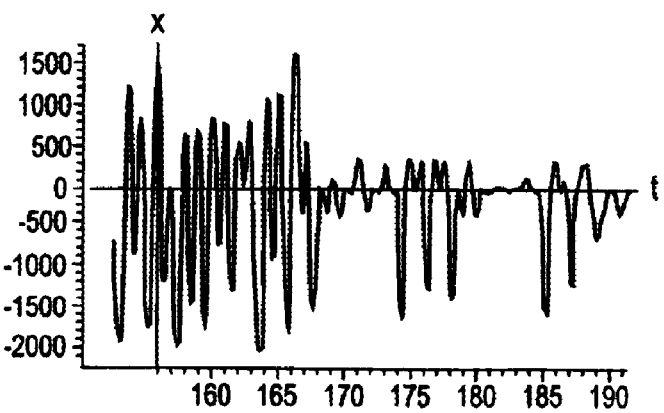
Figure 5C:
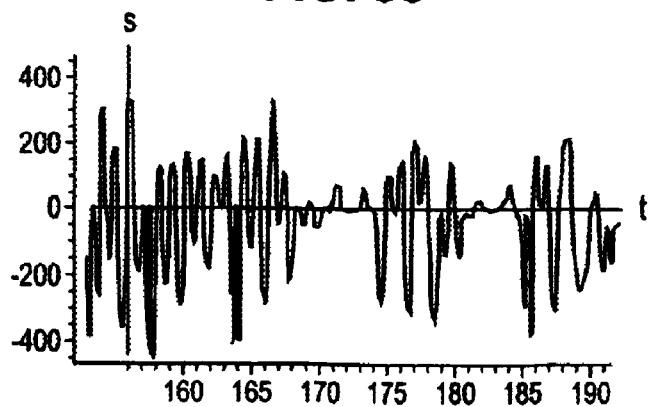

FIG. 5 shows what happened when the nature of the signal transformation changed abruptly. The signal in FIG. 5b was derived by applying the non-linear transformation in FIG. 4c to the first half (i.e., the first 167 ms) of the signal excerpted in FIG. 4a and by applying the non-linear transformation in FIG. 5a to the second half of that signal. FIG. 5c shows the s representation derived by rescaling FIG. 5b with $\Delta T=10$. Comparison of the latter to FIG. 4b shows that the s representation was invariant except during the time period $167\ ms \leq t \leq 177\ ms$. These discrepancies can be understood in the following way. During this time interval, the rescaled signal in FIG. 5c was derived from a mixed collection of signal levels, some of which were transformed as in FIG. 4c and some of which were transformed as in FIG. 5a. This violates the proof of invariance (Section II.A), which assumed the time-independence of the signal transformation. Notice the transitory nature of this corruption of the s representation. The rescaled signals in FIGS. 4b and 5c became identical again, once sufficient time ($\Delta T$) elapsed for the transformation to become time-independent over the time interval utilized by the rescaling procedure. In other words, the rescaling process was able to adapt to the new form of the transformation and thereby "recover" from the disturbance. This adaptive behavior resembles that of the human subjects of the goggle experiments mentioned in Summary of the Invention.

Figure 6A:
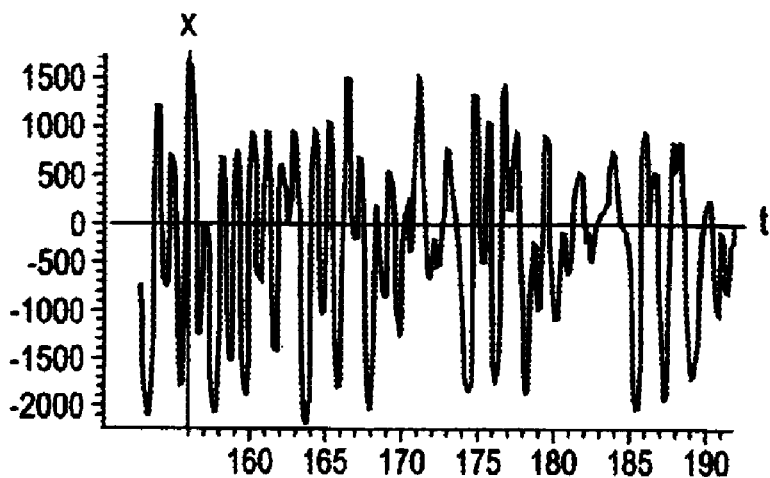
FIGS. 6a–b are pictorial illustrations of the effect of noise on the resealing process.
Figure 6B:
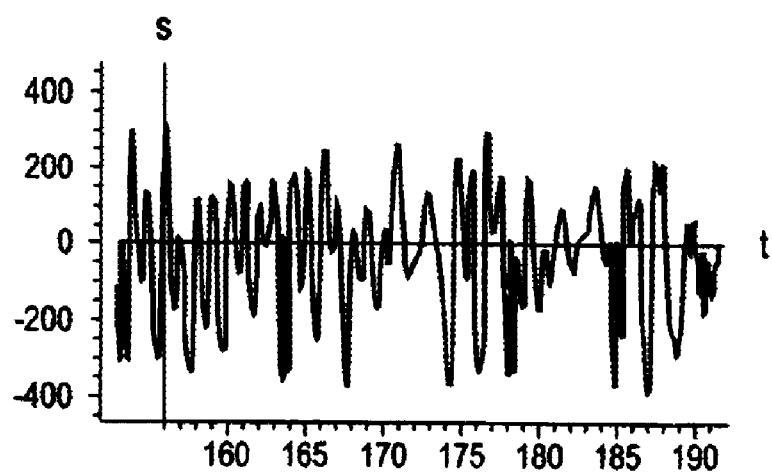

FIG. 6 illustrates the effect of noise on the rescaling procedure. FIG. 6a was derived from FIG. 4d by adding white noise, chosen from a uniform distribution of amplitudes between −200 and +200. This causes a pronounced hiss to be superposed on the word "door" when the entire 334 ms sound exemplified by FIG. 6a is played. FIG. 6b is the s representation, derived by rescaling FIG. 6a with $\Delta T=10$ ms. Comparison of FIGS. 6b, 4e, and 4b shows that the noise has caused some degradation of the invariance of the s representation. This is expected because additive noise ruins the invertibility of the transformations relating FIGS. 6a, 4d, and 4a, thereby violating the proof of the invariance of S in Section II.A. The noise sensitivity of the s representation can be decreased by increasing $\Delta T$, because this increases the number of contributions to the right side of Eq.(3), which tends to "average out" the effects of noise. However, such an increase in $\Delta T$ means that more time is required for the rescaling process to adapt to a sudden change in the signal transformation.

V.A.2. Spectra of Synthetic Speech-like Sounds

In the previous Section, a specific embodiment of the invention was demonstrated by applying it to time-domain human speech waveforms that were related to one another by invertible transformations. However, these transformations incorporated the effects of a relatively small range of speakers' "voices" and listeners' "ears". For example, signals related by such transformations did not mimic voices with a significant range of pitches. A much wider range of speech signals can be created by transforming a sound's short-term Fourier spectra with multidimensional non-linear transformations. In this Section, we demonstrate that, if the speech spectra produced by different speakers and/or detected by different listeners are related by such transformations, they will have the same rescaled representation. For computational simplicity, we consider synthetic speech-like signals that are generated by a "glottis" and "vocal tract" controlled by a single degree of freedom. These signals mimic the "one-dimensional speech" produced by multiple muscles whose motion is determined by the value of a single time-dependent parameter. The same approach can be applied to human speech signals, which are produced by a vocal apparatus with multiple degrees of freedom, by utilizing the specific embodiments of the invention described in Sections II.B, III, and IV.

The "ID speech" signals were generated by a standard linear prediction (LP) model. In other words, the signals' short-term Fourier spectra were equal to the product of an "all pole" transfer function and a glottal excitation function. The transfer function had six poles: two real poles and four complex poles (forming two complex conjugate pairs). The resulting speech spectra depended on the values of eight real quantities, six that described the positions of the poles and two that described the pitch and amplitude ("gain") of the glottal excitation. Each of these quantities was a function of a single parameter (g), which itself depended on time. These eight functions described the nature of the speaker's "voice", in the sense that they defined the ID manifold of all spectra that the speaker could produce as g ranged over all of its possible values. The actual sound produced at any given time was determined by these eight functions, together with the value of g(t). The latter function defined the "articulatory gesture" of the speaker, in the sense that it determined how the speaker's vocal apparatus was configured at each time. In a musical analogy, the g-dependent functions of the LP model would describe the range of possible states of a musical instrument played with one finger, and the function g(t) would describe the motions of the musician's finger as it configures the instrument during a particular tune. In these examples, we considered speakers who produced "voiced" speech sounds that were driven by regular glottal impulses. However, it is straightforward to apply the same methods to "unvoiced" speech sounds that are driven by noise-like glottal excitation functions. The pitch of the first speaker's voice was taken to be constant and equal to 200 Hz.

Figure 7A:
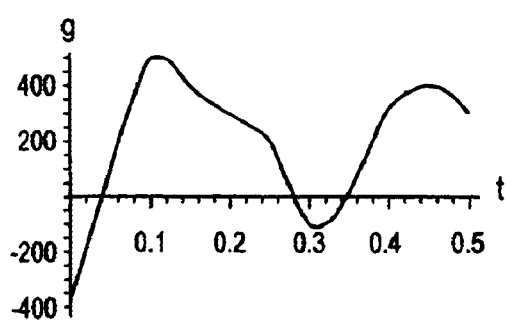
FIGS. 7a–d are pictorial illustrations of the results obtained with speaker #1 and listener #1.
Figure 7B:
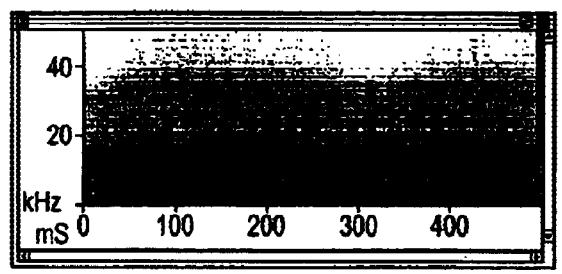
Figure 7C:
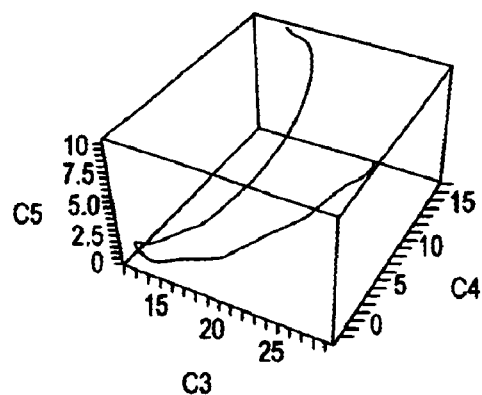
Figure 7D:
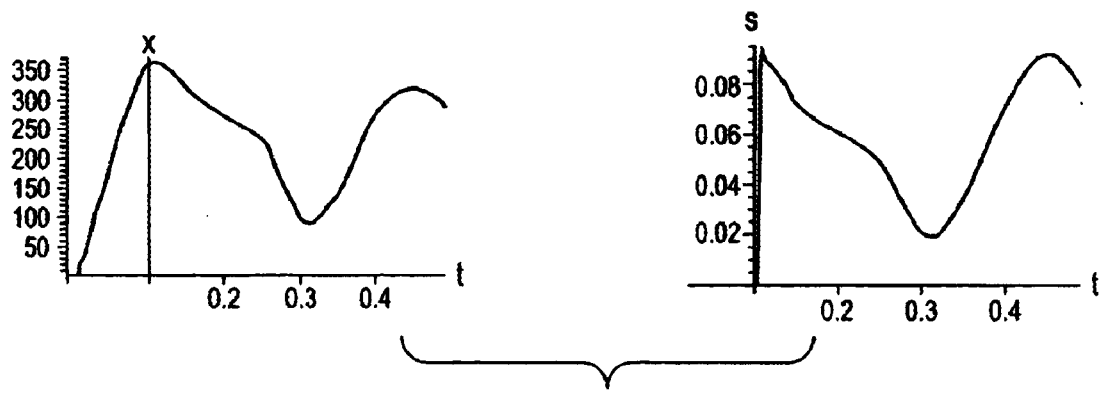

The first listener's "ears" were described by his/her method of detecting and processing the time domain speech signals. The above-described signals were digitized at 10 kHz, and then short-term Fourier spectra were produced from the signals in a 10 ms Hamming window that was advanced in increments of 5 ms. FIG. 7b shows the spectrogram that resulted from the signal generated by the first speaker's "voice", when it went through the series of configurations described by the "gesture" function in FIG. 7a. The spectrum at each time point was parameterized by cepstral coefficients, which were generated by the discrete cosine transformation (DCT) of the log of the spectral magnitude, after the spectral magnitude had been averaged in equally spaced 600 Hz bins. The listener described in this paragraph (listener #1) was assumed to detect only the third, fourth, and fifth cepstral coefficients of each spectrum. The cepstral coefficients from each short-term spectrum defined a single point in this three-dimensional space. Each of these points fell on a curve defined by the cepstral coefficients corresponding to all possible configurations of the speaker's vocal apparatus (i.e., all possible values of g). The precise shape of this curve depended on the nature of the speaker's voice (specified by the g-dependence of the speech model's poles and other parameters). FIG. 7c shows the configuration of this curve for the voice of the speaker described in the previous paragraph. A convenient coordinate system (denoted by x) was established on this curve by projecting each of its points onto a connected array of chords that hugged the curve. The "raw" sensor signal for a specific utterance consisted of the temporal sequence of coordinates x(t) that were generated as the cepstrum traversed that curve. Because the spectrogram in FIG. 7b was generated by an oscillatory g(t), previously generated spectra (and cepstra) were revisited from time to time, and the corresponding cepstral coefficients moved back and forth along the curve in FIG. 7c. The left side of FIG. 7d shows the oscillatory sensory signal x(t) that was generated in this way.

Figure 8A:
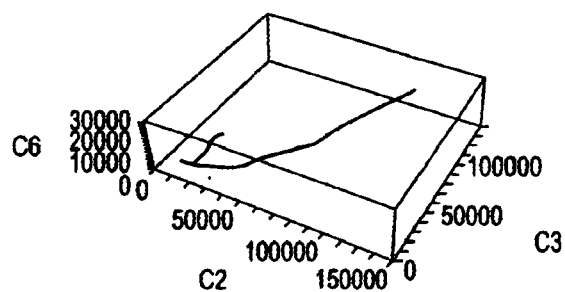
FIGS. 8a–b are pictorial illustrations of the results obtained with speaker #1 and listener #2.
Figure 8B:
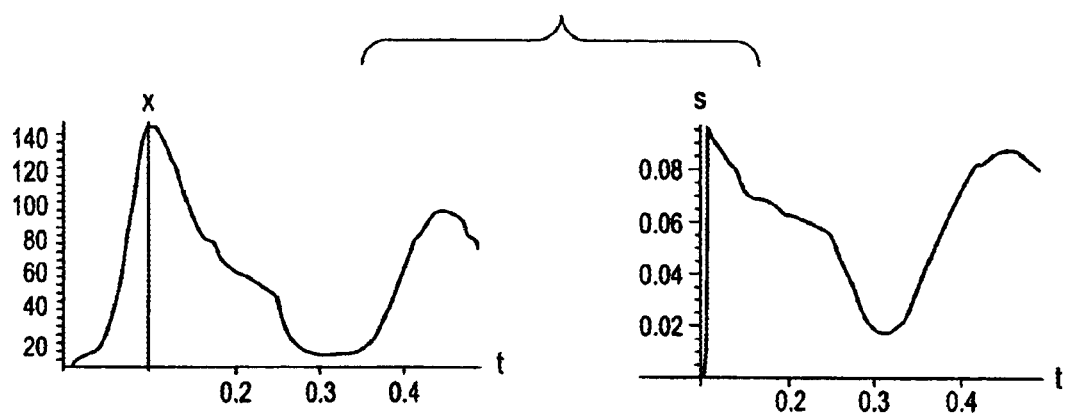

The ears of a second listener were modeled in the following manner. The second listener was assumed to compute the short-term Fourier spectra of the time domain signal, as described above. However, instead of calculating the cepstrum of each spectrum, the second listener was assumed to compute the DCT of its magnitude (not its log magnitude), after it (the spectral magnitude) had been averaged in equally spaced 600 Hz bins. This listener detected only the second, third, and sixth of these DCT coefficients. The voice of the above-described speaker was characterized by the curve (FIG. 8a) defined by the spectral DCT coefficients of all possible sounds that could be generated by the vocal apparatus (i.e., all possible values of g). As before, a convenient coordinate system (x') was established on this curve by projecting each of its points onto a connected array of chords that hugged the curve. The left side of FIG. 8b is the sensor signal x'(t) that was induced in listener #2 by the sound in FIG. 7b. Note that the x and x' coordinate systems could bear any relationships to the curves in FIGS. 7c and 8a, respectively, and need not have any definite or known relationship to one another, except that x=0 and x'=0 must correspond to the same sound (e.g., the same value of g). In this example, this condition was satisfied by defining the x and x' coordinate systems so that x=x'=0 corresponded to the first short-term spectrum in the utterance in FIG. 7b. Alternatively, this could be arranged by having both listeners hear any single sound produced by speaker #1 and agree to originate their coordinate systems at the corresponding point on the speaker's "voice" curve; this is analogous to having a choir leader play a pitch pipe in order to establish a common origin of the musical scale among the singers. Finally, the raw sensory signal in each listener, x(t) and x'(t), was processed by rescaling with ΔT=500 ms. The results are shown on the right sides of FIGS. 7d and 8b, respectively. Notice the similarity between these s representations despite the differences between the sensor signals, x(t) and x'(t), from which they were created. This means that the two listeners created the same rescaled representation of the utterance, despite the dramatic differences in their "ear" mechanisms (FIGS. 7c and 8a). The rescaled representations were the same because the sensor signals, x(t) and x'(t), were related to one another by an invertible transformation that preserved the null amplitude. This was true because each listener was sensitive to the spectral changes produced by all changes in g, and, therefore, each sensor signal was invertibly related to g(t). Furthermore, for the same reason, any other gesture function g̃(t) that is invertibly related to the function in FIG. 7a will generate an utterance with the rescaled representation in the right panel of FIG. 7d. In other words, the utterances that are produced by these "different" gesture functions will be internally represented as the same message uttered in two different tones of voice. Finally, notice that the rescaled representation of $g_1(t)\equiv g(t)-g(0)$ is identical to the rescaled representations of x(t) and x'(t). This is expected because $g_1(t)$ is invertibly related to each of these sensor signals in a way that transforms $g_1=0$ into x=x'=0. This means that the speaker creates identical internal representations of both the spoken sound and the "motor" signal that controls the configuration of the vocal apparatus.

Figure 9A:
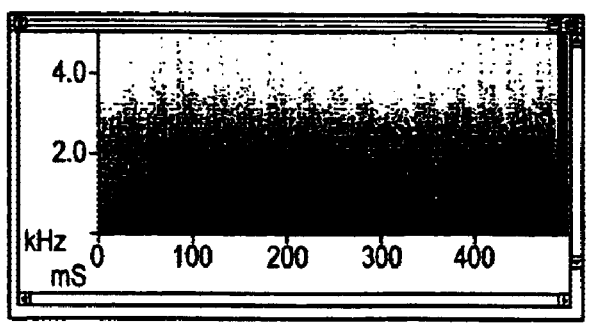
FIGS. 9a–c are pictorial illustrations of the results obtained with speaker #2 and listener #2.
Figure 9B:
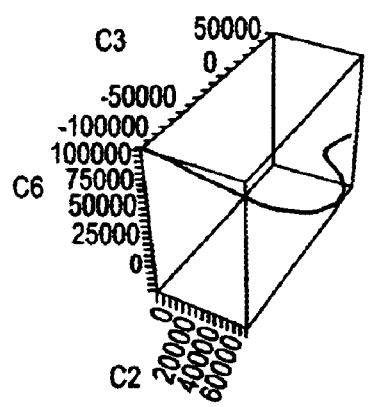
Figure 9C:
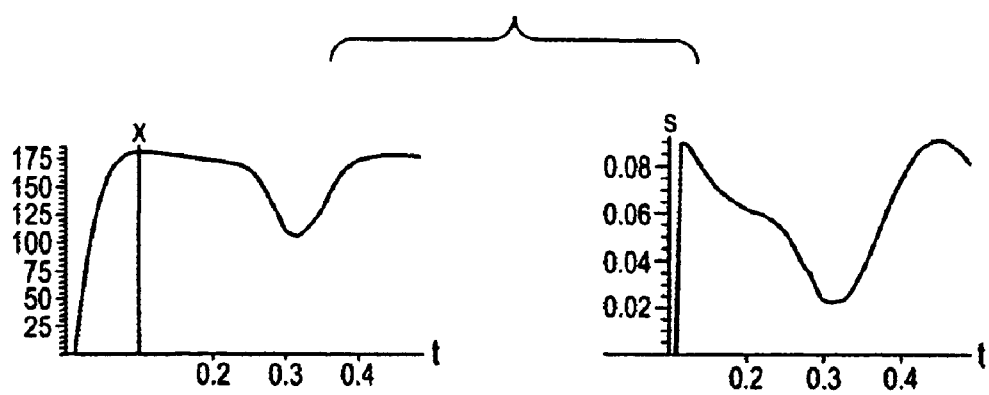

The voice of a second speaker was modeled by choosing different g-dependent functions for the 8 quantities in the LP model of the vocal apparatus. Specifically, the glottal pitch was set equal to 125 Hz, and the poles of the vocal tract transfer function were chosen to be significantly different functions of g than for the first voice. FIG. 9a shows the spectrogram produced by this second "voice" when it made the "articulatory gesture" in FIG. 7a. FIG. 9b is the curve in DCT coefficient space induced in listener #2 by this voice, when it produced all possible spectra (i.e., spectra corresponding to all possible values of g). FIGS. 8a and 9b show that listener #2 characterized the first and second voices by dramatically different curves in DCT coefficient space. The left side of FIG. 9c depicts the sensor signal x'(t) induced in listener #2 by the utterance in FIG. 9a. As before, the origin of the x' coordinate system along the curve in FIG. 9b was chosen to correspond to the first sound spectrum emitted by the speaker. Finally, the right side of FIG. 9c is the rescaled representation of this raw sensor signal. Notice that there is no significant difference between the rescaled representations in FIGS. 9c and 8b, despite the fact that they were derived from the utterances of different voices and corresponded to raw sensor signals from different spectrograms (FIGS. 9a and 7b). This is because these sensor signals are related by an invertible transformation. Such a transformation exists because each sensor signal is invertibly related to the same gesture function (i.e., g(t) in FIG. 7a).

V.B. Multidimensional Sensor State Manifolds Having Local Directionality

Figure 10A:
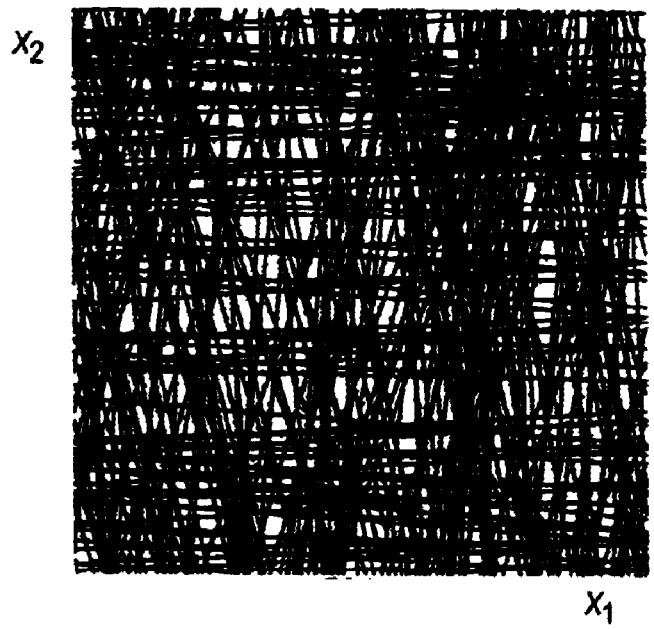
FIG. 10a is a pictorial illustration of the simulated trajectory of recently encountered sensor states x(t). The speed of traversal of each trajectory segment is indicated by the dots, which are separated by equal time intervals. The nearly horizontal and vertical segments are traversed in the left-to-right and bottom-to-top directions, respectively. The graph depicts the range $-5 \leq x_k \leq 5$.
Figure 10B:
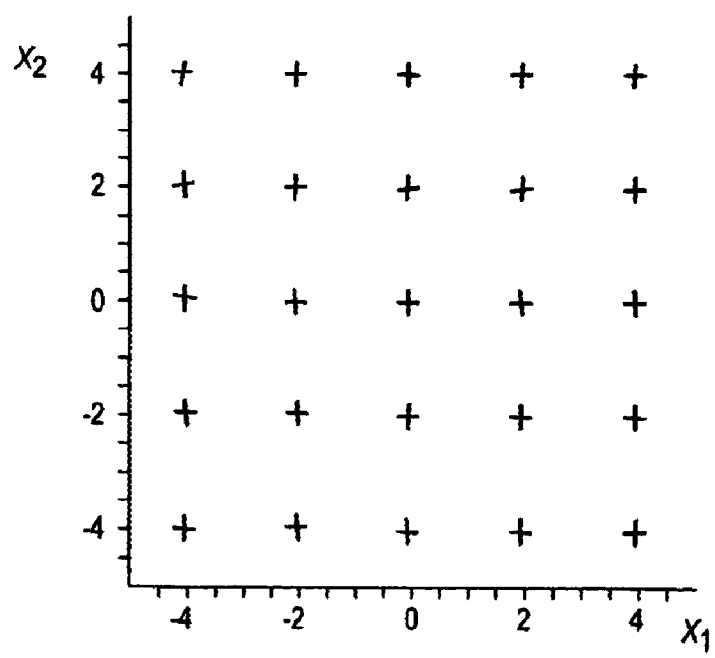
FIG. 10b is a pictorial illustration of the local preferred vectors $h_a$ that were derived from the data in FIG. 10a by means of the method and apparatus in Section II.B. The nearly horizontal and vertical lines denote vectors that are oriented to the right and upward, respectively.
Figure 10C:
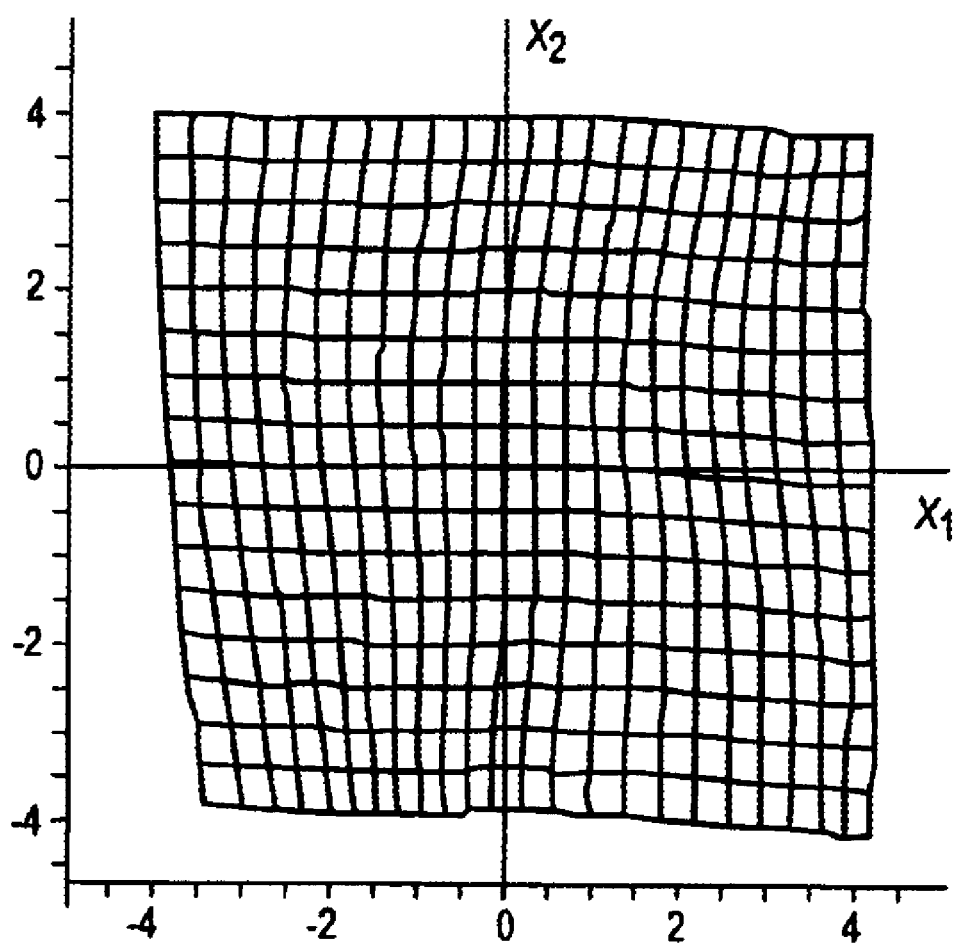
FIG. 10c is a pictorial illustration of the level sets of s(x), which shows the intrinsic coordinate system or scale derived by applying the method and apparatus in Section II.B to the data in FIG. 10a. The nearly vertical curves are loci of constant $s_1$ for evenly spaced values between –11 (left) and 12 (right); the nearly horizontal curves are loci of constant $s_2$ for evenly spaced values between –8 (bottom) and 8 (top)
Figure 11:
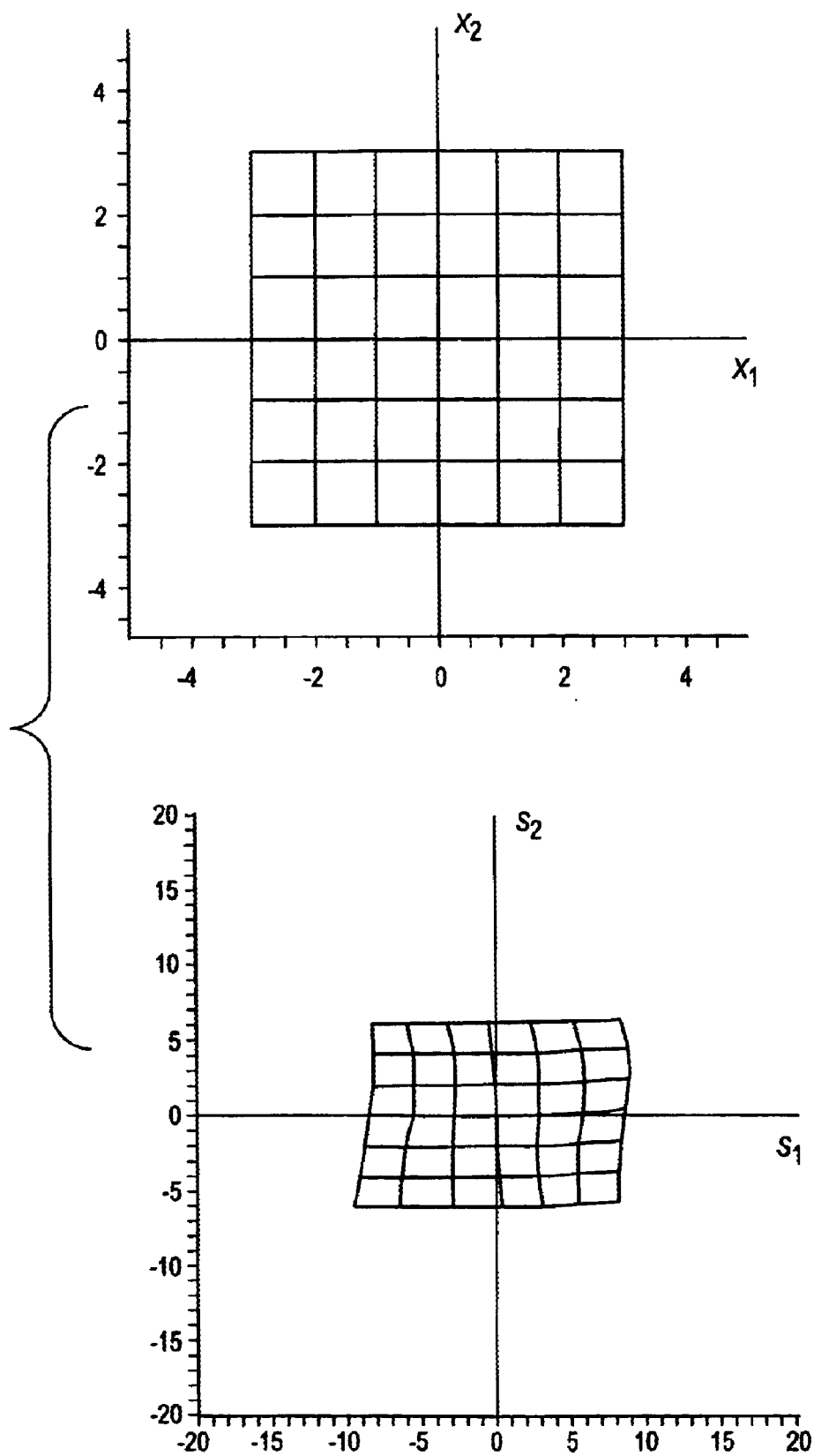
FIG. 11 is a pictorial illustration of the coordinate-independent representation (right figure) of a grid-like array of sensor states (left figure), obtained by using FIG. 10c to rescale those sensor states.

In this section, we demonstrate the specific embodiment of the present invention in Section II.B by applying it to simulated data on a two-dimensional sensor state manifold. Let $x=(x_1 x_2)$ represent the state of the device's sensor. For example, these numbers might be the coordinates of a specific feature being tracked in a time series of digital images, or they could be the amplitudes or frequencies of peaks in the short-term Fourier spectrum of an audio signal. Suppose that FIG. 10a represents the trajectories of the sensor states that were previously encountered by the system. Notice that these lines tend to be oriented in nearly horizontal or vertical directions, thereby endowing the manifold with directionality at each point. We used these data to compute the local vectors $h_a$ on a uniform grid of sample points that was centered on the origin and had spacing equal to two units. To do this, we considered a small neighborhood of each sample point, and the time derivative of each trajectory segment traversing the neighborhood was computed at equal time intervals. Then, Eqs.(9–13) with p=1 were applied in order to derive local vectors from the collection of time derivatives at each sample point. The resulting vectors $h_a$, shown in FIG. 10b, were then interpolated in order to estimate the vectors at intervening points. As expected, these vectors reflect the horizontal and vertical orientations of the trajectories from which they were derived. Finally, Eqs.(1–2) were applied to these $h_a$ in order to compute the coordinate-independent representation $s_a$ of each sensor state on the manifold, relative to the reference state which was chosen to be $x_0=(0,0)$. The result is shown in FIG. 10c, which depicts the level sets of the scale function $s_a(x)$ that is intrinsic to the sensor state history in FIG. 10a. FIG. 11 shows how an "image" of sensor states in the x coordinate system is represented in the s coordinate system.

Figure 12A:
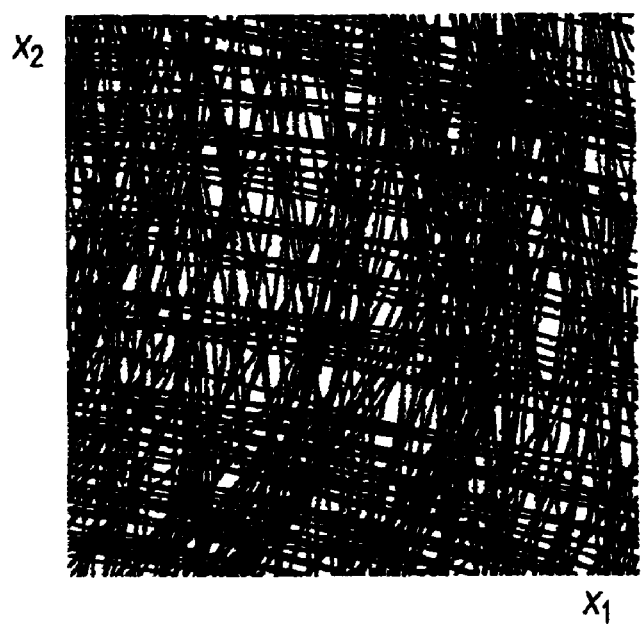
FIG. 12a is a pictorial illustration of the simulated trajectory of recently encountered sensor states x(t) that are related to those in FIG. 10a by the coordinate transformation in Eq.(25). The speed of traversal of each trajectory segment is indicated by the dots, which are separated by equal time intervals. The nearly horizontal and vertical segments are traversed in the left-to-right and bottom-to-top directions, respectively. The graph depicts the range $-5 \leq x_k \leq 5$.

Next, we considered what would have happened if the same device had "experienced" sensor states shown in FIG. 12a. These trajectories are related to those in FIG. 10a by the following non-linear transformation:

$$x \to 0.1+x_1+0.1x_2+0.01x_1^2-0.02x_2^2-0.01x_1x_2$$
$$x_2 \to 0.2-0.2x_1+x_2-0.01x_1^2+0.02x_2^2+0.01x_1x_2 \quad \text{(Eq. 25)}$$

Figure 12B:
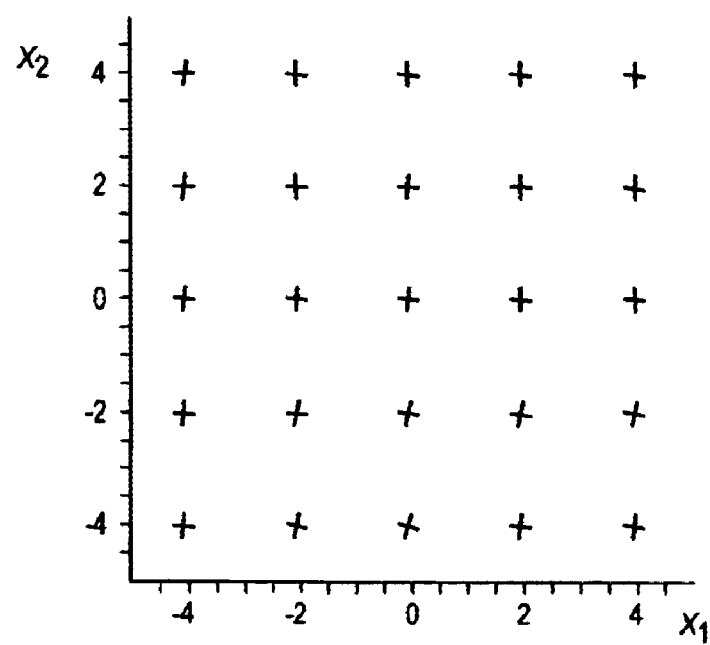
FIG. 12b is a pictorial illustration of the local preferred vectors $h_a$ that were derived from the data in FIG. 12a by means of the method in Section II.B. The nearly horizontal and vertical lines denote vectors that are oriented to the right and upward, respectively.
Figure 12C:
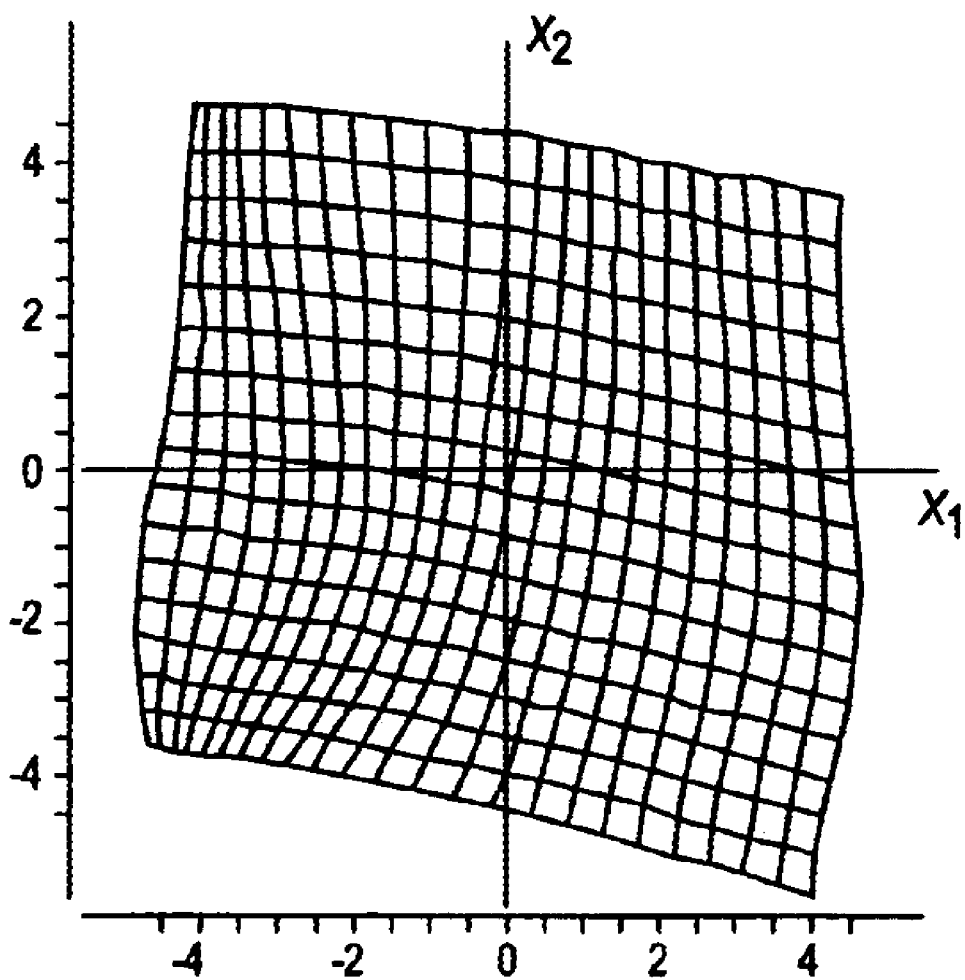
FIG. 12c is a pictorial illustration of the level sets of s(x), which shows the intrinsic coordinate system or scale that was derived by applying the method and apparatus in Section II.B to the data in FIG. 12a. The vertical curves are loci of constant $s_1$ for evenly spaced values between –12 (left) and 11 (right); the horizontal curves are loci of constant $s_2$ for evenly spaced values between –9 (bottom) and 7 (top)
Figure 13:
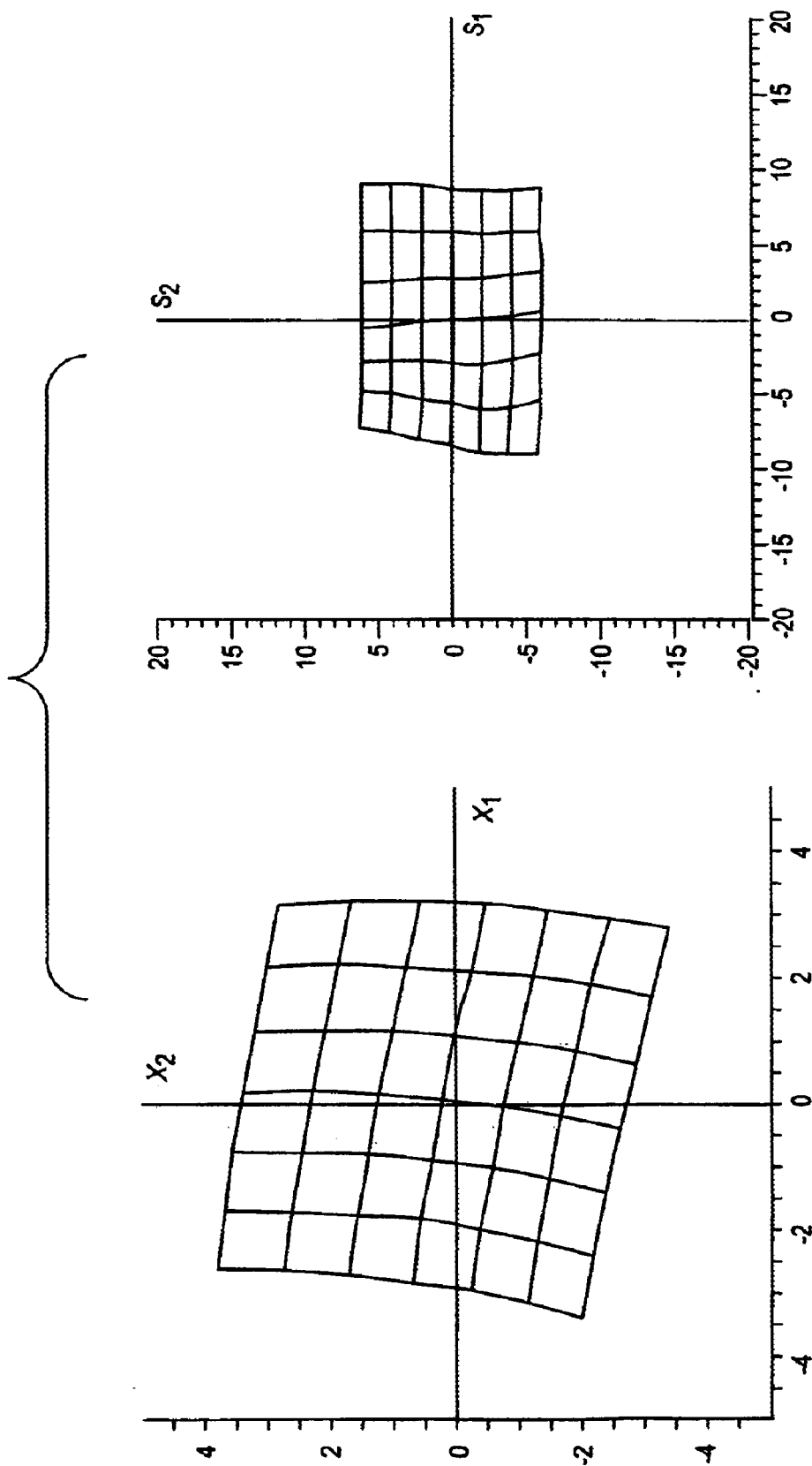
FIG. 13 is a pictorial illustration of the coordinate-independent representation (right figure) of array of sensor states (left figure), obtained by rescaling the sensor states by means of FIG. 12c. The panel on the left was created by subjecting the corresponding left panel in FIG. 11 to the coordinate transformation in Eq.(25). Notice that the right panel is nearly identical to the one in FIG. 11, thereby confirming the fact that these representations are invariant under the coordinate transformation.

For example, suppose that the sensor state is the location of a feature in a digital image. Equation (25) could represent the way the sensor states are transformed by a distortion of the optical/electronic path within the camera or by a distortion of the surface on which the camera is focused (e.g., distortion of a printed page). The procedure outlined above was used to compute the local vectors on a uniform grid of sample points. FIG. 12b shows the resulting vectors, which are oriented along the principal directions apparent in FIG. 12a. Next, interpolation was used to estimate the $h_a$ at intervening points, and Eqs.(1–2) were used to compute the coordinate-independent representation sa of each sensor state on the manifold, relative to the reference sensor state which was chosen to be $x_0=(0.1,0.2)$. Notice that we have assumed prior knowledge of the transformed position of the reference sensor state. In other words, we have assumed that we have the prior knowledge necessary to identify this state both before and after the onset of the process, which remaps the sensor states. The result of this calculation is shown in FIG. 12c, which depicts the level sets of the functions $s_a(x)$, the scale function inherent to the sensor state data in FIG. 12a. These functions were used to compute the $s_a$ representation of the transformed version of the "image" in the left panel of FIG. 11. The transformed image and its $s_a$ representation are shown in FIG. 13. Comparison of FIG. 11 and FIG. 13 shows that the $s_a$ representations of the untransformed and transformed image are nearly identical. Thus, the invented method and apparatus make it possible to maintain invariant representations of stimuli in the presence of unknown invertible transformations of sensor states, such as the one in Eq.(25). The tiny discrepancies between FIG. 11 and FIG. 13 can be attributed to errors in the interpolation of the $h_a$, which is due to the coarseness of the grid on which $h_a$ was sampled. This error can be reduced if the distance between sample points can be decreased. This is possible if the device is allowed to experience a denser set of sensor states (i.e., more trajectory segments than shown in FIGS. 10a and 12a) so that even tiny neighborhoods contain enough data to compute the $h_a$.

V.C. Multidimensional Sensor State Manifolds Supporting Parallel Transport

Figure 14A:
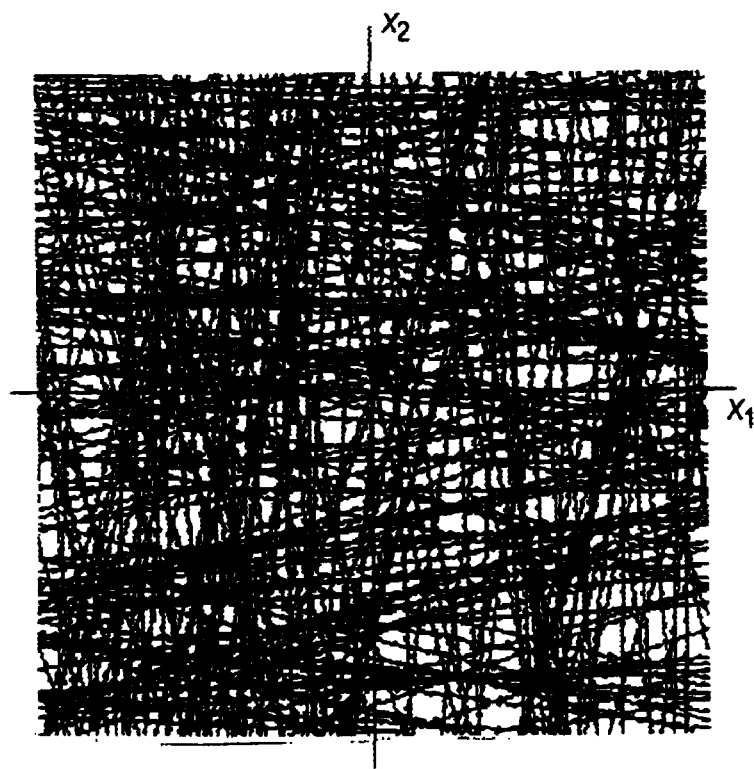
FIG. 14a is a pictorial illustration of the simulated trajectory of recently encountered sensor states x(t). The speed of traversal of each trajectory segment is indicated by the dots, which are separated by equal time intervals. The nearly horizontal and vertical segments are traversed in the left-to-right and bottom-to-top directions, respectively. The graph depicts the range $-10 \leq x_k \leq 10$.

In this section, we demonstrate the specific embodiment of the present invention in Section III by applying it to simulated data on a two-dimensional sensor state manifold. Let $x=(x_1,x_2)$ represent the state of the device's sensor. For example, these numbers might be the coordinates of a specific feature being tracked in digital images, or they could be the amplitudes and/or frequencies of peaks in the short-term Fourier spectrum of a microphone's output signal. Suppose that FIG. 14a represents the trajectories of the sensor states that were previously encountered by the system. Notice that these happen to be straight lines that are traversed at constant speed. Equations 18–19 were used to compute the affine connection on a uniform grid of sample points that was centered on the origin and had spacing equal to two units. To do this, we considered a small square neighborhood of each sample point with dimensions equal to 1.6 units. Each trajectory segment that traversed the neighborhood was divided into line elements traversed in equal time intervals. Next, we considered any three pairs of such line elements, where each pair consisted of two adjacent line elements on a trajectory segment. Then, we asked if there was a unique affine connection $\hat{\Gamma}_{lm}^{k}$ that parallel transported each line element into the other line element of the same pair. The affine connection at the sample point was set equal to the average of the quantities $\hat{\Gamma}_{lm}^{k}$ that were derived for all possible triplets of paired line elements in the neighborhood. Triplets of paired line elements for which there was no unique solution (e.g., multiple solutions or no solution) did not contribute to this average. In this way, we derived an affine connection for which the neighboring trajectory segments were geodesic in an average sense. In this particular case, all components of the resulting affine connection equaled zero; i.e., the x coordinate system is a geodesic coordinate system of a flat manifold. This result is expected because a vanishing affine connection is the only one that parallel transports equally long line elements of straight lines into one another.

The reference state was chosen to be the origin of the x coordinate system ($x_0=0$), and the method in Section II.B (Eq.(13)) was used to compute local vectors from the directionality of nearby trajectory segments. Specifically, we considered the trajectory segments passing through a small square neighborhood of $x_0$ with dimensions equal to 1.0. Local vectors $\hat{h}_1$ were found by calculating the time derivatives along these trajectory segments at the equally spaced time points shown in FIG. 14a (Eq.(9)). We then looked at all possible ways of partitioning this collection of vectors into two subsets and found the partition with the minimal value of E (Eq.(12) with p=1). Finally, the average vector in each of these partitions was computed in order to find the principal vectors $h_c$ at $x_0$. As explained in Section II.B, these are the directions in which the local trajectory segments tend to be oriented. In this example, these vectors were:

$$h_1(0.488,-0.013) \text{ and } h_2=(0.064,0.482) \qquad \text{(Eq. 26)}$$

This result expresses the fact that the trajectory segments in FIG. 14a tend to be oriented in nearly horizontal and vertical directions.

Figure 14B:
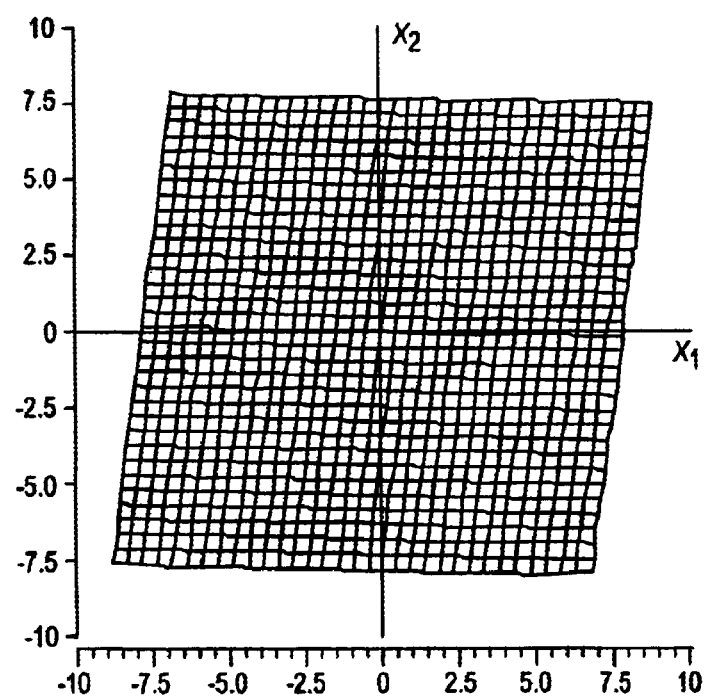
FIG. 14b is a pictorial illustration of the level sets of s(x), which shows the intrinsic coordinate system or scale derived by applying the method and apparatus in Section III to the data in FIG. 14a. The nearly vertical curves are loci of constant $s_1$ for evenly spaced values between –16 (left) and 16 (right); the nearly horizontal curves are loci of constant $s_2$ for evenly spaced values between –16 (bottom) and 16 (top)
Figure 15:
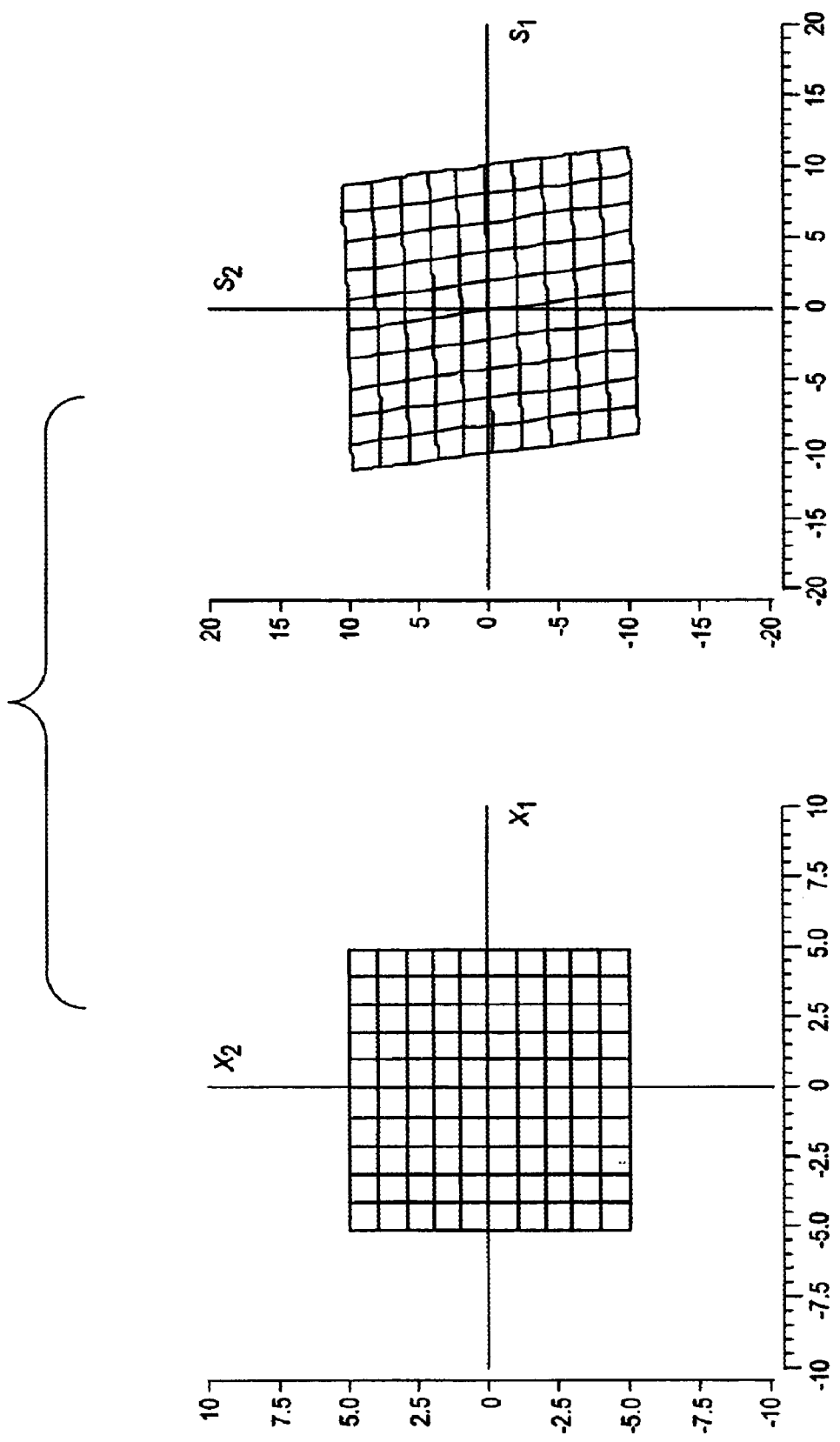
FIG. 15 is a pictorial illustration of the coordinate-independent representation (right figure) of a grid-like array of sensor states (left figure), obtained by using FIG. 14b to rescale those sensor states.

The affine connection was used to "spread" these vectors throughout the manifold by parallel transporting them along type 1 and type 2 geodesics. Then, Eqs.(1–2) were used to compute the values of s that comprise the coordinate-independent representation of each sensor state x. The results are shown in FIG. 14b, which depicts the level sets of s(x). Because of the flat nature of this particular manifold, the s coordinate system is related to the x coordinate system by an affine transformation. FIG. 15 shows how an "image" of sensor states in the x coordinate system is represented in the s coordinate system.

Figure 16A:
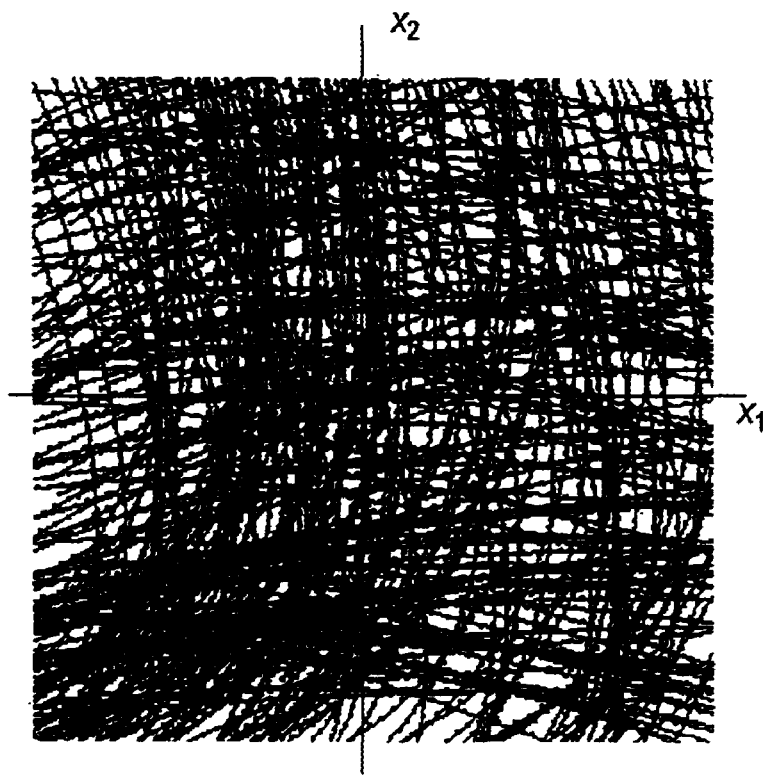
FIG. 16a is a pictorial illustration of the simulated trajectory of recently encountered sensor states x(t) that are related to those in FIG. 14a by the coordinate transformation in Eq.(27). The speed of traversal of each trajectory segment is indicated by the dots, which are separated by equal time intervals. The nearly horizontal and vertical segments are traversed in the left-to-right and bottom-to-top directions, respectively. The graph depicts the range $-10 \leq x_k \leq 10$.

Next, we considered what would have happened if the same device had "experienced" sensor states shown in FIG. 16a. These trajectories are related to those in FIG. 14a by the following non-linear transformation:

$$x_1 \rightarrow 2.5+x_1+0.01x_1^2-0.02x_2^2-0.01x_1x_2$$
$$x_2 \rightarrow x_2-0.01x_1^2+0.02x_2^2+0.01x_1x_2 \qquad \text{(Eq. 27)}$$

For example, suppose that x is the location of a feature in a digital image. Equation (27) could represent the way the sensor states are transformed by a distortion of the optical/electronic path within the camera or by a distortion of the surface on which the camera is focused (e.g., distortion of a printed page). The exact same procedure as outlined above was used to compute the affine connection on a uniform grid of sample points. The resulting affine connection was non-vanishing at each sampled point, and smooth interpolation was used to estimate its values at intervening points. Next, the above-described procedure was used to compute the principal directions of the trajectories at the reference point (2.5, 0). Notice that we have chosen the transformed sensor state that corresponds to the untransformed reference sensor state $x_0=0$. In other words, we have assumed that we have the prior knowledge necessary to identify this reference sensor state in a coordinate-independent fashion. The preferred directions at this point are:

$$h_1=(0.483, 0.025) \text{ and } h_2=(0.058, 0.486) \qquad \text{(Eq. 28)}$$

Figure 16B:
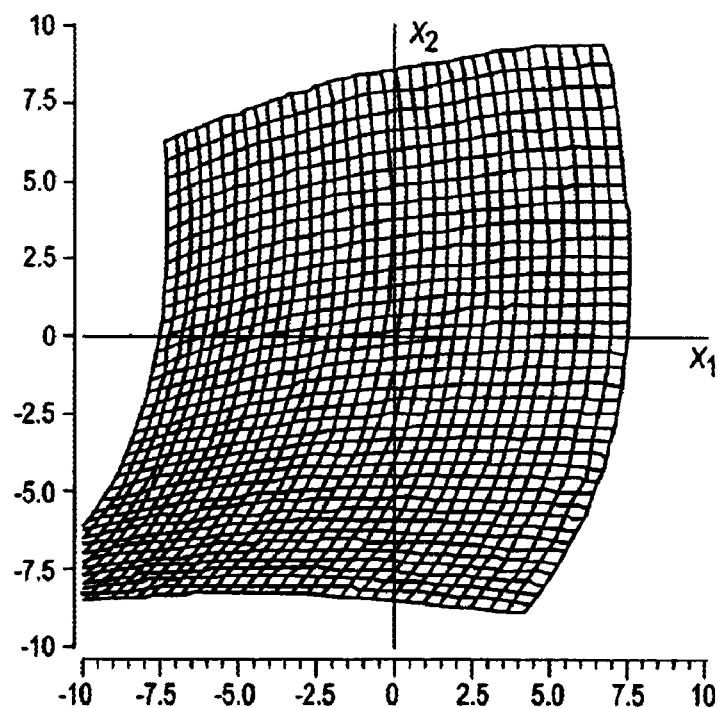
FIG. 16b is a pictorial illustration of the level sets of s(x), which shows the intrinsic coordinate system or scale that was derived by applying the method and apparatus in Section III to the data in FIG. 16a. The vertical curves are loci of constant $s_1$ for evenly spaced values between −24 (left) and 10 (right); the horizontal curves are loci of constant $s_2$ for evenly spaced values between −22 (bottom) and 16 (top)
Figure 17:
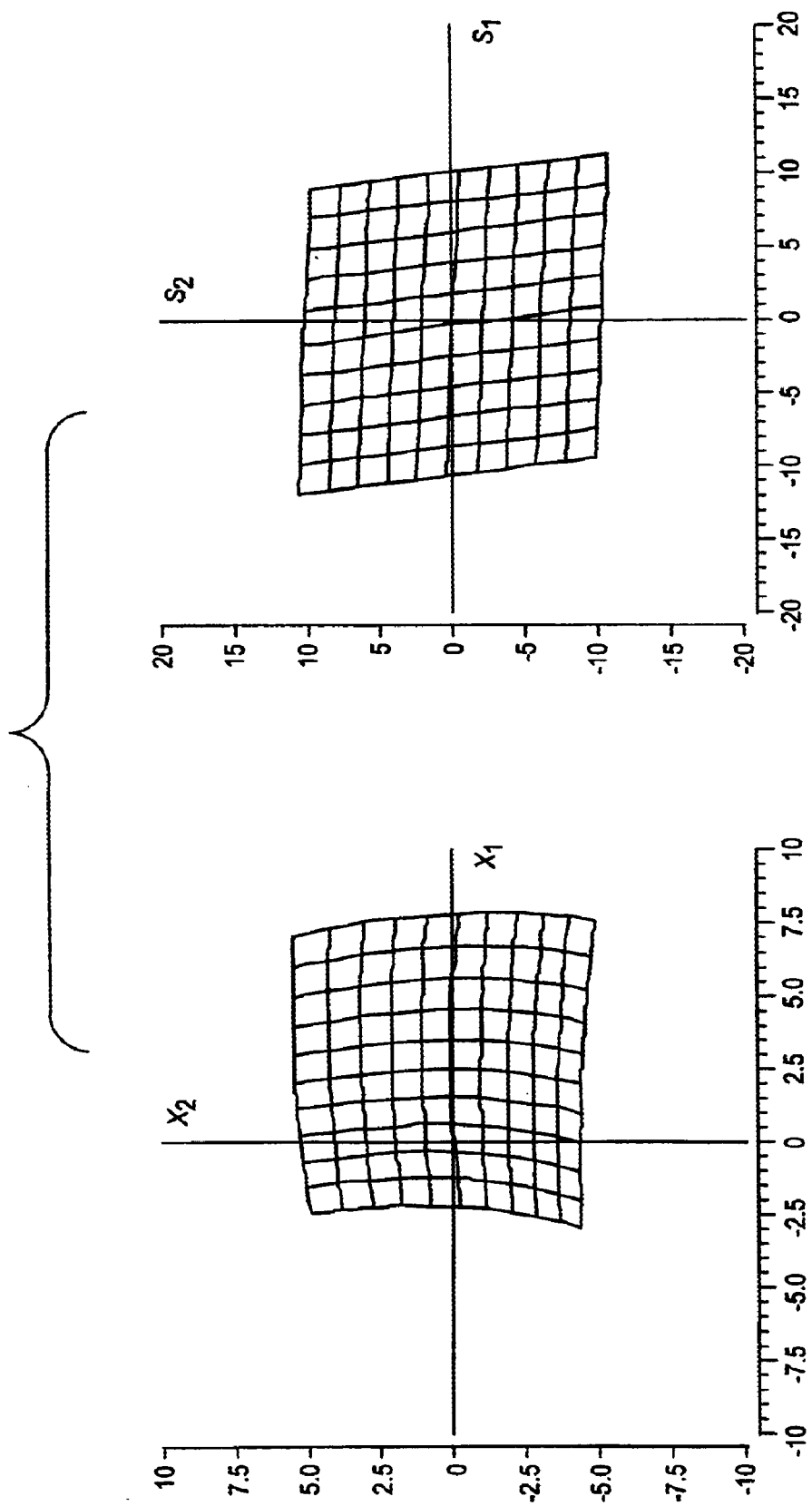
FIG. 17 is a pictorial illustration of the representation (right figure) of an array of sensor states (left figure), obtained by rescaling the sensor states by means of FIG. 16b. The panel on the left was created by subjecting the corresponding left panel in FIG. 15 to the coordinate transformation in Eq.(27). Notice that the right panel is nearly identical to the one in FIG. 15, thereby confirming the fact that these rescaled representations are invariant under the coordinate transformation.

Notice that these vectors are almost the same as those in Eq.(26), as expected, because Eq.(27) implies that $\partial x'_k/\partial x_l = \delta_l^k$ at x=0. The small discrepancies between Eq.(26) and Eq.(28) can be attributed to the finite breadth of the neighborhood of $x_0$ that was used to compute these vectors. The affine connection was used to "spread" these vectors throughout the manifold along type 1 and type 2 geodesics, and the s representation of each point in the manifold was computed by means of Eq.(1–2). FIG. 16b shows the level sets of the resulting function s(x). The function s(x) was used to compute the s representation of the transformed version of the sensor state "image" in the left panel of FIG. 15. The transformed image and its S representation are shown in FIG. 17. Comparison of FIGS. 15 and 17 shows that the s representations of these images are nearly identical. In other words, these representations are invariant with respect to the process that transforms the sensor states by Eq.(27), and, therefore, they are suitable for analysis by a pattern analysis program. The tiny discrepancies between FIGS. 17 and 15 can be attributed to errors in the interpolation of the affine connection, which is due to the coarseness of the grid on which the affine connection was sampled. This error can be reduced if the distance between sample points can be decreased. This is possible if the device is allowed to experience a denser set of sensor states (i.e., more trajectory segments than shown in FIG. 16a) so that even tiny neighborhoods contain enough data to compute the affine connection.

VI. Discussion

The sensor states of a device for detecting stimuli may be invertibly transformed by extraneous physical processes. Examples of such processes include: 1) alterations of the internal characteristics of the device's sensory apparatus, 2) changes in observational conditions that are external to the sensory device and the stimuli, and 3) certain systematic modifications of the presentation of the stimuli themselves. It is clearly advantageous for the device to create an internal representation of each stimulus that is unaffected by these sensor state transformations. Then, it will not be necessary to recalibrate the device's detector (or to retrain its pattern analysis module) in order to account for the effects of these processes. In other words, it is advantageous for a sensory device to encode stimuli in a way that reflects their intrinsic properties and is independent of the above-mentioned extrinsic factors.

As discussed in earlier Sections, certain relationships among a collection of sensor states may be preserved in the presence of such a transformation, even though each sensor state is individually transformed. It is mathematically possible to characterize these relationships and to use them to generate stimulus representations that will be invariant under such sensor state transformations. This can be done by exploiting the "natural" intrinsic structure of the collection of sensor states encountered during a chosen time period. Specifically, such a sensor state time series may have a local internal structure that makes it possible to determine vectors $h_a$ at each point in the collection. In essence, these vectors establish local coordinate systems, which are analogous to the global "center-of-mass" coordinate system of a collection of particles (see the Summary of the Invention). If the representation of each sensor state is referred to these local coordinate systems of the collection, it will be invariant under any local transformations of sensor states. Therefore, such representations will be not be affected by the presence of processes causing such sensor state transformations. This is the basis for one embodiment of the present invention, which includes a non-linear signal processing technique for identifying the "part" of a time-dependent signal that is invariant under signal transformations. This form of the signal is found by rescaling the signal at each time, in a manner that is determined by signal levels in a chosen time interval (e.g., during the most recent time period of length $\Delta T$). The rescaled signal (called its s representation) is unchanged if the original signal time series is subjected to any time-independent invertible transformation.

A specific embodiment of the present invention consists of multiple sensory devices that have different sensors but represent stimuli in the same way. Specifically, any two sensory devices will create identical rescaled representations of an evolving stimulus as long as there is an invertible mapping between their sensor state time series. The latter condition will be satisfied by a wide variety of sensory devices. Specifically, consider any sensory device that is designed to sense a stimulus that has d degrees of freedom; i.e., a stimulus whose configurations define a d-dimensional manifold. Furthermore, assume that there is a time-independent invertible mapping between these stimulus configurations and a d-dimensional manifold of sensor states in the device. This is a weak assumption, which simply means that the device is sensitive to all degrees of freedom of the stimulus. It follows that there will be a time-independent invertible mapping between the sensor state time series of any two such devices as they both observe the same evolving stimulus. Therefore, the rescaled representations of those evolving sensor states will be identical and can be subjected to the same pattern analysis. Notice that, because the sensor state time series of such a device is invertibly related to the time series of evolving stimulus configurations, it has the same rescaled representation as the stimulus configuration time series. In this sense, such a device encodes "inner" properties of the time series of the stimulus configurations themselves; i.e., properties that are independent of the nature of the observing device or the conditions of observation. As an illustration, consider a computer vision device that is designed to detect the expressions of a particular face, and suppose that those expressions form a 2D manifold. For instance, this would be the case if each facial expression is defined by the configuration of the mouth and eyes and if these are controlled by two parameters. An example of such a device is a computer vision system V in which the sensor state x consists of a particular pair of 2D Fourier components of the face. As long as each change of facial expression causes a change in this pair of Fourier components, there will be a time-independent invertible mapping between x and the manifold of facial expressions (i.e., between x and the two parameters controlling the expressions). Now, consider another computer vision system V', which computes the coefficients of 16 particular Bessel functions in the 2D Bessel expansion of the facial image. Each face will correspond to a point in a 16-D space of Bessel coefficients, and all possible facial expressions will lie on a 2D subspace of that space. Now, suppose that the sensory state x' of system V' consists of the coordinates of each face in some convenient coordinate system on this 2D subspace. As long as each change of facial expression causes a change in the set of 16 Bessel coefficients, there will be a time-independent invertible mapping between x' and the manifold of facial expressions. It follows that there will be a time-independent invertible mapping between the sensor state x of system V and the sensor state x' of system V', as they both observe any time series of facial expressions. Therefore, these two vision systems will derive identical rescaled representations of each face, despite the dramatic difference in their detectors. More generally, any two sensory devices, which are built with completely different numbers and types of detectors, will "see" the world in the same way, as long as each device is sensitive to the same degrees of freedom of the stimulus and as long as each device rescales its detectors' output. Furthermore, any such device will produce identical rescaled representations of two different stimuli (e.g., S and S') whose time-dependent configurations are related by a time-independent invertible mapping. To see this, recall that there is a time-independent invertible mapping between the time series of S configurations and the time series of sensor states x(t) produced in the device by S. Likewise, there is an invertible mapping between the time series of S configurations and the time series of sensor states x'(t) when the device observes S. It follows that there is a time-independent invertible mapping between x(t) and x'(t), and, therefore, these time series have identical rescaled representations. As an example, suppose that one of above-described computer vision systems (e.g., V) was exposed to a time series of expressions of face F, and, on another occasion, it was exposed to a time series of expressions of a different face F'. Further, suppose that the two time series depicted similar sequences of facial expressions in the sense that there was a time-independent invertible mapping between the two parameters controlling F and the two analogous parameters controlling F'. It follows that the vision system would produce identical rescaled representations of the F and F' time series.

Note that there is more than one way to interpret the fact that two stimulus time series produce different time series of sensor states, which lead to the same time series of rescaled representations. For example, suppose the above-described vision system V observes two evolving facial stimuli, F and F', that have identical time series of rescaled representations but different time series of raw sensor states, x(t) and x'(t). Without additional information, the device may not be able to tell whether the differences between the two sensor state time series were due to: 1) physical differences in the stimuli themselves; 2) the presence of a process that affected the device's detector or the "channel" between it and the face. For example, the above-described computer vision device may not be able to determine if x(t) and x'(t) were produced by: 1) two different faces that evolved through analogous facial expressions; 2) the same face that underwent the same sequence of expressions, first in the absence and then in the presence of some transformative process (e.g., the absence and presence of an image-warping lens). Similarly, suppose the device recorded two sensor state time series that differed by a scale factor but had identical rescaled representations. The device could attribute the sensor state differences to: 1) a change in the complexion of the observed face; 2) a change in the gain of the device's camera or a change in the illumination of the face. Of course, humans can suffer from illusions due to similar confusions. Like a human, the device could distinguish between these possibilities only if it had additional information about the likelihood of various processes that might cause the transformation between the observed sensor states or if it was able to observe additional degrees of freedom of the stimulus.

In the above discussion it was assumed that the sensor states in a given time series were remapped by a time-independent invertible transformation. Now, consider the effects of the sudden onset of a process that invertibly transforms the sensor states. Suppose that each sensor state is represented in terms of the intrinsic properties of the collection of sensor states encountered in the most recent $\Delta T$ time units. After the onset of the transformative process, there will be a transitional period of length $\Delta T$, during which the device's stimulus representations will not be the same as those derived from the corresponding time series of untransformed sensor states. This is because these representations are referred to a mixture of transformed and untransformed sensor states. However, once the sensor state "database" is dominated by transformed data (i.e., once $\Delta T$ time units have elapsed), the representation of each stimulus will return to the form that is derived from the untransformed sensor state time series. This is because the description of each subsequently encountered sensor state will be referred to the properties of a collection of transformed sensor states. The time interval $\Delta T$ should be long enough so that the sensor states observed within it populate the sensor state manifold with sufficient density to derive sensor state representations (see the discussions of this issue in Sections II, III, and IV). Specifically, there must be enough sensor state trajectories near each point to endow the manifold with local structure (local vectors, affine connection, or metric). Thus, like a human, the described device must have sufficient "experience" in order to form stimulus representations. Increasing $\Delta T$ will also tend to decrease the noise sensitivity of the method, because it increases the amount of signal averaging in the determination of the local structure. Within these limitations, $\Delta T$ should be chosen to be as short as possible so that the device rapidly adapts to changing observational conditions.

Notice that, if the representation at each point in time is derived from sensor states encountered in a "sliding time window" (e.g., the most recent time interval of length $\Delta T$), a given sensor state may be represented in different ways at different times. This is because the two representations may be referred to different collections of recently encountered sensor states. In other words, the representation of an unchanged stimulus may be time-dependent because the representations are derived from the device's recent "experience" and that experience may be time-dependent. Conversely, a given stimulus will be represented in the same way at two different times as long as the two descriptions are referred to collections of stimuli having the same average local properties (i.e., the same $h_a$) To visualize this, consider the following example. Consider the location of a particle in the center-of-mass coordinate systems of two different clusters of particles in a plane. The two descriptions of the particle's location will be the same, as long as the two collections have the same center-of-mass coordinate systems. In other words, the two representations of the particle's location are identical as long as these descriptions are referred to particle collections with the same average properties. Similarly, the stability of the average local properties of the recently encountered sensor states will stabilize the representation of individual stimuli. If this type of temporal stability is important, stimulus representations should be derived from collections of sensor states that are sufficiently large to have stable average properties. This may put a lower bound on the length of the time period (e.g., $\Delta T$) during which those sensor states are collected.

The devices comprising the present invention behave in some respects like the human subjects of "goggle" experiments. Those experiments suggest that the properties of recently experienced sensory data strongly influence the way a subject's percepts are constructed from subsequent sensory data. Specifically, each subject's perception of stimuli returned to the pre-goggle baseline, after a period of adjustment during which he/she was exposed to familiar stimuli seen through the goggles. In a similar fashion, the invented device's recent "experience" with the external world determines the way it internally represents subsequently encountered stimuli. In particular, the device represents stimuli just as it did before the onset of a transformative process, after a period of adjustment during which it encounters stimuli with average properties similar to those encountered earlier.

Some technical comments should be made about the specific embodiments of the invention in Sections III and IV. In those embodiments, an affine connection was directly derived from sensor states x(t) encountered in a chosen time interval, or it was derived from a metric that was directly related to those sensor states. In either case, the affine connection was used to populate the entire manifold with vectors, which were parallel transported versions of reference vectors at a reference sensor state (e.g., reference vectors derived from the manifold's directionality at the reference sensor state). These vectors were then utilized to create coordinate-independent representations of sensor states. These methods have some advantages with respect to the approach in Section II, which required that local vectors be directly derived from x(t) at every point on the manifold. First of all, there may be points on the manifold at which such vectors cannot be derived because x(t) may not endow the manifold with directionality there. However, it may still be possible to determine an affine connection at such points, and it can then be used to transport vectors to those locations from some other point at which vectors have already been determined. Thus, the method based on affine-connected geometry is more generally applicable. The approach in Section III (i.e., deriving a parallel transport operation directly from sensor state trajectories) is particularly advantageous because it tends to represent the most commonly encountered sensor state trajectories as geodesics (the generalization of the straight lines of Euclidean geometry). In other words, the stimulus tends to evolve along the direction created by parallel transporting the most recently observed line element of x(t) along itself. Thus, such a device has a simple rule that provides some "intuition" about the likely evolution of a changing stimulus. In contrast, a device based on the approach in Section II (i.e., deriving local directionality from sensor state trajectories) has no "intuition" about the likely course of stimulus evolution. It "knows" a set of preferred directions at each point on the manifold, but it cannot use the past behavior of the stimulus to predict which direction it will follow in the future. Similarly, a device based on the methodology in Section IV (the derivation a metric from sensor state trajectories) "knows" that the average speed of sensor state evolution is unity because of Eq.(22). However, the device has no way to predict the direction of stimulus evolution because the stimulus trajectories may not resemble the geodesics of the derived affine connection. In this sense, the specific device embodiments described in Section III are more "intelligent" than those discussed in Sections II and IV.

Notice the important role played by time in all of the above-described methods. Specifically, it establishes local scales along the trajectories through each point on the manifold. In Section II, it sets the scale of the quantities $\hat{h}_1$ (Eq.(9)) that are used to derive the local vectors $H_a$ at each point. In Section III, it sets the scale of the line elements that are parallel transported into one another in an average sense. These trajectory-dependent scales are just sufficient to derive an affine connection at each point. Without this temporal scale, the affine connection would not be fully defined by the sensor state trajectories. Finally, in Section IV, time sets the scale of each line element, thereby making it possible to derive a metric.

It is worth mentioning a number of other embodiments of the invention, based on variations and generalizations of the described method and apparatus. For example, in Section II, the principal vectors at each point could be chosen by using a different clustering criterion (e.g., by using a functional form for E differing from that given by Eq.(12)). In Section IV, there are other ways of using a metric to define an affine connection than that shown in Eq.(24). Furthermore, the path of integration in Eq.(2) could be specified differently than in Sections II–IV. Different values of s will be associated with these different path prescriptions if the manifold has non-vanishing torsion and/or curvature. Finally, in other embodiments, the invented method and apparatus can utilize multiple applications of the resealing process. To see this, note that the family of all signals x(t) that rescale to a given function S(t) can be considered to form an equivalence class. If such a class includes a given signal, it also includes all invertible transformations of that signal. Signals can be assigned to even larger equivalence classes of all signals that produce the same result when rescaling is applied N times in succession, where $N \geq 2$. Successive applications of rescaling may eventually create a function that is not changed by further applications of the procedure (i.e., the serial resealing process may reach a fixed "point"). For example, it is easy to show that, if the self-referential scale of a signal is time-independent (i.e., if h(y) and s(x) are time-independent), it will rescale to such a fixed point. Such a signal is loosely analogous to music, in the sense that musical compositions are also based on a time-independent scale (e.g., the equally tempered scale of Western music).

One embodiment of the present invention is a sensory device with a "front end" that creates stimulus representations, which are not affected by processes that transform the device's sensor states. The output of such a representation "engine" can be subjected to higher level analysis (e.g., pattern recognition) without recalibratiing the device's detector and without modifying the pattern analysis algorithms in order to account for the sensor state transformations. For example, specific embodiments of the invention are computer vision devices that tolerate: 1) variations in the optical/electronic paths of their cameras, 2) alterations of the optical environment and changes in the orientation and position of the camera with respect to the scene, 3) systematic distortions of the stimuli in the scene. Other specific embodiments of the invention are speech recognition devices that tolerate: 1) drifting responses of the microphone and circuitry for detecting sound, 2) changes in the acoustic environment and alterations of the acoustic "channel" between the speaker and the microphone, 3) systematic distortions of the spoken words due to the changing condition of the speaker or, possibly, due to changes in the identity of the speaker. Note the following attractive feature of such devices: the device can successfully adapt to a large change in observational conditions without any loss of data, as long as the change occurs at a sufficiently slow rate. Specifically, if the change occurs in small steps separated by relatively long time intervals, each increment will cause a small distortion of the stimulus representations during a transitional period before the representations revert to their baseline forms. If the pattern analysis software can tolerate these small temporary distortions, it will continue to recognize stimuli correctly, even though the cumulative change of observational conditions may be large over a long time period. In essence, the device is able to "keep up" with a slow pace of transformative change by continually making the adjustments that are necessary to maintain invariant stimulus representations. In contrast, the conventional method of explicit calibration would require that the device be taken "off-line" multiple times during this period in order to expose it to a test pattern.

In Section V.A.2, self-referential rescaling was demonstrated by applying it to synthetic speech-like signals produced by a variety of "voices" and detected by a variety of "ears." These experiments showed that the utterance of any one speaker produced the same rescaled representations in listeners with different ears (FIGS. 7 and 8). Likewise, identical rescaled representations were induced in any one listener by the utterances of two speakers, who sought to transmit the same message (FIGS. 8 and 9). The listener-independence and speaker-independence of the rescaled representations is quite general, even though it was demonstrated in the context of a specific family of voice and ear models. As long as each listener is sensitive to the differences between any two configurations of a speaker's vocal apparatus, there will be an invertible mapping between those configurations and the sensor states produced in the listener. Therefore, if the speaker's utterance is heard by two different listeners with this sensitivity, their sensor states will be invertibly related to one another and, consequently, have identical rescaled representations. Similarly, assume that there is an invertible transformation between the vocal configurations of two speakers when they utter the same message. For example, this might happen because one speaker mimics the other in a consistent fashion or because both speakers "read" from the same "text" in a consistent manner. Then, the sensor signals induced in a listener by the two speakers will also be invertibly related. This is because these sensor signals are invertibly related to vocal configurations, which are themselves invertibly related. It follows that the listener will construct an identical rescaled representation of each speaker's utterance. Finally, as mentioned in Section V.A.2, because the vocal apparatus configurations are invertibly related to the resulting sensor signals, the "gesture" parameter controlling the time series of vocal configurations (i.e., $g(t)$) will have the same rescaled representation as the utterance itself. If this "gesture" parameter is taken to be the "motor" signal in the speaker, this result is consistent with the "motor" theory of speech perception.

Although the experiments in Section V.A.2 were performed with ID speech signals, it is straightforward to generalize the methodology to signals produced by models with multiple degrees of freedom. For example, consider the spectra generated by a vocal apparatus with two degrees of freedom. Each spectrum will correspond to a point on a 2D subspace (i.e., a sheet-like surface) in the space of spectral parameters (e.g., cepstral coefficients), and each utterance will be characterized by a trajectory on this 2D surface. Sections II.B, III, and IV describe several techniques for resealing signals with two (or more) degrees of freedom. It may be computationally practical to apply this technique to human speech that is generated by a vocal apparatus with a relatively small number of degrees of freedom. For the reasons cited previously, such a specific embodiment of the present invention would generate the same internal (rescaled) representation of any given utterance by a wide variety of speakers. Therefore, a speech recognition device with such a "front end" may not need extensive retraining when the speaker's voice or certain other conditions are changed. Furthermore, the adaptive nature of the resealing process might enable it to account for coarticulation during human speech. Recall that the manner in which each sound (i.e., each parameterized spectrum) is rescaled may depend on the nature of recently encountered sounds. It could also depend on the nature of sounds to be encountered in the near future, if the interval $\Delta T$ is defined to include times after the sound to be rescaled. In other words, the rescaled representation of each sound spectrum depends on its acoustic context (defined by the endpoints of $\Delta T$), similar to the contextual dependence of speech perception that is the hallmark of the coarticulation phenomenon. Finally, the foregoing considerations make it tempting to speculate that the human brain itself decodes speech signals by constructing some type of rescaled version of speech spectra. This could account in part for the ease of speech communication involving a variety of speakers, listeners, and acoustic environments.

Another specific embodiment of the present invention is a communications system. In this system, information is communicated in the form of representations that are encoded in transmitted energy and decoded from received energy by means of the above-described self-referential method and apparatus. Because the message is encoded as signal components that are invariant under invertible transformations, its content is not influenced by the specific configurations of the receiver's sensor, the transmitter's broadcasting module, or the channel between them. As shown in FIG. 18, the transmitter is assumed to have state $x$ that controls the waveform of the energy to be transmitted (e.g., controls the excitation of the antenna). The transmitter determines the time series of transmitter states $x(t)$ that is represented by a time series $S(t)$, which constitutes the information to be communicated. This determination is the function of the "inverse representation generator" in FIG. 18. The transmitter then uses the determined $x(t)$ to control its transmission. The transmitted energy is detected and processed by the receiver to produce the time series of receiver states $x'(t)$. We assume that there is an invertible correspondence between the transmitter states and the receiver states; i.e., $x \leftrightarrow x'$ is one-to-one. This implies that the transmitter does not distinguish between transmissions that are indistinguishable at the receiver, and the receiver does not distinguish between transmissions that the transmitter does not distinguish. This is true in a variety of circumstances. For example, suppose that $x$ and $x'$ are the short-term Fourier spectra of time-dependent baseband signals in the antennas of the transmitter and receiver, respectively. Then, they will be related in a one-to-one fashion if the "channel" between the transmitter and receiver is characterized by any linear time-independent transfer function that has non-vanishing Fourier components and a sufficiently short temporal dispersion (e.g., OFDM). The receiver decodes the received signal by determining the time series of representations of the receiver states. Because this process is coordinate-independent, it produces the same time series of representations $S(t)$ that was encoded in the transmission. For example, if the transmitter seeks to communicate the information in FIG. 3b, it could encode this information as the transmitter states in FIG. 3a. Even if the channel non-linearly distorts the signal to produce the receiver states in FIG. 3c, the receiver will decode the transmission to recover the message in FIG. 3b. In one embodiment, the invention can be used to establish universal communication among heterogeneous transmitters and receivers, whose states differ by unknown invertible mappings. Such a communication system resembles speech in the sense that: 1) the same information is carried by signals that are related to one another by a wide variety of transformations; 2) the transmitter and receiver need not explicitly characterize the transformation, which remains unknown; 3) if the nature of the transformation changes, faithful communication resumes after a period of adaptation. In this type of communications system, the "instructions" for encoding and decoding each message increment are contained in the transmitted and received signals, respectively. In this sense, the communications signal is similar to music that inherently contains information about the musical scale and the key of upcoming bars. This communication process is also illustrated by the following analogy. Suppose that one individual sought to visually communicate numbers to another individual as the coordinates of a particle at changing positions in a plane, and suppose that the coordinate system of the receiving party differed from that of the transmitting party by an unknown rotation and/or translation. The transmitter could encode information as the particle's coordinates in the internal coordinate system of the P most recently displayed particle positions (i.e., the coordinate system that originates at the collection's "center-of-mass" and is oriented along the principal axes of its inertia tensor). Information will be transmitted faithfully, because the receiving party can also compute the particle's coordinates in the collection's internal coordinate system. Notice that this method of communication will be accurate even if there are time-dependent changes in the distribution and internal coordinate system of the P most recently displayed particles. This is because the transmitter and receiver utilize the same changing collection to encode and decode each subsequent message increment, respectively. Therefore, the technique does not require stability of the intrinsic structure of the "stimulus" collection, the property that was required by the previously described sensory devices in order to ensure temporally stable stimulus representations. The only requirement for accurate communication is that the collection of transmitter states from earlier transmissions must densely populate the part of the manifold to be used for subsequent message increments.

Humans have a remarkable ability to perceive the intrinsic constancy of a stimulus even though its "appearance" is changing due to extraneous factors. This phenomenon has been the subject of philosophical discussion since the time of Plato, and it has also intrigued modern neuroscientists. A specific embodiment of the present invention is a sensory device that represents stimuli invariantly in the presence of processes that systematically transform its sensor states. These stimulus representations are invariant because they encode "inner" properties of the time series of the stimulus configurations themselves; i.e., properties that are independent of the nature of the observing device or the conditions of observation. Perhaps, human perception of stimulus constancy is due to a similar appreciation of the "inner" structure of experienced stimulus time series. A significant evolutionary advantage would accrue to organisms that developed this ability.

VII. Embodiments as a Sensory Device
VII.A. Stimuli

Stimuli emit and/or reflect energy that causes one or more of the device's detectors to produce a signal. Specific embodiments of the present invention detect stimuli that may be external to the sensory device and/or stimuli that may be internal to it. Examples of external stimuli include "scenes" containing a variety of animate subjects (e.g., humans or other living matter) and/or inanimate objects (e.g., naturally occurring parts of a "landscape", manufactured items, etc.). Internal stimuli that may affect the device's detectors include components measuring the position and/or orientation and/or motion of the device with respect to its environment, components measuring the position and/or orientation and/or motion of parts of the device (e.g., its detectors) relative to the rest of the device, components measuring the internal state of any of the device's parts (including the detectors, processing units, representation generator, etc.).

VII.B. Energy

Specific embodiments of the present invention detect electromagnetic energy emitted or reflected by a stimulus. The energy may have frequencies in any part of the electromagnetic spectrum, including the radio, microwave, infrared, optical, ultraviolet, and/or x-ray parts of the spectrum. This energy may be transmitted from the stimulus to the device's detectors through any type of medium, including empty space, earth's atmosphere, wave-guides, wires, and optical fibers. The energy from the stimulus may also be transmitted by pressure variations and/or movements in a gaseous, liquid, or solid medium (e.g., acoustic or mechanical vibrations).

VII.C. Detectors

One or more detectors that are part of the sensor module of the device may detect the energy emitted and/or reflected from stimuli. Specific embodiments of the present invention utilize detectors including radio antennas, microwave antennas, infrared and optical cameras, and media sensitive to ultraviolet and/or X-ray energy. Other examples of detectors include microphones, hydrophones, pressure transducers, devices for measuring translational and angular position, devices for measuring translational and angular velocity, devices for measuring translational and angular acceleration, and devices for measuring electrical voltage and/or electrical current. The output of the detectors may be saved or recorded in a memory device (e.g., the memory module of a computer or in the weights of a neural network). In specific embodiments of the present invention, the recorded detector signals may be used to determine a time series of synthetic ("imaginary") detector signals that is also recorded in a memory device. For example, the synthetic detector signals may form a path (in the space of possible detector signals) connecting detector signals from observed stimuli to one another or connecting them to a synthetic detector signal corresponding to a "template" stimulus. In the following, "detector output" refers to the output of the device's detectors produced by stimuli and to synthetic detector signals.

VII.D. Processing Units

In specific embodiments of the present invention, the detector output signals may be combined in linear or non-linear fashion by the processing units. This processing could be done by general-purpose central processing units that utilize serial software programs and/or parallel software programs (e.g., programs with neural net architecture). The processing units could also utilize specialized computer hardware (e.g., array processors), including neural network circuits. Examples of such signal processing include filtering, convolution, Fourier transformation, decomposition of signals along specific basis functions, wavelet analysis, dimensional reduction, parameterization, linear or non-linear resealing of time, image formation, and image reconstruction. The processed signals are saved in a memory device (e.g., the memory module of a computer or in the weights of a neural network). In specific embodiments of the present invention, the recorded processed signals may be used to determine a time series of synthetic ("imaginary") processed signals that is also saved in a memory device. For example, the synthetic processed signals may form a path (in the space of possible processed signals) connecting the processed signals from observed stimuli to one another or to a synthetic processed signal corresponding to a "template" stimulus. In the following, "processed signal" refers to the output of the signal processor produced by stimuli and to synthetic processed signals.

VII.E. Sensor State

A sensor state is a set of numbers that comprises the processed signal. In specific embodiments of the present invention, possible sensor states include: pixel values at one or more locations in a digital image, numbers characterizing one or more aspects of a transformed image (e.g., filtered image, convolved image, Fourier transformed image, wavelet transformed image, morphologically transformed image, etc.), numbers characterizing the locations and/or intensities of one or more specific features of an image or a transformed image, numbers characterizing a time domain signal at certain times, numbers characterizing one or more aspects of a transformed time domain signal (e.g., a filtered signal, a convolved signal, a Fourier transformed signal, a wavelet transformed signal, etc.), numbers characterizing the locations and/or intensities of one or more features of a time domain signal or a transformed time domain signal, and/or numbers characterizing the parameterization of the time-domain signal.

VII.F. Representation Generator

Specific embodiments of the present invention may have one or more representation generators. Each representation generator may be implemented on a general-purpose central processing unit and/or on specialized processors (e.g., array processors, neural network circuits) with software having serial and/or neural network architecture. The input of a representation generator includes the time series of sensor states x(t) encountered in a chosen time interval, as well as certain prior knowledge mentioned below. The output of the representation generator includes the time series of coordinate-independent sensor state representations S(t), as well as the input time series of sensor states x(t). The input and output of the representation generator may also include the time series of detector signals from which the sensor states were created. At any time, the representation generator will utilize the input information to identify in a coordinate-independent fashion one or more of the following features on the sensor state manifold: a reference sensor state $x_0$, reference vectors $h_{0a}$ at the reference sensor state, vectors $h_a$ at all other points of interest on the manifold, and a path connecting $x_0$ to any other point of interest on the manifold. A representation generator will use the procedure denoted by Eqs.(1–2) to create s, a coordinate-independent representation of any point of interest x on the manifold. One or more representation generators may also receive inputs, which are representations S(t) produced by one or more other representation generators, and use these inputs to create other functions S'(t) that constitute representations of the input representations.

VII.F.1. Reference State

A representation generator may identify the reference sensor state to be a coordinate-independent feature of the time series of sensor states x(t) encountered in a chosen time interval. For example, in one specific embodiment of the present invention, it could identify the reference state as the local maximum of the function defined by the number of times each sensor state is encountered during a specific time period. Such a state may be identified by explicit computational processes or by neural networks, which are designed to find such a state from the time series of sensor states x(t).

Prior knowledge could also be used to identify the reference sensor state. For example, the device may choose the reference state to be a specific sensor state that is known a priori to remain invariant under all relevant coordinate transformations (i.e., in the presence of all expected transformative processes). Or, the device could identify the reference state to be the sensor state produced by a specific stimulus that the device's operator "shows" to the device at specific times.

VII.F.2. Reference Vectors at the Reference Sensor State

A representation generator may identify the reference vectors $h_{0a}$ at the reference sensor state as coordinate-independent features of the time series of sensor states encountered during a chosen time interval. For example, in one specific embodiment of the present invention, it could identify these vectors to be the most characteristic values of $$\frac{dx}{dt}$$

when the sensor state trajectory x(t) is in the vicinity of the reference sensor state (e.g., Section II.B). These vectors could be identified by explicit computational processes or by neural networks, which are designed to find such vectors from the history of previously encountered states x(t). Prior knowledge could also be used to identify the vectors $h_{0a}$ at the reference sensor state. For example, the device may choose these vectors to be specific vectors that are known a priori to remain invariant under all relevant coordinate transformations (i.e., in the presence of all expected transformative processes). Or, the device could identify these vectors with the sensor state changes produced by specific stimulus changes that the device's operator "shows" to the device at specific times.

VII.F.3. Vectors at Other Points on the Sensor State Manifold

In specific embodiments of the present invention, the representation generator may identify vectors at other points on the manifold by any coordinate-independent means, including the following:

VII.F.3.a. Sensor State Manifolds Having Local Directionality

A representation generator may identify the vectors $h_a$ at any given point of interest with coordinate-independent features of the time series of sensor states encountered in a chosen time interval. For example, it could identify these vectors to be the most characteristic values of $$\frac{dx}{dt}$$

when the sensor state trajectory x(t) is in the vicinity of the point of interest (e.g., Section II.B). These vectors could be identified by explicit computational processes or by neural networks, which are designed to find such vectors from the sensor states x(t) encountered in a chosen time interval. The values of these vectors at a collection of closely spaced points may be interpolated in order to estimate their values at other points on the manifold. In specific embodiments of the present invention, the interpolation process could be implemented with parametric techniques (e.g., splines) or by neural networks. The representation generator can use these vectors to specify a particular path connecting the reference state to any sensor state of interest. For example, such a path can be specified by requiring it to consist of N or fewer segments (N being the manifold's dimension), where each segment is directed along the local vector $h_a$ with one particular value of index a and where these index values are encountered along the path in a predetermined order that does not repeat (e.g., in order of ascending values of a, as in Section II.B). The procedure in Eqs.(1–2) may be applied to this path and to the vectors $h_a$ along it to generate the coordinate-independent representation s of a sensor state of interest. The values of s corresponding to predetermined values of x may be computed in this manner. The values of s at intervening values of x may be computed by interpolation between the predetermined values of x. In specific embodiments of the present invention, the interpolation may be performed by parametric means (e.g., splines) or by neural network means.

VII.F.3.b. Sensor State Manifolds that Support Parallel Transport

In specific embodiments of the present invention, the representation generator may use the trajectory of sensor states x(t) encountered in a chosen time interval in order to derive coordinate-independent parallel transport rules in a portion of the sensor state manifold. For example, in specific embodiments of the present invention, such rules may be derived from the requirement that the sensor state trajectory segments in that part of the manifold be geodesic or approximately geodesic (e.g., in an average or statistical sense; see Section III). These parallel transport rules (e.g., the corresponding affine connection) may be identified by explicit computational processes or by neural networks, which are designed to find such rules from the states x(t) encountered in a chosen time interval. The parallel transport rules at a collection of closely spaced points may be interpolated in order to estimate the parallel transport rules at other points on the manifold. In specific embodiments of the present invention, the interpolation process may be implemented with parametric techniques (e.g., splines) or by neural networks. The resulting parallel transport operation on the manifold may be implemented by explicit computational processes (e.g., Section III) or by a neural network. The representation generator may use the parallel transport rules and the reference vectors at the reference sensor state to specify a particular path connecting the reference state to any sensor state of interest and to determine vectors $h_a$ along the path. For example, in some embodiments of the present invention, the procedure in Section III can be used to specify such a path. Alternatively, in other embodiments of the present invention, the procedure in Section III can be modified by creating and following N or fewer connected geodesic segments, each segment corresponding to a different vector index a and the segments being connected in a predetermined order of indices that differs from the ascending order used in Section III. The procedure in Eqs.(1–2) may be applied to this path and to the vectors $h_a$ along it in order to generate the coordinate-independent representation s of a sensor state of interest. The values of s corresponding to predetermined values of x may be computed in this manner. The values of s at intervening values of x may be computed by interpolation between the predetermined values of x. In specific embodiments of the present invention, the interpolation may be performed by parametric means (e.g., splines) or by neural network means.

VII.F.3.c. Sensor State Manifolds that Support a Metric

In one specific embodiment of the present invention, the representation generator may use the trajectory of sensor states x(t) encountered in a chosen time interval in order to derive a coordinate-independent metric operation in a portion of the manifold. For example, in some embodiments of the present invention, such a metric operation may be derived from the requirement that the local sensor state trajectory segments traversed in unit time intervals have approximately unit length (e.g., in an average or statistical sense; see Section IV). This metric operation (e.g., the corresponding metric tensor) may be identified by explicit computational processes or by neural networks, which are designed to find such a metric operation from the sensor states x(t) encountered in a chosen time interval. The metric operation at a collection of closely spaced points may be interpolated in order to estimate the metric operation at other points on the manifold. In specific embodiments of the present invention, the interpolation process may be implemented with parametric techniques (e.g., splines) or by neural networks. The computation of length from the resulting metric operation may be implemented by explicit computational processes or by a neural network. The metric operation may be used to derive parallel transport rules on the manifold by requiring each segment on each geodesic of the parallel transport process be parallel transported into a segment with equal metric length on the same geodesic. In some specific embodiments of the present invention, the parallel transport rules may also be required to parallel transport any vector into another vector with equal metric length (e.g., Eq.(24)). The resulting parallel transport process may be derived from the metric operation and/or implemented by explicit computational processes (e.g., Section IV) or by a neural network. The representation generator may use the parallel transport rules and the reference vectors at the reference sensor state to specify a particular path connecting the reference state to any sensor state of interest and to derive vectors $h_a$ at points along the path. For example, in one embodiment of the present invention, the procedure in Section IV can be used to specify such a path and the vectors on it. Alternatively, in other embodiments, the procedure in Section IV can be modified by creating and following N or fewer geodesic segments, each segment corresponding to a different vector index a and the segments being connected in a predetermined order of indices that differs from the ascending order used in Section IV. The procedure in Eqs.(1–2) may be applied to this path and to the vectors $h_a$ along it to generate the coordinate-independent representation s of a sensor state of interest. The values of s corresponding to predetermined values of x may be computed in this manner. The values of s at intervening values of x may be computed by interpolation between the predetermined values of x. In specific embodiments of the present invention, the interpolation may be performed by parametric means (eg., splines) or by neural network means.

Note is made of the fact that specific embodiments of the present invention may contain more than one of the above-described representation generators. Each of these may receive input that consists of a time series of sensor states x(t) and/or a time series of representations S(t), generated by one or more other representation generators. The latter time series can be processed as a sensor state time series.

Note is also made of the fact that, in specific embodiments of the inventive method and apparatus, the sensor states encountered in a predetermined time interval endow the sensor state manifold with local structure (e.g., vectors $h_a$, parallel transport operation, and/or metric operation). In a portion of the manifold, this structure may vary over distances greater than a scale $|\Delta x|$ and may not vary significantly over shorter distances. In preferred embodiments of the invention, the local structure at any sample sensor state may be derived from the sensor states encountered in a small neighborhood of the sample sensor state during a predetermined time interval. The size of the small neighborhood may be less than $|\Delta x|$ divided by a small positive integer, and the spacing between the sample sensor states may be less than $|\Delta x|$. The local structure at sensor states between a collection of sample sensor states may be estimated by interpolating among its values at the sample sensor states, by means of parametric or non-parametric (e.g., neural network) interpolation techniques. The coordinate independent representation of a sensor state of interest may be estimated by performing the sum corresponding to Eq.(2), in which the magnitude of each small displacement $\delta x$ is less than the local value of $|\Delta x|$. The local vectors at each path point (Eq.(1)) may be estimated to be the vectors at a point that is separated from the path point by a distance less than the local value of $|\Delta x|$, or they may be estimated by the above-described interpolation procedure.

VII.G. Higher Level Analysis of Stimulus Representations

In specific embodiments of the present invention, the output of the representation generators, including the sensor states and detector signals at predetermined time points, may form the input of hardware and/or software modules that perform higher level analysis. Such analysis may identify aspects of the nature of the stimuli (e.g., pattern recognition and/or pattern classification).

VIII. Embodiments as a Communication System

VIII.A. Transmitter

VIII.A.1. Inverse Representation Generator

In one specific embodiment of the present invention, the input of the inverse representation generator consists of the representations $S(t)$ to be communicated at chosen time points and, possibly, the transmitter states $x(t)$ in chosen time intervals. This generator determines the transmitter states in other time intervals so that the resulting transmitter state time series is represented by $S(t)$ at the said chosen time points. In one specific embodiment of the present invention, the representation is determined by a process that produces the same representation from the transmitter state time series as it produces from an invertible transformation of the transmitter state time series. The determined time series of transmitter states $x(t)$ controls the transmission of energy by the broadcasting unit of the transmitter.

VIII.A.2. Broadcasting Unit

In a specific embodiment of the present invention, the broadcasting unit uses the above-mentioned time series of transmitter states $x(t)$ to control the energy that it transmits to the receiver. The broadcasting unit may first subject the values of x to a variety of linear and non-linear processing operations. This processing could be done by general-purpose central processing units that utilize serial programs and/or programs with neural net architecture. The processing units could also utilize specialized computer hardware (e.g., array processors), including neural network circuits. Examples of such signal processing include filtering, convolution, Fourier transformation, decomposition of signals along specific basis functions, wavelet analysis, parameterization, dimensional reduction, and linear or non-linear rescaling of time. The output of the processing unit controls the operation of the transducer that transmits energy to the receiver. The broadcasting unit may use the processed $x(t)$ to modulate the amplitude, phase, frequency, and/or other features of a carrier signal to produce the waveform of the transmitted energy. In specific embodiments of the present invention, the transmitted energy may be electromagnetic energy with its frequencies in the radio, microwave, infrared, optical ultraviolet, and/or x-ray part of the spectrum. This energy may be transmitted through a variety of media, including empty space, the atmosphere, wave-guides, wires, and optical fibers. In specific embodiments of the invention, the transmitted energy may also be transmitted by pressure variations and/or movements in a gaseous, liquid, or solid medium (e.g., acoustic or mechanical vibrations). The broadcasting unit may utilize a variety of mechanisms to provide access to multiple users (e.g., the mechanisms of TDMA, FDMA, CDMA).

VIII.B. Receiver

In a specific embodiment of the present invention, the receiver is a sensory device, like the ones described in Section VII. The processing unit of the receiver may demodulate the waveform of the detected signal and/or process it in other ways, as described in Section VII. The sensor state x' that is created by the processing unit is related to the corresponding transmitter state x by an invertible transformation. The receiver's representation generator determines the representation of the sensor state time series x'(t) from the sensor states encountered in a chosen time interval. In a specific embodiment of the present invention, this representation is determined by a process that determines the same representation from the sensor state time series as it determines form an invertible transformation of the sensor state time series. The output of the representation generator consists of the time series of representations $S(t)$ and the time series of sensor states x'(t). In a specific embodiment of the present invention, this information comprises the input of the analysis module that subjects it to analysis (e.g., pattern recognition and classification). The output of the analysis module, as well as the output of the representation generator, may be displayed to the operator of the receiver. In specific embodiments, the receiver may include mechanisms that account for the fact that multiple users may be transmitting and receiving energy simultaneously (e.g., the mechanisms of TDMA, FDMA, CDMA, etc.).

Each of the above-mentioned steps may be performed by one or more general-purpose central processing units and/or special computer hardware units (e.g., array processors, neural network circuits) that utilize serial software programs and/or parallel software programs (e.g., programs with neural net architecture). Any suitable computer, which would include monitor, mouse, keyboard, RAM, ROM, disc drive, and communication ports, can be used to implement the inventive method and apparatus.

IX. Embodiments as a "Speech" Recognition Device

IX.A. Sources of Speech Stimuli or Speech-like Stimuli

The speech stimuli or speech-like stimuli may be produced by humans, other animals, or machines (including a machine comprising a part of the apparatus described in this invention).

IX.B. Energy and Medium

In specific embodiments of the present invention, the energy emitted by the above-described sources may be carried by pressure variations and/or movements in a gaseous, liquid, or solid medium (e.g., acoustic or mechanical vibrations). It may also be carried by electromagnetic fields with frequencies in the audio, radio, microwave, infrared, optical, ultraviolet, and/or x-ray part of the electromagnetic spectrum. These fields may occur in a variety of media, including empty space, earth's atmosphere, wave-guides, wires, and optical fibers.

IX.C. Detectors

One or more detectors that are part of the sensor module of the device may detect the energy of the stimuli. In specific embodiments of the present invention, such detectors may include microphones, hydrophones, pressure transducers, devices for measuring electrical voltage and electrical current, radio antennas, microwave antennas, infrared and optical cameras, and media sensitive to ultraviolet and/or X-ray energy.

IX.D. Processing Units

The signals from the detectors may be combined in linear or non-linear fashion by the processing units. In specific embodiments of the present invention, such signal processing may include filtering, convolution, Fourier transformation, decomposition of signals along specific basis functions, wavelet analysis, parameterization, dimensional reduction, and linear or non-linear rescaling of time. For example, in specific embodiments of the present invention, the time-dependent detector signals within any given time interval may be used to derive a set of parameters that constitutes a "feature vector". For instance, the time-dependent detector signal may be multiplied by any "windowing" function such as a Hamming or Hanning window. The resulting weighted data may then be subjected to a Fourier transformation or a wavelet transformation, or these data may be projected onto any other set of basis functions. The "spectrum" produced by such a transformation may be further processed by averaging it over suitable intervals in the space of the transformation indices (e.g., the indices of the utilized basis functions, such as the frequency of the Fourier basis functions). A cepstrum may then be derived from the processed spectrum. Alternatively, the time-dependent detector signals in any given time interval may be used to derive linear prediction coefficients, which may be used to derive the positions of the poles of an associated filter transfer function. In this way, the time-dependent data in each time interval may be used to derive a "feature vector" from some or all of the time-dependent data and/or some or all of the associated spectral values and/or some or all of the associated cepstral values and/or some or all of the linear prediction coefficients and/or some or all of the transfer function pole positions and/or other quantities derived from the time-dependent data in the given time interval. In specific embodiments of the present invention, the feature vector may be processed by determining a subspace of the space containing the feature vector and by determining a procedure for projecting the feature vector into the subspace. The feature vector may then be assigned the coordinates of its projection in any convenient coordinate system defined in this subspace. For example, that subspace may be a piece-wise linear subspace comprised of an aggregation of portions of hyper-planes in the space containing the feature vector.

In specific embodiments of the present invention, one or more of the above-mentioned processing steps may be performed by general-purpose central processing units and/or special computer hardware units (e.g., array processors, neural network circuits) that utilize serial software programs and/or parallel software programs (e.g., programs with neural net architecture).

IX.E. Sensor State

The sensor state is the set of numbers that the processing units create from the detector signals induced by a given stimulus. In specific embodiments of the present invention, sensor states include numbers characterizing the time domain signal in a chosen time interval, numbers characterizing one or more aspects of the processed time domain signal (e.g., a filtered signal, a convolved signal, a Fourier transformed signal, a wavelet transformed signal, etc.), and/or numbers characterizing the locations and/or intensities of one or more features of the time domain signal or the processed time domain signal. For example, the sensor state may consist of the feature vector described in Section IX.D, or it may consist of the coordinates of the feature vector's projection in the lower dimensional subspace that was described in IX.D.

IX.F. Representation Generator

The device may have one or more representation generators. Each representation generator may be implemented on general-purpose central processing units and/or on specialized processors (e.g., array processors, neural network circuits) with software having serial and/or parallel (e.g., neural network) architecture. The input of a representation generator includes the time series of sensor states x(t) in a chosen time interval, as well as certain prior knowledge. The output of the representation generator includes the time series of coordinate-independent sensor state representations S(t), as well as the input time series of sensor states x(t). The input and output of a representation generator may also include the time series of detector signals from which sensor states are created, as well as a description of the subspace of feature space onto which feature vectors are projected in order to produce sensor states. In specific embodiments of the present invention, at any time, the representation generator will utilize the input information to identify in a coordinate-independent fashion one or more of the following features on the sensor state manifold: a reference sensor state $x_0$, reference vectors $h_{0a}$ at the reference state, vectors $h_a$ at all other points of interest on the manifold, and a path connecting $x_0$ to any other point of interest on the manifold. In specific embodiments of the present invention, these features on the sensor state manifold may be identified as described in VII.F and other Sections. In specific embodiments of the present invention, a representation generator will use the procedures described in Sections II, III, and IV to create s, a coordinate-independent representation of any point of interest x on the manifold. One or more representation generators may also receive inputs, which are representations S(t) produced by one or more other representation generators, and use these inputs to create other functions S(t) that constitute representations of the input representations.

IX.G. Higher Level Analysis of Stimulus Representations

In specific embodiments of the present invention, the output of the representation generators may form the input of hardware and/or software modules that perform higher level analysis. Such analysis may include pattern recognition and pattern classification. For example, this module may associate the output of the representation generators with a sequence of phonemic features and/or phonemes and/or allophones and/or demisyllables and/or syllables and/or words and/or phrases and/or sentences. The analysis module may recognize the voices of certain speakers by associating each speaker with the characteristics of the output of the representation generator, including the characteristics of the subspace of feature space onto which feature vectors are projected in order to produce sensor states.

X. Embodiments as a Stimulus Translation Device

In one specific embodiment of the present invention, the stimuli of stimulus source S are "translated" into the stimuli of stimulus source S' by the following process. The stimuli to be translated are produced by S, and the method and apparatus of earlier Sections are used to find a time series of scale values S(t) corresponding to a time series of sensor states x(t) derived from the S stimuli. These scale values are determined from sensor states recorded in a chosen time interval, these sensor states being produced by the S stimuli to be translated (i.e., x(t)) and, possibly, by other stimuli produced by S. The next step is to find a time series of sensor states x'(t) on the sensor state manifold of S' that implies the same time series of scale values S(t) when it is subjected to the process in earlier Sections. The scale values of the determined time series x'(t) are derived from sensor states in a chosen time interval, these sensor states including the sensor states of the translated stimuli (i.e., x'(t)) and, possibly, the sensor states produced by other S' stimuli. Next, one finds a time series of feature vectors that corresponds to the determined time series of sensor states x'(t). Then, a time series of S' stimuli is found that is characterized by the derived time series of feature vectors. For example, suppose that the stimulus sources are two speakers (S and S') and the stimuli are acoustic waveforms of their speech. The time series of feature vectors may be a time series of: 1) Fourier spectra or 2) cepstra or 3) wavelet representations or 4) linear prediction coefficients or 5) positions of poles corresponding to linear prediction coefficients. Then, a translated acoustic waveform from S' may be synthesized by inverting: 1) the short-term Fourier analysis or 2) the cepstral analysis or 3) the wavelet analysis or 4) the linear prediction analysis or 5) the linear prediction pole position analysis, respectively. The synthesized acoustic waveform from S' is the utterance of S, after it has been translated into the speech of S'.

In a specific embodiment of the present invention as a speech translation device, the following process is used to determine the above-described time series of sensor states x'(t). First, a non-message sample of speech from speaker S is used to create a scale function $s_{NM}(X)$ on the "voice" manifold of sensor states x produced by that speaker, using the procedure described in Section VIII and earlier Sections. Similarly, a non-message sample of speech from speaker S' is used to create a scale function $s_{NM}'(X')$ on the "voice" manifold of sensor states x' produced by that speaker. The scale function $s_{NM}(X)$ is used to derive $s(t)=s_{NM}[x(t)]$ from the sensor state time series x(t), produced by the S utterance to be translated. Then, the scale function $s_{NM}'(x')$ is used to find x'(t) such that $s(t)=s_{NM}'[x'(t)]$.

In all of the specific embodiments of the present invention, each step may be performed by one or more general-purpose central processing units and/or special computer hardware units (e.g., array processors, neural network circuits) that utilize serial software programs and/or parallel software programs (e.g., programs with neural net architecture). Any suitable computer, which would include monitor, mouse, keyboard, RAM, ROM, disc drive, and communication ports, can be used to implement the inventive method and apparatus.

Specific embodiments of a method and apparatus for creating stimulus representations according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

REFERENCE TO COMPUTER PROGRAM LISTING APPENDIX

This application includes a computer program appendix listing (in compliance with 37 C.F.R. §1.96) containing source code for a specific embodiment illustrating how the present inventive method and apparatus may be implemented. The computer program appendix listing is submitted herewith on one original and one duplicate compact disc (in compliance with 37 C.F.R. §1.52(e)) designated respectively as Copy 1 and Copy 2, and labeled in compliance with 37 C.F.R. §1.52(e)(6).

Each listed computer program and/or file was created using the programming language Mathematica 3.0 (Wolfram Research, Inc., Urbana, Ill.), running on a Mactintosh PowerBook G3 computer with the Mac OS 8.1 operating system.

All the material in this computer program appendix listing on compact disc is hereby incorporated in its entirety herein by reference, and identified by the following table of file names, creation/modification date, and size in bytes:

| NAMES OF FILES | CREATED/ MODIFIED | SIZES IN BYTES |
| --- | --- | --- |
| 1DExample.SP.1.txt | Feb. 03, 2001 | 12,000 |
| 1DSpCoord.2.32__1DSyn.3.31.NL.tx | Jun. 15, 2001 | 12,000 |
| 1DSpCoord.2.32__1DSyn.3.31.txt | Jun. 15, 2001 | 12,000 |
| 1DSyn.3.31.coord.txt | Jun. 15, 2001 | 24,000 |
| 1DSyn.3.31.txt | Jun. 15, 2001 | 24,000 |
| 1DTransform.txt | Oct. 23, 2000 | 12,000 |
| Disp2DHMap2.0__2.0__1.25.txt | Oct. 12, 2000 | 36,000 |
| DisplayMap3.0__2.4__2.2.txt | Aug. 23, 2000 | 36,000 |
| HMapParameterFile.txt | Oct. 12, 2000 | 12,000 |
| Make1DMap.3.19.txt | Oct. 04, 2000 | 12,000 |
| Make2DHMap.2.0.txt | Oct. 11, 2000 | 36,000 |
| MakeMap2.4.txt | Aug. 16, 2000 | 36,000 |
| MapParameterFile.txt | Aug. 22, 2000 | 12,000 |
| SI.3.1.txt | Apr. 23, 2001 | 24,000 |
| SI.3.1a__1DSpCo.2.32.NL.txt | Jun. 15, 2001 | 24,000 |
| SI.3.1a__1DSpCo.2.32.txt | Jun. 15, 2001 | 24,000 |
| SIoP.6.4__SI3.1.Door.CBrA.txt | May 16, 2001 | 12,000 |
| SIoP.6.4__SI3.1.Door.CrA.txt | May 08, 2001 | 12,000 |
| SRRec4.6.txt | Nov. 08, 2000 | 36,000 |
| SRRec5.5.txt | Nov. 09, 2000 | 36,000 |
| SRRec6.1__1A.txt | Nov. 16, 2000 | 48,000 |
| SRRec6.1__1AB.txt | Nov. 16, 2000 | 48,000 |
| VETraj.1.0__1DSyn.3.31.NL.txt | Jun. 17, 2001 | 12,000 |
| VETraj.1.0__1DSyn.3.31.txt | Jun. 17, 2001 | 12,000 |

What is claimed is:

1. A method of detecting and processing time-dependent signals from a stimulus source, the method comprising the steps of:

a) detecting with a detector the signal energy from stimuli from the stimulus source at predetermined time points;

b) processing the output signals of the detector to produce a sensor state x(t) at each time point t in a collection of predetermined time points, said sensor state x(t) including one or more numbers;

c) saving in computer memory said output signals of the detector and said sensor states x(t) at each time point in the collection;

d) processing the saved sensor states x(t) to produce a representation of each sensor state x of a predetermined collection of sensor states in the space of possible sensor states, each said representation including one or more numbers and said processing of said saved sensor states x(t) having the property that said representation of each said sensor state x is approximately the same as the representation of the transformed said sensor state x'=x'(x), said representation of said transformed sensor state x' being produced from the transformed time series of said saved sensor states x'(t)=x'[x(t)], x'(x) being a transformation on the space of possible sensor states;

e) saving in computer memory said sensor states in said predetermined collection of sensor states and said representations of the sensor states in said predetermined collection of sensor states; and f) processing at least one of the saved output signals of the detector and the sensor states in said predetermined collection and corresponding representations to determine aspects of the nature of the stimuli producing the sensor states in said predetermined collection.

2. The method according to claim 1 wherein said transformation x'(x) is an invertible transformation on the space of possible sensor states.

3. A method of detecting and processing time-dependent signals from a stimulus source, the method comprising the steps of:

a) detecting with a detector the signal energy from stimuli from the stimulus source at predetermined time points;

b) processing the output signals of the detector to produce a sensor state x(t) at each time point t in a collection of predetermined time points, said sensor state x(t) including one or more numbers;

c) saving in computer memory said output signals of the detector and said sensor states x(t) at each time point of said collection;

d) determining a reference sensor state $x_0$ in the space of possible sensor states;

e) determining one or more reference vectors $h_{0a}$ at the reference sensor state $x_0$, the reference vector label a having integer values and each said reference vector having one or more dimensions;

f) processing at least one of said saved sensor states x(t) and said reference sensor state $x_0$ and said reference vectors $h_{0a}$ to determine one or more preferred vectors $h_a$ at each sensor state x in a predetermined collection of sensor states, each said preferred vector having one or more dimensions;

g) processing at least one of said saved sensor states x(t) and said reference sensor state $x_0$ and said reference vectors $h_{0a}$ to determine paths in the space of possible sensor states, each said path connecting the reference sensor state $x_0$ to a sensor state of interest in a predetermined collection of sensor states;

h) determining the representation $$s = \int_{x_0}^{x} \delta s$$

of each sensor state x in a predetermined collection of sensor states, said integral being along the path connecting $x_0$ to x, $\delta s$ at each sensor state on said path satisfying $$\delta x = \sum_{a=1,\ldots,N} h_a \delta s_a,$$

$\delta x$ being a small displacement along the path at said sensor state on said path, $h_a$ denoting the preferred vectors near said sensor state on said path, and N being the number of dimensions of the space of possible sensor states;

i) saving in computer memory said sensor states in said predetermined collection of sensor states and said representations of the sensor states in said predetermined collection of sensor states; and j) processing at least one of the saved output signals of the detector and the sensor states in said predetermined collection and corresponding representations to determine aspects of the nature of the stimuli producing the sensor states in said predetermined collection.

4. The method according to claim 3 wherein the stimulus source is at least one of a stimulus source external to the device that detects and processes the signal energy from stimuli and a stimulus source that is a part of the device that detects and processes the signal energy from stimuli.

5. The method according to claim 3 wherein the stimulus source produces at least one stimulus selected from the group consisting of an electromagnetic stimulus, auditory stimulus and mechanical stimulus.

6. The method according to claim 3 wherein the energy produced by the stimulus source is carried by a medium selected from the group consisting of empty space, earth's atmosphere, wave-guide, wire, optical fiber, gaseous medium, liquid medium, and solid medium.

7. The method according to claim 3 wherein the detector is selected from the group consisting of radio antenna, microwave antenna, infrared camera, optical camera, ultraviolet detector, X-ray detector, microphone, hydrophone, pressure transducer, translational position detector, angular position detector, translational motion detector, angular motion detector, electrical voltage detector, and electrical current detector.

8. The method according to claim 3 wherein a sensor state is produced by processing the output signals of the detector using a method selected from the group consisting of a linear procedure, non-linear procedure, filtering procedure, convolution procedure, Fourier transformation procedure, procedure of decomposition along basis functions, wavelet analysis, dimensional reduction procedure, parameterization procedure, and procedure for rescaling time in one of a linear and non-linear manner.

9. The method according to claim 3 wherein said reference sensor state $x_0$ in the space of possible sensor states is determined by processing said saved sensor states x(t), said processing having the property that the transformed reference sensor state $x_0' = x'(x_0)$ is approximately determined by processing the transformed saved sensor states $x'(t) = x'[x(t)]$, x'(x) being a transformation on the space of possible sensor states.

10. The method according to claim 3 wherein said reference sensor state $x_0$ in the space of possible sensor states is determined to be a sensor state that is a local maximum of a function on the space of possible sensor states, the value of said function at a sensor state being determined to be the number of times said sensor state appears in the collection of saved sensor states in a predetermined time interval.

11. The method according to claim 3 wherein said reference sensor state $x_0$ in the space of possible sensor states is determined as a sensor state produced by a stimulus determined by a user.

12. The method according to claim 3 wherein said reference vectors $h_{0a}$ at the reference sensor state $x_0$ are determined by processing a predetermined collection of said saved sensor states x(t), the saved sensor states in said predetermined collection being in a small neighborhood of the sensor state $x_0$.

13. The method according to claim 12 wherein said processing has the property that the transformed reference vectors $$h'_{0a} = \frac{\partial x'}{\partial x} h_{0a}$$

at the transformed reference sensor state $x_0' = x'(x_0)$ are approximately produced by said processing of the transformed sensor states in the predetermined collection $x'(t) = x'[x(t)]$, $x'(x)$ being a transformation on the space of possible sensor states.

14. The method according to claim 13 wherein said transformation $x'(x)$ is an invertible transformation on the space of possible sensor states.

15. The method according to claim 12 wherein the reference vectors $h_{0a}$ at the reference sensor state $x_0$ are determined to be $$h_{0a} = \sum_{j=1,\ldots,N_{\Delta T}} w_j h_{0a}(j),$$

$h_{0a}(j)$ being the reference vectors determined at said reference sensor state $x_0$ from said saved sensor states in a predetermined time interval with label j, $N_{\Delta T}$ being the number of said predetermined time intervals, and $w_j$ being a predetermined number depending on j.

16. The method according to claim 3 wherein determining said reference vectors $h_{0a}$ at the reference sensor state $x_0$ further includes the steps of:

a) determining an approximate value of the time derivative $$\hat{h}_i = \frac{dx}{dt}\bigg|_{t_i}$$

at each time point $t_i$ of a predetermined collection of the time points at which sensor states $x(t)$ have been saved, i being an integer label and said sensor states $x(t_i)$ at said time points being in a small neighborhood of the reference sensor state $x_0$;

b) partitioning the values of the indices i into C non-empty partitioning sets labeled $S_c$, $c=1, \ldots, C$, C being a predetermined integer;

c) determining the value of E for each possible way of creating the partitioning sets $S_c$, E depending on the quantities $\hat{h}_i$ and on the partitioning sets $S_c$;

d) determining $h_c$, the principal vectors at said $x_0$, $$h_c = \frac{1}{N'_c} \sum_{i \varepsilon S_c} \hat{h}_i,$$

$N'_c$ being a predetermined number dependent on c and $S_c$ being the partitioning sets that lead to the smallest value of E; and e) determining the reference vectors $h_{0a}$ at said reference sensor state $x_0$ to be a predetermined subset of said principal vectors at $x_0$.

17. The method according to claim 16 wherein the quantity E for each collection of partitioning sets $S_c$ is $$E = \sum_{c=1,\ldots,C} |M_c|^p,$$

$|M_c|$ being the determinant of $M_c$, $M_c$ being given by $$M_c = \frac{1}{N_c} \sum_{i \varepsilon S_c} \hat{h}_i \hat{h}_i,$$

$N_c$ being a predetermined number dependent on c, and p being a predetermined real positive number.

18. The method according to claim 16 wherein determining said reference vectors $h_{0a}$ at the reference sensor state $x_0$ further includes the steps of:

a) ordering said principal vectors $h_c$ so that the corresponding quantities $|M_c|$ are in order of ascending magnitude, $|M_c|$ being the determinant of $M_c$, $M_c$ being given by $$M_c = \frac{1}{N_c} \sum_{i \varepsilon S_c} \hat{h}_i \hat{h}_i,$$

and $N_c$ being a predetermined number dependent on c; and b) determining the reference vectors at said reference sensor state $x_0$ to be the first N principal vectors that are linearly independent, N being the number of dimensions of the space of possible sensor states.

19. The method according to claim 3 wherein each said reference vector at $x_0$ is determined to be a directed line segment in the space of possible sensor states, said directed line segment connecting two or more sensor states, said line segment connecting two or more sensor states being produced by two or more stimuli that are determined by a user.

20. The method according to claim 3 wherein the processing of at least one of said saved sensor states $x(t)$, said reference sensor state $x_0$, and said reference vectors $h_{0a}$ to determine one or more preferred vectors $h_a$ at each sensor state x in said predetermined collection of sensor states has the property that the preferred vectors $$h'_a = \frac{\partial x'}{\partial x} h_a$$

at the transformed said sensor state $x' = x'(x)$ are approximately produced by the processing of at least one of the transformed time series of said saved sensor states $x'(t) = x'[x(t)]$ and the transformed said reference sensor state $x_0' = x'(x_0)$ and the transformed said reference vectors $$h'_{0a} = \frac{\partial x'}{\partial x} h_{0a}$$

at the transformed said reference sensor state, $x'(x)$ being a transformation on the space of possible sensor states.

21. The method according to claim 20 wherein said transformation $x'(x)$ is an invertible transformation on the space of possible sensor states.

22. The method according to claim 3 wherein the preferred vectors $h_a$ at each sensor state x in said predetermined collection of sensor states are determined to be $$h_a = \sum_{j=1,\ldots,N_{\Delta T}} w_j h_a(j),$$

$h_a(j)$ being the preferred vectors determined at said sensor state x by processing at least one of said reference sensor state $x_0$ and said saved sensor states in a predetermined time interval with label j, $N_{\Delta T}$ being the number of said predetermined time intervals, and $w_j$ being a predetermined number depending on j.

23. The method according to claim 3 wherein the processing of at least one of said saved sensor states $x(t)$ and said reference sensor state $x_0$ and said reference vectors $h_{0a}$ to determine the path $\tilde{x}(\tau)$, $0 \leq \tau \leq 1$, in the space of possible sensor states, said path connecting the reference sensor state $x_0=\tilde{x}(0)$ to a sensor state of interest $\tilde{x}(1)$, has the property that an approximation of the transformed path $\tilde{x}'(\tau)=x'[\tilde{x}(\tau)]$ is produced by processing at least one of the time series of transformed said saved sensor states $x'(t)=x'[x(t)]$ and the transformed said reference sensor state $x_0'=x'(x_0)$ and the transformed said reference vectors $$h'_{0a} = \frac{\partial x'}{\partial x} h_{0a}$$

at the transformed said reference sensor state, where $x'(x)$ is a transformation on the space of possible sensor states.

24. The method according to claim 23 wherein said transformation $x'(x)$ is an invertible transformation on the space of possible sensor states.

25. The method according to claim 3 wherein determining aspects of the nature of stimuli further includes the steps of:
   a) determining the representations s(t) of each of the said saved sensor states x(t);
   b) determining another time series of sensor states to be said time series of representations s(t);
   c) processing said another time series of sensor states to determine the representations of each of the representations of a predetermined collection of sensor states in the space of said saved sensor states x(t); and
   d) processing at least one of the saved output signals of the detector and the sensor states in said predetermined collection and their representations and the representations of their representations to determine aspects of the nature of the stimuli producing said sensor states in said predetermined collection.

26. The method according to claim 3 wherein at least one step is performed by a general-purpose computer performing the computations of a software program, said software program having an architecture selected from the group consisting of a serial architecture, parallel architecture, and neural network architecture.

27. The method according to claim 3 wherein at least one step is performed by a computer hardware circuit, said circuit having an architecture selected from the group consisting of a serial architecture, parallel architecture, and neural network architecture.

28. A method of detecting and processing time-dependent signals from a stimulus source, the method comprising the steps of:
   a) detecting with a detector the signal energy from stimuli from said stimulus source at predetermined time points;
   b) processing the output signals of the detector to produce a sensor state x(t) at each time point t in a collection of predetermined time points, said sensor state x(t) including one or more numbers;
   c) saving in computer memory said output signals of the detector and said sensor states x(t) at each of said predetermined time points;
   d) determining a reference sensor state $x_0$ in the space of possible sensor states;
   e) determining one or more preferred vectors $h_a$ at each sensor state x in a predetermined collection of sensor states by processing a predetermined collection of said saved sensor states, the sensor states in said predetermined collection being in a small neighborhood of said sensor state x and said preferred vectors having one or more dimensions;
   f) processing at least one of said reference sensor state $x_0$ and said preferred vectors $h_a$ to determine paths in the space of possible sensor states, each said path being between the reference sensor state $x_0$ and a sensor state x in a predetermined collection of sensor states;
   g) determining the representation $$s = \int_{x_0}^{x} \delta s$$

of each sensor state x in a predetermined collection of sensor states, said integral being along said path connecting $x_0$ to x, $\delta s$ at each sensor state on said path satisfying $$\delta x = \sum_{a=1,\ldots,N} h_a \delta s_a,$$

$\delta x$ being a small displacement along the path at said sensor state on said path, $h_a$ denoting the preferred vectors near said sensor state on said path, and N being the number of dimensions of the space of possible sensor states;
   h) saving in computer memory said sensor states in said predetermined collection of sensor states and said representations of the sensor states in said predetermined collection of sensor states; and
   i) processing at least one of the saved output signals of the detector and the sensor states in said predetermined collection and corresponding representations to determine aspects of the nature of the stimuli producing the sensor states in said predetermined collection.

29. The method according to claim 28 wherein said preferred vectors $h_a$ at said sensor state x are determined by processing a predetermined collection of said saved sensor states, the sensor states x(t) in said predetermined collection being in a small neighborhood of the sensor state x and said processing having the property that the transformed preferred vectors $$h'_a = \frac{\partial x'}{\partial x} h_a$$

at the transformed sensor state $x'=x'(x)$ are approximately produced by said processing of the transformed said saved sensor states in the predetermined collection $x'(t)=x'[x(t)]$, $x'(x)$ being a transformation on the space of possible sensor states.

30. The method according to claim 29 wherein said transformation $x'(x)$ is an invertible transformation on the space of possible sensor states.

31. The method according to claim 28 wherein determining the preferred vectors $h_a$ at each sensor state x in said predetermined collection of sensor states further includes the steps of:
   a) determining an approximate value of a time derivative $$\hat{h}_i = \frac{dx}{dt}\bigg|_{t_i}$$

at each time point $t_i$ of a collection of predetermined time points at which sensor states x(t) have been saved, i being an integer label and said sensor states $x(t_i)$ at said predetermined time points being in a small neighborhood of said sensor state x;
   b) partitioning the values of the indices i into C non-empty partitioning sets labeled $S_c$, c=1, . . . , C, C being a predetermined integer;

c) determining the value of E for all possible ways of creating the partitioning sets $S_c$, E depending on the quantities $\hat{h}_i$ and on the partitioning sets $S_c$;

d) determining $h_c$, the principal vectors at said sensor state x, $$h_c = \frac{1}{N'_c} \sum_{i \in S_c} \hat{h}_i,$$

$N'_c$ being a predetermined number dependent on c and $S_c$ being the partitioning sets that lead to the smallest value of E;

e) determining the preferred vectors $h_a$ at x to be a predetermined subset of the principal vectors at x.

32. The method according to claim 31 wherein the quantity E is $$E = \sum_{c=1,\ldots,C} |M_c|^p,$$

$|M_c|$ being the determinant of $M_c$, $M_c$ being given by $$M_c = \frac{1}{N_c} \sum_{i \in S_c} \hat{h}_i \hat{h}_i,$$

$N_c$ being a predetermined number dependent on c, and p being a predetermined real positive number.

33. The method according to claim 31 wherein determining the preferred vectors $h_a$ at each sensor state x in said predetermined collection of sensor states further includes the steps of:

a) ordering said principal vectors $h_c$ so that the corresponding quantities $|M_c|$ are in order of ascending magnitude, $|M_c|$ being the determinant of $M_c$, $M_c$ being given by $$M_c = \frac{1}{N_c} \sum_{i \in S_c} \hat{h}_i \hat{h}_i,$$

and $N_c$ being a predetermined number dependent on c; and b) determining the preferred vectors $h_a$ at x to be the first N principal vectors that are linearly independent, N being the number of dimensions of the space of possible sensor states.

34. The method according to claim 28 wherein the preferred vectors $h_a$ at each sensor state x in a predetermined collection of sensor states are determined as $$h_a = \sum_{j=1,\ldots,N_{\Delta T}} w_j h_a(j),$$

$h_a(j)$ being the preferred vectors determined at said sensor state x from said saved sensor states in a predetermined time interval with label j, $N_{\Delta T}$ being the number of said predetermined time intervals, and $w_j$ being a predetermined number depending on j.

35. The method according to claim 28 wherein determining said path connecting $x_0$ to x further includes the steps of:

a) determining a type m trajectory through $x_0$, m being a predetermined integer, by moving across a space of possible sensor states along a direction of at least one of said preferred vector $h_m$ near $x_0$ and minus one times said preferred vector $h_m$ near $x_0$, and then moving across the space of possible sensor states along a direction of at least one of said preferred vector $h_m$ near each subsequently sensor state and minus one times said preferred vector $h_m$ near each subsequently encountered sensor state, and repeating this last procedure a predetermined number of times;

b) determining a type n trajectory through each sensor state on each trajectory of a last-determined type, n being an integer unequal to any of the indices labeling previously determined trajectories, by moving across the space of possible sensor states along a direction of at least one of said preferred vector $h_n$ near said each sensor state and minus one times said preferred vector $h_n$ near said each sensor state, and than moving across the space of possible sensor states along a direction of at least one of said preferred vector $h_n$ near each subsequently encountered sensor state and minus one times said preferred vector $h_n$ near each subsequently encountered sensor state, and repeating this last procedure a predetermined number of times;

c) performing step (b) until said sensor state x has been reached by the last-determined trajectory; and d) determining said path connecting the reference sensor state $x_0$ to said sensor state x to be a path containing at most one segment of each type of said determined trajectories, said segments being connected in the order in which said determined trajectory types were determined.

36. A method of detecting and processing time-dependent signals from a stimulus source, the method comprising the steps of:

a) detecting with a detector the signal energy from stimuli from the stimulus source at predetermined time points;

b) processing the output signals of the detector to produce a sensor state x(t) at each time point t in a collection of predetermined time points, said sensor state x(t) including one or more numbers;

c) saving in computer memory said output signals of the detector and said sensor states x(t) at each of said predetermined time points;

d) determining a reference sensor state $x_0$ in the space of possible sensor states;

e) determining one or more reference vectors $h_{0a}$ at the reference sensor state $x_0$, each said reference vector having one or more dimensions;

f) determining a parallel transport operation at each sensor state x in a predetermined collection of sensor states by processing a predetermined collection of said saved sensor states, the saved sensor states in said predetermined collection being in a small neighborhood of said sensor state x and said parallel transport operation transporting vectors across the space of possible sensor states near x;

g) processing at least one of said saved sensor states x(t), said reference sensor state $x_0$, said reference vectors $h_{0a}$ and said parallel transport operation to determine one or more preferred vectors $h_a$ at each sensor state x in a predetermined collection of sensor states, each said preferred vector having one or more dimensions;

h) processing at least one of said saved sensor states x(t), the reference sensor state $x_0$, said reference vectors $h_{0a}$ and said parallel transport operation to determine paths across the space of possible sensor states, each said path being between the reference sensor state $x_0$ and a sensor state x in a predetermined collection of sensor states;

i) determining the representation $$s = \int_{x_0}^{x} \delta s$$

of each sensor state x in a predetermined collection of sensor states, said integral being along said path connecting $x_0$ to x, $\delta s$ at each sensor state on said path satisfying $$\delta x = \sum_{a=1,\ldots,N} h_a \delta s_a,$$

$\delta x$ being a small displacement along the path at said sensor state on said path, $h_a$ denoting the preferred vectors near said sensor state on said path, and N being the number of dimensions of the space of possible sensor states;

j) saving in computer memory said sensor states in said predetermined collection of sensor states and said representations of the sensor states in said predetermined collection of sensor states; and k) processing at least one of the saved output signals of the detector and the sensor states in said predetermined collection and corresponding representations to determine aspects of the nature of the stimuli producing the sensor states in said predetermined collection.

37. The method according to claim 36 wherein the parallel transport operation that is determined by processing said predetermined collection of saved sensor states x(t) in a small neighborhood of said sensor state x parallel transports a vector V at x along a line segment $\delta x$ at x into a parallel transported vector $\tilde{V}$ at a destination sensor state x+$\delta x$ and the parallel transport operation at the transformed said sensor state x'=x'(x), said parallel transport operation being determined by processing the transformed said saved sensor states x'(t)=x'[x(t)] in a small neighborhood of the transformed said sensor state x', approximately parallel transports the transformed said vector $$V' = \frac{\partial x'}{\partial x} V$$

at x' along the transformed said line segment $$\delta x' = \frac{\partial x'}{\partial x} \delta x$$

at x' into the transformed said parallel transported vector $$\tilde{V}' = \frac{\partial x'}{\partial x} \tilde{V}$$

at the transformed said destination sensor state x'(x+$\delta x$), x'(x) being a transformation on the space of possible sensor states.

38. The method according to claim 37 wherein said transformation x'(x) is an invertible transformation on the space of possible sensor states.

39. The method according to claim 36 wherein determining said parallel transport operation at said predetermined sensor state it further includes the steps of:

a) determining three said saved sensor states within a small neighborhood of said predetermined sensor state it, said three saved sensor states being saved at times within a predetermined time interval;

b) determining a pair of line segments, the first said line segment connecting the earlier two of said three sensor states, said earlier two sensor states being saved at times earlier than the time at which the last saved sensor state of the three sensor states was saved and said line segment being directed from the sensor state at the earlier time to the sensor state at the later time, and the second said line segment connecting the later two of said three sensor states, said later two sensor states being saved at times later than the time at which the first saved sensor state of the three sensor states was saved and said line segment being directed from the sensor state at the earlier time to the sensor state at the later time;

c) determining zero or more additional line segment pairs in the neighborhood of said predetermined sensor state x; and d) determining a parallel transport operation at said predetermined sensor state it that transports vectors along paths through the space of possible sensor states near it and that parallel transports the first line segment in each said line segment pair along itself into a line segment that approximates the second line segment of the same line segment pair.

40. The method according to claim 36 wherein determining said parallel transport operation at said predetermined sensor state x further includes the steps of:

a) determining three said saved sensor states within a small neighborhood of said predetermined sensor state x, said three saved sensor states being saved at times within a predetermined time interval;

b) determining a pair of line segments, the first said line segment connecting the earlier two of said three sensor states, said earlier two sensor states being saved at times earlier than the time at which the last saved sensor state of the three sensor states was saved and said line segment being directed from the sensor state at the earlier time to the sensor state at the later time, and the second said line segment connecting the later two of said three sensor states, said later two sensor states being saved at times later than the time at which the first saved sensor state of the three sensor states was saved and said line segment being directed from the sensor state at the earlier time to the sensor state at the later time;

c) determining a collection of zero or more additional line segment pairs in the neighborhood of said predetermined sensor state x;

d) determining one or more collections, each said collection labeled by an integer i and containing one or more said line segment pairs for which there is a unique $\hat{\Gamma}_{lm}{}^{k}(i)$ that satisfies $$\delta d x^k = - \sum_{l,m=1,\ldots,N} \hat{\Gamma}_{lm}{}^{k}(i) dx_l dx_m$$

for each line segment pair, dx and dx+$\delta$dx, in said collection, N being the number of dimensions of the space of possible sensor states;

e) determining the affine connection $\Gamma_{lm}^{k}$ at said predetermined sensor state x, $$\Gamma_{lm}^{k} = \frac{1}{W_{\Gamma}} \sum_{i=1,\ldots,N_{\Gamma}} \hat{\Gamma}_{lm}^{k}(i),$$

$N_{\Gamma}$ being the number of said collections of line segment pairs for which there is a unique said $\hat{\Gamma}_{lm}^{k}(i)$ and $W_{\Gamma}$ being a predetermined number; and f) determining the parallel transport operation at said predetermined sensor state x so that the vector V at x is parallel transported along the line segment δx at x into the vector V+δV at x+δx, δV being $$\delta V^{k} = -\sum_{l,m=1,\ldots,N} \Gamma_{lm}^{k} V^{l} \delta x_{m},$$

and N being the number of dimensions of the space of possible sensor states.

41. The method according to claim 36 wherein said parallel transport operation at said predetermined sensor state x parallel transports the vector V at x along the line segment δx at x into the vector V+δV at x+δx, δV being $$\delta V^{k} = \sum_{j=1,\ldots,N_{\Delta T}} w_{j} \delta V(j)^{k},$$

δV(j) having the property that the parallel transport operation determined from said saved sensor states in a predetermined time interval with label j parallel transports the vector V at x along the line segment δx at x into the vector V+δV(j) at x+δx, $N_{\Delta T}$ being the number of said predetermined time intervals, and $w_j$ being a predetermined number depending on j.

42. The method according to claim 36 wherein determining the path connecting the reference sensor state $x_0$ to the sensor state x further includes the steps of:

a) determining a type m trajectory through $x_0$, m being a predetermined integer, by parallel transporting the reference vector $h_{0m}$ along a direction of at least one of itself and minus one times itself, and parallel transporting the resultant vector along a direction of at least one of itself and minus one times itself and repeating the last procedure a predetermined number of times;

b) parallel transporting the reference vectors $h_{0a}$ along said type m trajectory to produce preferred vectors $h_a$ at each sensor state on said trajectory;

c) determining a type n trajectory through each sensor state on each trajectory of a last-determined type, n being an integer unequal to any of the indices labeling any of the previously determined trajectories, by parallel transporting said preferred vector $h_n$ at each sensor state on said each trajectory along a direction of at least one of itself and minus one times itself and parallel transporting the resultant vector along a direction of at least one of itself and minus one times itself and repeating this last procedure a predetermined number of times;

d) parallel transporting said preferred vectors $h_a$ located at each sensor state on each trajectory of a next to last-determined type along said type n trajectory that passes through said each sensor state in order to produce preferred vectors $h_a$ at each sensor state on said type n trajectory;

e) performing steps (c) and (d) until said predetermined sensor state x has been reached by a determined trajectory and by said process of parallel transporting the preferred vectors $h_a$; and f) determining said path connecting the reference sensor state $x_0$ to said sensor state x to be a path containing at most one segment of each type of said determined trajectories, said segments being connected in the order in which said determined trajectory types were determined.

43. A method of detecting and processing time-dependent signals from a stimulus source, the method comprising the steps of:

a) detecting with a detector the signal energy from stimuli from the stimulus source at predetermined time points;

b) processing the output signals of the detector to produce a sensor state x(t) at each time point t in a collection of predetermined time points, said sensor state x(t) including one or more numbers;

c) saving in computer memory said output signals of the detector and said sensor states x(t) at each of said predetermined time points;

d) determining a reference sensor state $x_0$ in the space of possible sensor states;

e) determining one or more reference vectors $h_{0a}$ at the reference sensor state $x_0$, each said reference vector having one or more dimensions;

f) determining a metric operation at each sensor state x in a collection of predetermined sensor states by processing a predetermined collection of said saved sensor states, the saved sensor states in said predetermined collection being in a small neighborhood of said sensor state x and said metric operation assigning lengths to vectors near x;

g) determining a parallel transport operation at each sensor state x in a predetermined collection of sensor states, said parallel transport operation transporting vectors across the space of possible sensor states near x;

h) processing at least one of said saved sensor states x(t), said reference sensor state $x_0$, said reference vectors $h_{0a}$, said metric operation and said parallel transport operation to determine one or more preferred vectors $h_a$ at each sensor state x in a predetermined collection of sensor states, each said preferred vector having one or more dimensions;

i) processing at least one of said saved sensor states x(t), said reference sensor state $x_0$, said reference vectors $h_{0a}$, said metric operation and said parallel transport operation to determine paths across the space of possible sensor states, each said path being between the reference sensor state $x_0$ and a sensor state x in a predetermined collection of sensor states;

j) determining the representation $$s = \int_{x_0}^{x} \delta s$$

of each sensor state x in a predetermined collection of sensor states, said integral being along said path connecting $x_0$ to x, δs at each sensor state on said path satisfying $$\delta x = \sum_{a=1,\ldots,N} h_a \delta s_a,$$

δx being a small displacement along the path at said sensor state on said path, $h_a$ denoting the preferred vectors near said sensor state on said path, and N being the number of dimensions of the space of possible sensor states;

k) saving in computer memory said sensor states in said predetermined collection of sensor states and said representations of the sensor states in said predetermined collection of sensor states; and l) processing at least one of the saved output signals of the detector and the sensor states in said predetermined collection and corresponding representations to determine aspects of the nature of the stimuli producing the sensor states in said predetermined collection.

44. The method according to claim 43 wherein said metric operation at said predetermined sensor state x assigns a length to a vector V at x that is the same as the length assigned to the transformed said vector $$V' = \frac{\partial x'}{\partial x} V$$

at the transformed said sensor state x'=x'(x) by the metric at x', said metric at x' being determined by processing the transformed saved sensor states x'(t)=x'[x(t)], each x(t) being one of the saved sensor states in said predetermined collection of saved sensor states near x and x'(x) being a transformation on the space of possible sensor states.

45. The method according to claim 44 wherein said transformation x'(x) is an invertible transformation on the space of possible sensor states.

46. The method according to claim 43 wherein determining the metric operation at each said predetermined sensor state x further includes the steps of:

a) determining two said saved sensor states within a small neighborhood of said predetermined sensor state x, said saved sensor states being saved at times within a predetermined time interval;

b) determining a line segment connecting said two sensor states, said line segment being directed from the sensor state at the earlier time to the sensor state at the later time;

c) determining zero or more additional line segments in the neighborhood of $x$,; and d) determining a metric operation at said predetermined sensor state x that assigns metric lengths to vectors at said predetermined sensor state x and that assigns approximately the same metric length to each of said line segments.

47. The method according to claim 43 wherein determining the metric operation at said predetermined sensor state x further includes the steps of:

a) determining two said saved sensor states within a small neighborhood of said predetermined sensor state x, said saved sensor states being saved at times within a predetermined time interval;

b) determining a line segment connecting said two sensor states, said line segment being directed from the sensor state at the earlier time to the sensor state at the later time;

c) determining zero or more additional line segments in the neighborhood of said predetermined sensor state x;

d) determining one or more collections of said line segments, each collection labeled with i and containing one or more such line segments for which there is a unique $\hat{g}_{kl}(i)$ that satisfies $$\sum_{k,l=1,\ldots,N} \hat{g}_{kl}(i) dx_k dx_l = |d\lambda|^2$$

for each line segment dx in said collection, $|d\lambda|^2$ being a predetermined number, and N being the number of dimensions of the space of possible sensor states;

e) determining the metric tensor $g_{kl}$ at said predetermined sensor state x, $$g_{kl} = \frac{1}{W_g} \sum_{i=1,\ldots,N_g} \hat{g}_{kl}(i),$$

$N_g$ being the number of said collections of line segments at said predetermined sensor state x for which there is a unique said $\hat{g}_{kl}(i)$ and $W_g$ being a predetermined number; and f) determining the metric operation at said predetermined sensor state x so that the vector V at x is assigned the metric length |V|

$$|V|^2 = \sum_{k,l=1,\ldots,N} g_{kl} V^k V^l.$$

48. The method according to claim 43 wherein said metric operation at said predetermined sensor state x assigns the metric length |V| to the vector V at x, |V| being $$|V|^2 = \sum_{j=1,\ldots,N_{\Delta T}} w_j |V(j)|^2,$$

|V(j)| having the property that the metric operation determined from said saved sensor states in a predetermined time interval with label j assigns the metric length |V(j)| to the vector V at x, $N_{\Delta T}$ being the number of said predetermined time intervals, and $w_j$ being a predetermined number depending on j.

49. The method according to claim 43 wherein said parallel transport operation at said predetermined sensor state x parallel transports a line segment at x along itself into a parallel transported line segment, said parallel transported line segment having approximately the same metric length as said line segment at x.

50. The method according to claim 43 wherein determining said parallel transport operation at said predetermined sensor state x further includes the steps of:

a) determining the affine connection $\Gamma_{lm}^k$ at said predetermined sensor state x $$\Gamma_{lm}^k = \frac{1}{2} \sum_{n,1,\ldots,N} g^{kn} \left( \frac{\partial g_{mn}}{\partial x_l} + \frac{\partial g_{nl}}{\partial x_m} - \frac{\partial g_{lm}}{\partial x_n} \right),$$

$g^{kl}$ being the contravariant tensor that is the inverse of $g_{kl}$, $g_{kl}$ satisfying $$|V|^2 = \sum_{k,l=1,\ldots,N} g_{kl} V^k V^l,$$

and |V| being the length assigned to a vector V at x by the metric operation at x, and N being the number of dimensions of the space of possible sensor states; and b) determining the parallel transport operation at said predetermined sensor state x so that a vector V at x is parallel transported along a line segment δx at x into the vector V+δV at x+δx, δV being $$\delta V^k = - \sum_{l,m=1,\ldots,N} \Gamma^k_{lm} V^l \delta x_m,$$

and N being the number of dimensions of the space of possible sensor states.

51. The method according to claim 43 wherein determining the path connecting the reference sensor state $x_0$ to the sensor state x further includes the steps of:

a) determining a type m trajectory through $x_0$, m being a predetermined integer, by parallel transporting the reference vector $h_{0m}$ along a direction of at least one of itself and minus one times itself and parallel transporting the resultant vector along a direction of at least one of itself and minus one times itself and repeating the last procedure a predetermined number of times;

b) parallel transporting the reference vectors $h_{0a}$ along said type m trajectory to produce preferred vectors $h_a$ at each sensor state on said trajectory;

c) determining a type n trajectory through each sensor state on each trajectory of a last-determined type, n being an integer unequal to any of the indices labeling any of the previously determined trajectories, by parallel transporting said preferred vector $h_n$ at each sensor state on said each trajectory along a direction of at least one of itself and minus one times itself and parallel transporting the resultant vector along a direction of at least one of itself and minus one times itself and repeating this last procedure a predetermined number of times;

d) parallel transporting said preferred vectors $h_a$ located at each sensor state on each trajectory of a next to last-determined type along said type n trajectory that passes through said each sensor state in order to produce preferred vectors $h_a$ at each sensor state on said type n trajectory;

e) repeating steps (c)–(d) until said predetermined sensor state x has been reached by a determined trajectory and by said process of parallel transporting the preferred vectors $h_a$; and f) determining said path to be a path connecting the reference sensor state $x_0$ to said sensor state x, said path containing at most one segment of each type of said determined trajectories, said segments being connected in the order in which said determined trajectory types were determined.

52. A method of translating stimuli from one stimulus source S into stimuli from another stimulus source $\overline{S}$, the method comprising the steps of:

a) detecting with a detector the signal energy from stimuli from said source S at predetermined time points;

b) processing the output signals of the detector to produce a sensor state x(t) at each time point t in a collection of predetermined time points, said sensor state x(t) including one or more numbers;

c) saving in computer memory said sensor state x(t) at each time point in said collection;

d) processing said saved sensor states x(t) to produce a representation of each sensor state x of a predetermined collection of sensor states in the space of possible sensor states, each said representation including one or more numbers and said processing having the property that the representation of a sensor state x determined by processing a time series of sensor states x(t) is approximately the same as the representation of the transformed sensor state x'=x'(x) determined by processing the transformed time series of sensor states x'(t)=x'[x(t)], x'(x) being an invertible transformation on the space of possible sensor states;

e) using a computer to save said sensor states x in said predetermined collection of sensor states and to save said representations of the sensor states in said predetermined collection of sensor states;

f) detecting with a detector the signal energy from stimuli from said source $\overline{S}$ at predetermined time points;

g) processing the output signals of said detector to produce a sensor state $\overline{x}(t)$ at each time point t in a collection of predetermined time points, said sensor state $\overline{x}(t)$ including one or more numbers;

h) saving in computer memory said sensor state $\overline{x}(t)$ at each time point in said collection;

i) processing said saved sensor states $\overline{x}(t)$ to produce a representation of each sensor state $\overline{x}$ of a predetermined collection of sensor states in the space of sensor states produced by possible stimuli from source $\overline{S}$, each said representation including one or more numbers;

j) using a computer to save said sensor states $\overline{x}$ in said predetermined collection of sensor states and to save said representations of the sensor states in said predetermined collection of sensor states: and k) determining a time series of stimuli from said stimulus source S that produces a time series of sensor states, and determining a time series of stimuli from said stimulus source $\overline{S}$ that produces a time series of sensor states, the sensor state at each time in said time series of sensor states produced by said stimuli from S having the same representation as the sensor state at the same said time in the time series of sensor states produced by said stimuli from $\overline{S}$.

53. The method according to claim 52 wherein the stimulus source S produces at least one of electromagnetic signals, auditory signals, and mechanical signals and wherein the stimulus source $\overline{S}$ produces at least one of electromagnetic signals, auditory signals, and mechanical signals.

54. The method according to claim 52 wherein the energy of the stimuli from S is carried by a medium selected from the group consisting of empty space, the earth's atmosphere, wave guide, wire, optical fiber, gaseous medium, liquid medium, and solid medium, and wherein the energy of the stimuli from $\overline{S}$ is carried by a medium selected from the group consisting of empty space, the earth's atmosphere, wave guide, wire, optical fiber, gaseous medium, liquid medium, and solid medium.

55. The method according to claim 52 wherein the energy of the stimuli from source S is detected by detectors selected from the group consisting of a radio antenna, microwave antenna, infrared camera, optical camera, ultraviolet detector, X-ray detector, microphone, hydrophone, pressure transducer, translational position detector, angular position detector, translational motion detector, angular motion detector, electrical voltage detector, and electrical current detector and wherein the energy of the stimuli from source $\overline{S}$ is detected by detectors selected from the group consisting of a radio antenna, microwave antenna, infrared camera, optical camera, ultraviolet detector, X-ray detector, microphone, hydrophone, pressure transducer, translational position detector, angular position detector, translational motion detector, angular motion detector, electrical voltage detector, and electrical current detector.

56. A method of communicating information from a transmitter to a receiver, the method comprising the steps of a) determining information to be communicated from the transmitter to the receiver, said information consisting of a collection of number arrays, each said number array including one or more numbers;

b) saving in computer memory said information;

c) determining a transmitter state x (t) at each time point t in a predetermined collection of time points, x(t) at each said time point being one or more numbers, the processing of said time series of transmitter states determining a representation of each transmitter state in a predetermined collection of said transmitter states, the representations of the transmitter states in a predetermined collection of said transmitter states being said information, each said representation including one or more numbers and said processing having the property that the representation of a transmitter state x determined by a time series of transmitter states x(t) is approximately the same as the representation of the transformed transmitter state x'=x'(x) determined by the transformed time series of transmitter states x'(t)=x'[x(t)], x'(x) being an invertible transformation on the space of possible transmitter states;

d) saving in computer memory said transmitter states x(t) at each time point t in said predetermined collection of time points;

e) using the transmitter to transmit energy, said energy transmission being controlled by said determined time series of transmitter states;

f) detecting with a detector of the receiver energy transmitted by the transmitter at a set of predetermined time points;

g) processing the output of the detector of the receiver to produce a time series of receiver states $\overline{x}(t)$ at predetermined time points t, $\overline{x}(t)$ at each said time point t being one or more numbers;

h) saving in computer memory said receiver states $\overline{x}(t)$ at each of said predetermined time points t;

i) processing said saved receiver states $\overline{x}(t)$ to produce a representation of each saved receiver state in a predetermined collection of said saved receiver states;

j) saving in computer memory said representations of the saved receiver states in said collection;

k) processing the saved representations to determine said information; and l) saving in computer memory said information.

57. The method according to claim 56 wherein the transmitter transmits at least one of electromagnetic signals, auditory signals and mechanical signals.

58. The method according to claim 56 wherein the energy transmitted by the transmitter is carried by a medium selected from the group consisting of empty space, the earth's atmosphere, wave-guide, wire, optical fiber, gaseous medium, liquid medium, and solid medium.

59. The method according to claim 56 wherein the receiver detectors are selected from the group consisting of radio antenna, microwave antenna, infrared camera, optical camera, ultraviolet detector, X-ray detector, microphone, hydrophone, pressure transducer, translational position detector, angular position detector, translational motion detector, angular motion detector, electrical voltage detector, and electrical current detector.

60. The method according to claim 56 wherein the representation of a receiver state $\overline{x}$ determined by a time series of receiver states $\overline{x}(t)$ is approximately the same as the representation of the transformed receiver state $\overline{x}=x'(\overline{x})$ determined by the transformed time series of receiver states $\overline{x}(t)=x'[\overline{x}(t)]$, $x'(\overline{x})$ being an invertible transformation on the space of possible receiver states.

* * * * *